United States Patent
Odunsi et al.

(10) Patent No.: US 12,275,946 B2
(45) Date of Patent: Apr. 15, 2025

(54) COMPOSITIONS AND METHODS FOR RAPID CLONING OF T-CELL RECEPTORS

(71) Applicant: Health Research, Inc., Buffalo, NY (US)

(72) Inventors: Kunle Odunsi, Williamsville, NY (US); Richard Koya, Williamsville, NY (US); Takemasa Tsuji, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 1818 days.

(21) Appl. No.: 16/318,787

(22) PCT Filed: Aug. 1, 2017

(86) PCT No.: PCT/US2017/044920
§ 371 (c)(1),
(2) Date: Jan. 18, 2019

(87) PCT Pub. No.: WO2018/026827
PCT Pub. Date: Feb. 8, 2018

(65) Prior Publication Data
US 2019/0183935 A1 Jun. 20, 2019

Related U.S. Application Data

(60) Provisional application No. 62/369,321, filed on Aug. 1, 2016.

(51) Int. Cl.
| | | |
|---|---|---|
| *C12N 15/85* | (2006.01) | |
| *A61K 35/17* | (2015.01) | |
| *A61K 39/00* | (2006.01) | |
| *C07K 14/725* | (2006.01) | |
| *C12N 5/0783* | (2010.01) | |
| *C12N 15/01* | (2006.01) | |
| *C12N 15/10* | (2006.01) | |
| *C12N 15/66* | (2006.01) | |
| *C12Q 1/6874* | (2018.01) | |
| *C12Q 1/6876* | (2018.01) | |
| *G01N 33/566* | (2006.01) | |
| *G01N 33/574* | (2006.01) | |

(52) U.S. Cl.
CPC ............ *C12N 15/85* (2013.01); *A61K 35/17* (2013.01); *A61K 39/4611* (2023.05); *A61K 39/4632* (2023.05); *A61K 39/464488* (2023.05); *C07K 14/7051* (2013.01); *C12N 5/0638* (2013.01); *C12N 15/01* (2013.01); *C12N 15/1093* (2013.01); *C12N 15/66* (2013.01); *C12Q 1/6874* (2013.01); *C12Q 1/6876* (2013.01); *G01N 33/566* (2013.01); *G01N 33/574* (2013.01); *A61K 2239/31* (2023.05); *A61K 2239/38* (2023.05); *A61K 2239/59* (2023.05); *C12N 2510/00* (2013.01)

(58) Field of Classification Search
None
See application file for complete search history.

(56) References Cited

U.S. PATENT DOCUMENTS

| | | |
|---|---|---|
| 2004/0013648 A1 | 1/2004 | Kingsman et al. |
| 2005/0154053 A1 | 7/2005 | Rhijn et al. |
| 2011/0070191 A1 | 3/2011 | Wong et al. |
| 2015/0079052 A1 | 3/2015 | Stominger et al. |

FOREIGN PATENT DOCUMENTS

| | | | |
|---|---|---|---|
| CN | 102174108 A | 9/2011 | |
| CN | 104870011 A | 8/2015 | |
| CN | 105408473 A | 3/2016 | |
| WO | 02/092770 A2 | 11/2002 | |
| WO | WO-2015113140 A1 * | 8/2015 | ............... A61P 1/16 |

OTHER PUBLICATIONS

Matsuzaki, J., et al., Direct tumor recognition by a human CD4+ T-cell subset potently mediates tumor growth inhibition and orchestrates anti-tumor immune responses, Scientific Reports, Oct. 8, 2015, vol. 5, No. 1, pp. 1-14.

Banu, N., et al., Building and Optimizing a Virus-specific T cell Receptor Library for Targeted Immunotherapy in Viral Infections, Scientific Reports, Feb. 25, 2014, vol. 4, No. 1, pp. 1-10.

Lefranc, M., et al., IMGT, the international ImMunoGeneTics information system 25 years on, Nucleic Acids Research, Jan. 28, 2015, vol. 43, No. D1, pp. D413-D422.

Szymczak, A. L., et al., Correction of multi-gene deficiency in vivo using a single 'self-cleaving' 2A peptide-based retroviral vector, Nature Biotechnology, May 1, 2004, vol. 22, No. 5, pp. 589-594.

(Continued)

*Primary Examiner* — Jennifer Dunston
*Assistant Examiner* — Tiffany Nicole Grooms
(74) *Attorney, Agent, or Firm* — Hodgson Russ LLP

(57) ABSTRACT

Provided are methods, compositions, recombinant DNA molecules, and kits for cloning T cell receptors (TCRs). The methods facilitate construction of TCR expression libraries from biological samples containing antigen-specific T cells, including but not limited to tumor biopsies, including frozen tumor biopsies. Peripheral T cells that were engineered with library-derived TCR genes show potent therapeutic anti-tumor effects. The method can be performed using any sample that contains T cells, and can be performed with oligoclonal populations of T cells, such as T cells that have infiltrated a tumor. Primer combinations for first strand cDNA synthesis, second strand cDNA synthesis, and for cloning a plurality of distinct TCR β and TCR α chains into a plurality of vectors are provided. Cells containing the vectors are provided, as are kits for use in rapid cloning of the TCR β and TCR α chains.

20 Claims, 20 Drawing Sheets

Specification includes a Sequence Listing.

(56) References Cited

OTHER PUBLICATIONS

Wang, G. C., et al., T Cell Receptor alpha-beta Diversity Inversely Correlates with Pathogen-Specific Antibody Levels in Human Cytomegalovirus Infection, Science Translational Medicine, Apr. 4, 2012, vol. 4, No. 128, pp. 1-11.

Pradyot D., et al., Paired analysis of TCRalpha and TCRbeta chains at the single-cell level in mice, The Journal of Clinical Investigation, Jan. 4, 2011, vol. 121, No. 1, pp. 288-295.

Bell, J. R., A Simple Way to Treat PCR Products Prior to Sequencing Using ExoSAP-IT, BioTechniques, May 1, 2008, vol. 44, No. 6, p. 834.

Guo, X. J., et al., Rapid cloning, expression, and functional characterization of paired alpha-beta and gamma-delta T-cell receptor chains from single-cell analysis, Molecular Therapy, Jan. 27, 2016, vol. 3, pp. 1-12.

\* cited by examiner

A
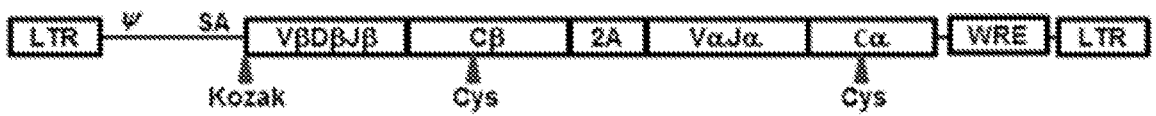
B
1. Synthesis of 1st strand cDNA by reverse transcription
2. Synthesis of second-strand cDNA using multiplexed primers
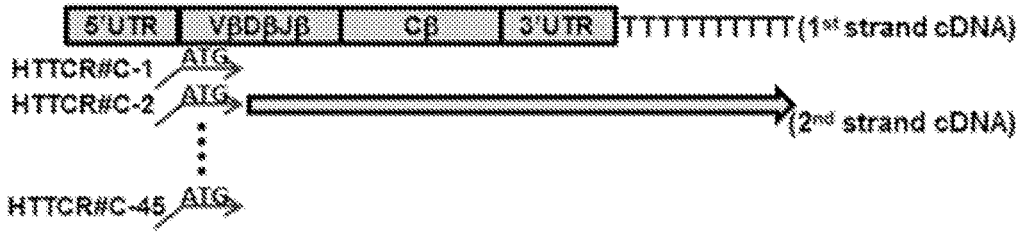
3. Digestion of excess (unused) primers by Exonuclease I
4. Amplification of variable fragments using the common primers
5. Assemble Vβ, Cβ-2A, Vα fragments into a destination TCR-cloning vector
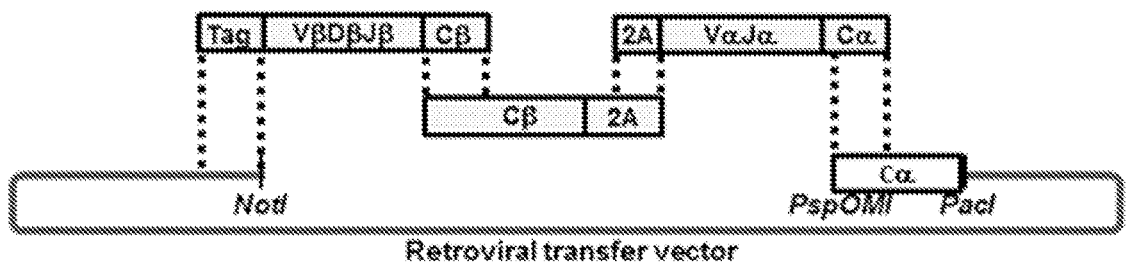
Figure 1

B

1. Comparison of Natural and PspOMI-modified Cα sequences

Natural TCR Cα sequence
5'-TGACCCTGCCGTGTACCAGTGTACCAGCTGAGAGACTCTAAATCCAGTGACAAGTCTGTCTGCCTATTCACC-3'  SEQ ID NO:121

Modified TCR Cα sequence (PspOMI sequence underlined)
5'-TGACCCTGCCGTGTACCAGTGTACCAGCTGAGAGACTCT<u>GGGCCC</u>TAAATCCAGTGACAAGTCTGTCTGCCTATTCACC-3'  SEQ ID NO:122

2. Double-strand DNA fragment before assemble reaction (complementary sequences underlined)

TCR fragment 3' end
5'-TGACCCTGCCGTGTACCAGTGTACCAGCTGAGAGACTCTAAATCCAGTGACAAGTCTGTCTGCCT-3'  SEQ ID NO:123
3'-ACTGGGACGGCACATGGTCACTCTGAGATTTAGGTCACTGTTCAGACAGACGGA-5'  SEQ ID NO:124

Vector 5' end after PspOMI treatment
5'-GGGCCCTAAATCCAGTGACAAGTCTGTCTGCCTATTCACC-3'  SEQ ID NO:125
3'-GAGATTTAGGTCACTGTTCAGACAGACGGATAAGTGG-5'  SEQ ID NO:126

3. Double-strand DNA fragment during assemble reaction (complementary sequences underlined)

TCR fragment 3' end after 5' Exonuclease reaction
5'-TGACCCTGCCGTGTACCAGTGTACCAGCTGAGAGACTCTAAATCCAGTGACAAGTCTGTCTGCCT-3'  SEQ ID NO:127
3'-ACTGGGACGGCACATGGTCACTCT-5'  SEQ ID NO:128

Vector 5' end after 5' Exonuclease reaction
5'-ATTCACC-3'  SEQ ID NO:129
3'-GAGATTTAGGTCACTGTTCAGACAGACGGATAAGTGG-5'

4. Double-strand DNA fragment after assemble reaction (complementary sequences are underlined)

5'-TGACCCTGCCGTGTACCAGTGTACCAGCTGAGAGACTCTAAATCCAGTGACAAGTCTGTCTGCCTATTCACC-3'  SEQ ID NO:121
3'-ACTGGGACGGCACATGGTCACTCTGAGATTTAGGTCACTGTTCAGACAGACGGATAAGTGG-5'  SEQ ID NO:131

Figure 6 (cont.)

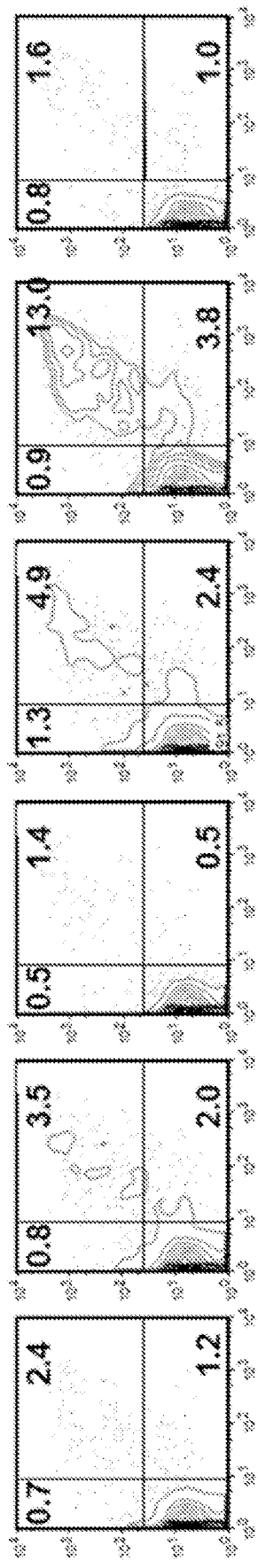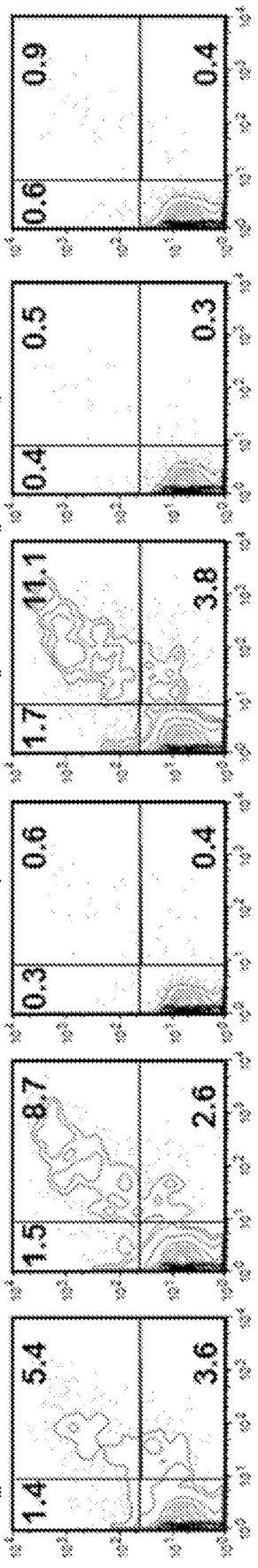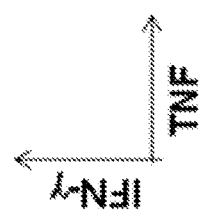
Figure 8

1. Reverse transcription by a reverse transcriptase using a oligo-dT, random, or TCR gene-specific primer

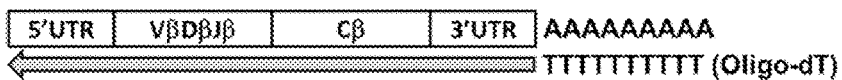

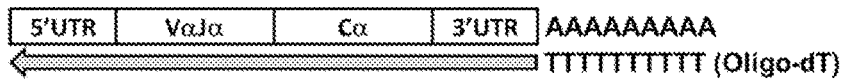

2. Second-strand cDNA synthesis using multiplexed primers

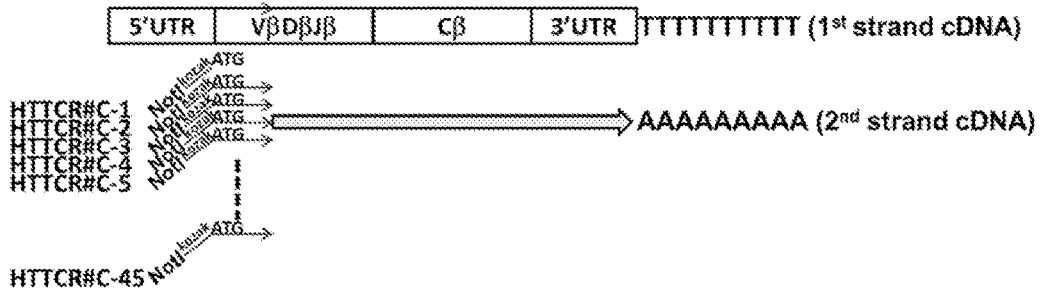

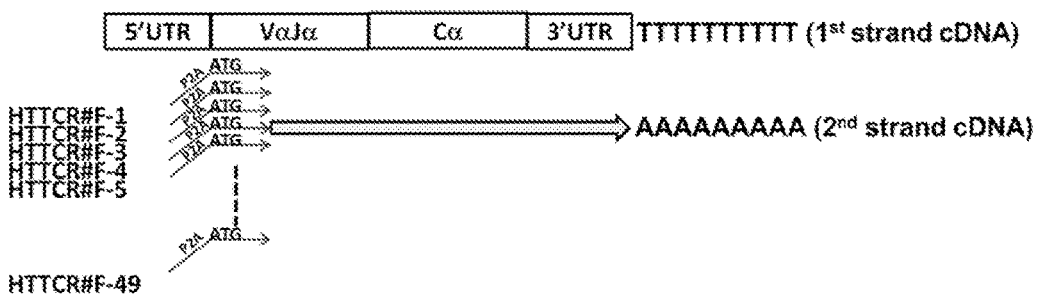

3. Treat with Exonuclease I to destroy excess primers and single-stranded cDNA

4. PCR using tag-specific forward and constant region-specific reverse primers

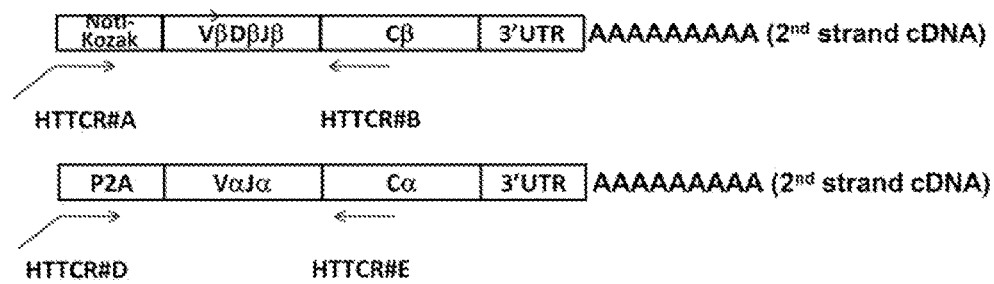

5. Mix VDJβ and VJα fragments with Cβ fragment (prepared separately as a stocked fragment) and clone into a destination TCR-cloning vector using NEBuilder HiFi DNA Assembly cloning kit

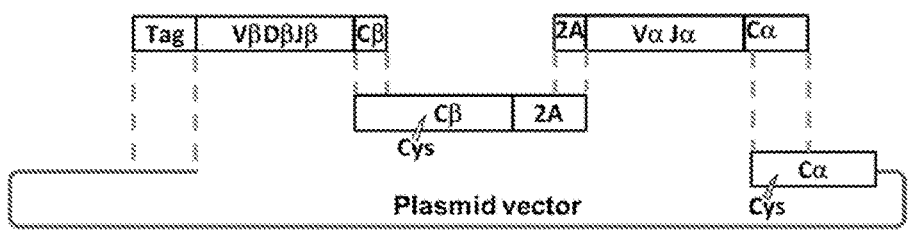

Figure 13

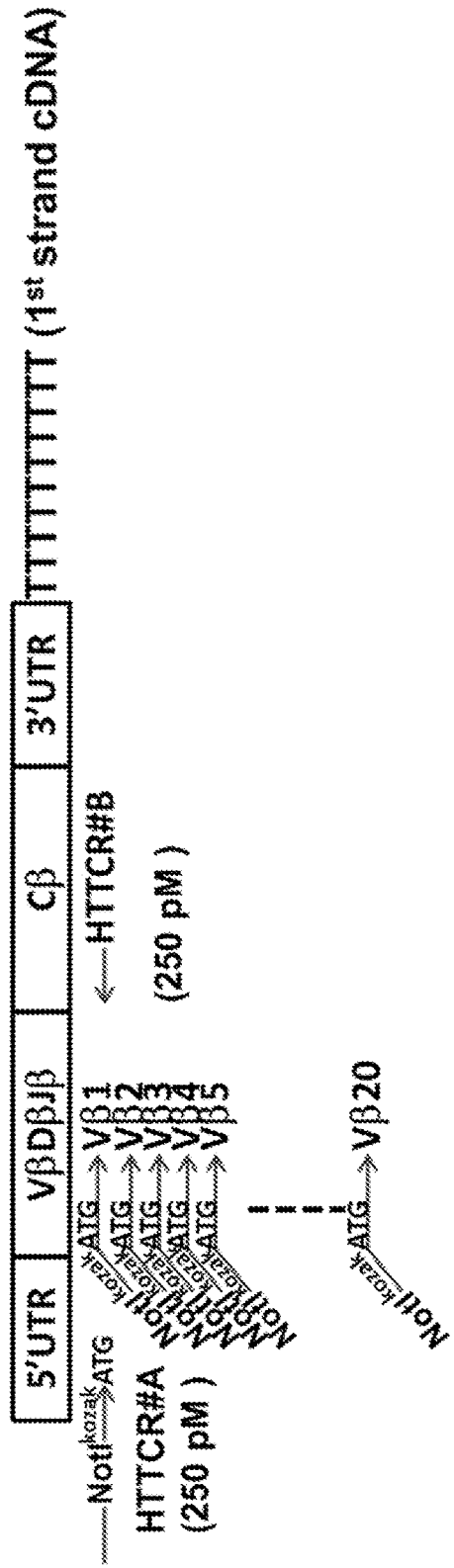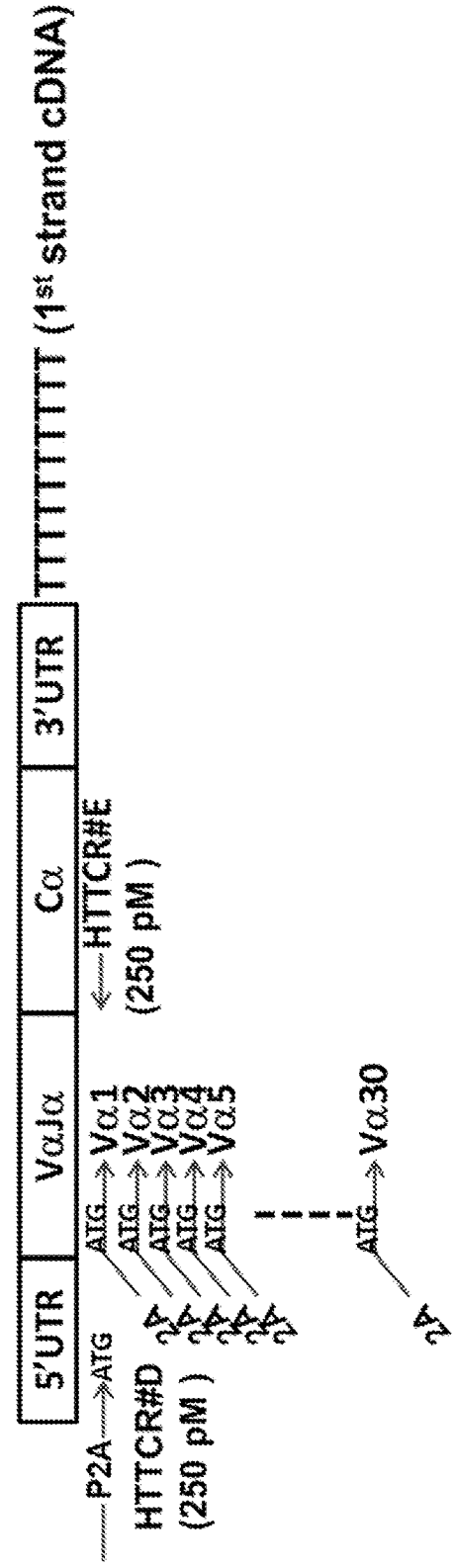
Figure 15

COMPOSITIONS AND METHODS FOR RAPID CLONING OF T-CELL RECEPTORS

CROSS REFERENCE TO RELATED APPLICATIONS

This application claims priority to U.S. provisional application No. 62/369,321, filed on Aug. 1, 2016, the disclosure of which is incorporated by reference.

SEQUENCE LISTING

The instant application contains a Sequence Listing which has been submitted electronically in ACSII format and is hereby incorporated by reference in its entirety. Said ASCII copy, created on Aug. 1, 2017, is named 003551.00787-Masa_TCR_ST25.txt, and is 23,700 bytes in size.

FIELD

The present disclosure relates generally to compositions and methods for rapidly cloning and characterizing T cell receptors.

BACKGROUND

Tumor antigen-specific T cells recognize cancer targets via heterodimeric T-cell receptors (TCR) that recognize tumor antigen-derived peptides loaded on major histocompatibility complex (MHC) molecules on cancer cells. Highly diverse sequences in both TCR α and β chains, especially in their complement-determining region 3 (CDR3), determine MHC restriction and peptide-specificity. Adoptive transfer of autologous tumor antigen-specific T cells into cancer patients is a promising therapeutic strategy for treatment of cancer patients. To overcome the challenge posed by the limitations of expanding large numbers of autologous tumor antigen-specific T cells from patients, gene-engineering of peripheral bulk T-cell population with tumor antigen-specific TCR gene has been developed. It has been widely demonstrated that TCR gene-engineered T cells have comparable anti-tumor effects as the parental T-cell clones against cancer targets. Clinical trials testing TCR gene-engineered T cells have demonstrated feasibility, safety and therapeutic effects in multiple tumor types. However, only a limited number of therapeutic anti-tumor TCR genes have been developed, which limits the broad application of this powerful therapeutic strategy to cancer patients.

Traditionally, tumor antigen-specific TCR α and β chain genes are obtained from well characterized tumor antigen-specific T-cell clones expanded in vitro. However, establishing tumor antigen-specific T cell clones targeting a broad array of tumor antigens and MHC restriction elements is laborious and technically challenging in a high throughput manner. Recently, single-cell approaches such as single-cell PCR (G. C. Wang, P. et al. Sci. Transl. Med. 4, 128ra142 (2012); E. Kobayashi, et al. Nat. Med. 19, 1542-1546 (2013); S. Seitz, et al. Proc. Natl. Acad. Sci. USA 103, 12057-12062 (2006); G. Dossinger, et al. PLoS One 8, e61384 (2013); A. Han, J et al. Nat. Biotechnol. 32, 684-692 (2014)) and emulsion PCR (M. A. Turchaninova, et al. Eur. J. Immunol. 43, 2507-2515 (2013); D. J. Munson, et al. Proc. Natl. Acad. Sci. USA 113, 8272-8277 (2016)) have successfully identified tumor antigen-specific TCR pairs. However, obtaining high-quality anti-tumor T-cells from cancer specimens requires collection and processing of relatively large amounts of surgical specimens, which may not be feasible in all patients. Alternatively, next generation sequencing (NGS) has been utilized to identify paired TCR α and β chain sequences from tumor specimens (C. Linnemann, et al. Nat. Med. 19, 1534-1541 (2013); A. Gros, et al. Nat. Med. 22, 433-438 (2016); A. Pasetto, A et al. Cancer Immunol. Res. 4, 734-743 (2016); B. Howie, et al. Sci. Transl. Med. 7, 301ra131 (2015)). In this method, nearly complete sets of TCR α and β sequences for tumor-infiltrating T cells are obtained, and pairing of TCR α and β chain genes is predicted based on matched frequencies in each specimen. However, estimating absolute frequencies for TCR genes is still challenging with this approach because a significant proportion of T cells express two TCR α chain genes (Padovan, et al. Science 262, 422-424 (1993)). Moreover, in both single cell- and NGS-based approaches, end-point results are often paired TCR gene sequences for many candidate pairs. Multiple laborious procedures such as synthesizing the TCR-expressing cassettes, cloning in expression vectors and testing reactivity against target antigens are then required to identify candidate therapeutic TCR genes. Altogether, rapid identification of tumor-reactive TCR genes for personalizing adoptive T cell therapy remains a major challenge. Thus, there is an ongoing and unmet need for improved methods for rapid identification of tumor-reactive TCR genes. The present disclosure is pertinent to this need.

BRIEF SUMMARY OF THE DISCLOSURE

The present disclosure provides methods, compositions, recombinant DNA molecules, and kits for cloning TCRs. In particular, the disclosure provides a novel method to construct a TCR expression library from biological samples containing antigen-specific T cells, including but not limited to tumor biopsies, including frozen tumor biopsies. TCR-expressing cassettes were constructed and cloned in a retroviral plasmid vector within 24-hours by unbiased PCR amplification of TCR α and β chain variable regions assembled with TCR constant regions. The method was successfully validated by constructing TCR-expressing vectors from tumor antigen-specific T-cell clones and functional assessment of TCR gene-transduced T cells. This method was applied to frozen ovarian tumor specimens that were infiltrated by tumor antigen-specific T cells. A tumor-derived TCR library was expressed on peripheral T cells from healthy volunteers for the screening of tumor antigen-specific TCR pairs by using a MHC/peptide tetramer reagent. A single round of screening identified functional tumor antigen-specific TCR pairs. Peripheral T cells that were engineered with library-derived TCR gene showed potent therapeutic anti-tumor effect in a tumor xenograft model. The presently provided method can therefore efficiently and rapidly provide tumor-specific TCR-expressing viral vectors for the manufacture of therapeutic anti-tumor T-cell products in a personalized manner.

In certain embodiments the disclosure provides compositions and methods for cloning a plurality of TCR α and β chain variable sequences from T-cell TCRs from any biological sample that contains T cells. In embodiments, the disclosure is pertinent to cloning TCR α and β chain variable sequences from oligoclonal populations of T cells. In certain implementations, the oligoclonal populations of T cells comprise T cells that can recognize an antigen expressed by cancer cells, wherein the antigen is associated with a malignant phenotype. In one approach the disclosure comprises: obtaining RNA from T cells, such as from an oligoclonal population of T cells, wherein the RNA comprises mRNA encoding TCR α and chain variable sequences, and generating first single strand cDNA from the mRNA, wherein the first single strand cDNA includes single stranded cDNA encoding the TCR α chains and single stranded cDNA encoding the TCR β chains, wherein the single stranded cDNAs are generated using reverse transcription and oligo-dT primers, to obtain a sample of first strand cDNA amplified from the mRNA. The sample comprising first strand cDNA amplified from the mRNA encoding the TCR α and β chain variable sequences is divided such that there are at least two samples containing the first strand cDNAs. In an embodiment, the sample of first strand cDNA amplified from the mRNA from is divided into first and second samples (which may simply comprise taking an aliquot from the first strand cDNA synthesis reaction and placing it into a separate container), and PCR reactions on the first and second samples are performed to obtain double stranded cDNAs. In an embodiment, in the first sample a second-strand cDNA synthesis is performed to obtain double stranded cDNAs encoding the TCR β chains. This is performed using all or a subset of the primers termed HTTCR#C-1 through HTTCR#C-45 in Table 1 (i.e., using all 45 primers, or a subset of these primers). In the second sample a second-strand cDNA synthesis is performed to obtain double stranded cDNAs encoding the TCR α chains using all or a subset of the primers HTTCR#F-1 through HTTCR#F-49 in Table 1 (i.e., using all 49 primers, or a subset of these primers). Subsequent to obtaining the double stranded cDNAs, which may comprise sequences encoding a plurality of distinct TCR α and β chain variable sequences, the first and second samples are exposed to an exonuclease for a period of time sufficient to degrade primers that were not incorporated into the amplicons, and to degrade single stranded cDNA if present. The exonuclease is then inactivated by, for example, using a heat treatment. Subsequent to exonuclease treatment (if performed), the method involves in the first sample performing a PCR amplification of the amplicons encoding the TCR β chains using tag-specific primer HTTCR#A-ACTTAAGCTTGGTACCGAGCTCG-GATCTGCGGCCGCCACCATG (SEQ ID NO:1) and primer HTTCR#B-CT-CAAACACAGCGACCTCGGGTGGGAACAC (SEQ ID NO:2) to obtain amplicons encoding the TCR β chains, wherein the amplicons encoding the TCR β chains may further comprise one or a combination of a restriction endonuclease recognition site, a Kozak sequence and a translation initiating ATG sequence. The method includes performing in the second sample a PCR amplification of the amplicons encoding the TCR α chains using tag-specific primer HTTCR#D GGAGACGTG-GAAGAAAACCCCGGTCCCATG (SEQ ID NO:48) and HT-TCR#E AGGCAGACAGACTTGTCACTGGATT-TAGAG (SEQ ID NO:49) to obtain amplicons encoding the TCR α chains, wherein the amplicons may further comprise a P2A sequence and an initiating ATG sequence.

The method then involves assembling the amplicons encoding the TCR β chains and the TCR α chains into DNA vectors to provide a plurality of DNA vectors each comprising DNA segments encoding only one of the TCR β chains and only one of the TCR α chains. Thus the vectors can encode distinct TCR β and TCR α chain pairs that were not expressed together by any of the T cells in the sample used as the starting material for the cloning process. In embodiments, TCR β and TCR α chain may be connected by a DNA linker fragment such as 2A-translational skipping site fragment. In embodiments, the assembly of the chains can be performed by, for example mixing the amplicons encoding the TCR β and TCR α chains with one or two DNA fragments, such as with a common or invariable TCR Cβ-2A fragment, or TCR Cβ-2A fragment and TCR Cα fragment. Non-limiting examples of this aspect of the disclosure are illustrated in FIG. 1 step 5 and FIG. 18. Other techniques can also be employed for the vector assembly, including but not necessarily limited to ligation-independent cloning, Gibson assembly cloning, or any similar techniques to assemble the vector that will be recognized by those skilled in the art, given the benefit of this disclosure. Alternatively, the fragments may be assembled as a single fragment comprising the segments encoding the TCR Vβ, cβ, 2A, Vα sequence by overlapping PCR using for example the HTTCR#A β chain-tag-specific forward primer and the HTTCR#E reverse primer. A non-limiting example of this approach is depicted in FIG. 16A.

In embodiments, a plurality of DNA vectors is provided, and each vector in the plurality encodes only a single TCR β chain and a single TCR α chain from the TCRs from T cells. In embodiments, the disclosure uses as a starting material a population of oligoclonal T cells, which may comprise T cells that have infiltrated a tumor. The type of tumor is not particularly limited, and in embodiments includes bladder, brain, breast, ovarian, lung, renal, colon, stomach, pancreas, prostate or liver cancer, myeloma, a sarcoma, a tumor formed from leukemia, lymphoma, or a melanoma. In embodiments, the sample used as a starting material comprises cancer cells that express immunogenic tumor antigens, non-limiting examples of which comprise NY-ESO-1, WT1, MUC1, LMP2, HPV E6 and E7, EGFRvIII, HER2/neu, MAGE-A3, p53, NY-ESO-1, PSMA, GD2, CEA, MalanA/MART1, mutated Ras, gp100, Proteinase 3, bcr-abl, Tyrosinase, Survivin, PSA, hTERT, MAGE-A1, MAGE-A4, MAGE-C1, MAGE-C2, PLAC1, Sp17, TRP-2, Cyclin B1, Mesothelin, Folate Receptor alpha, and patient specific neoantigens. In embodiments DNA vectors made by a process of this disclosure are capable of expressing the TCR α and the TCR β chains in lymphocytes such that the lymphocytes exhibit antigen specificity against an antigen expressed by a cancer cell.

The disclosure includes introducing into lymphocytes at least one of the DNA vectors and allowing expression of the TCR β chain and the TCR α chain encoded by the at least one vector such that the lymphocytes express a functional TCR comprising the TCR β chain and the TCR α chain. The disclosure includes determining whether or not the lymphocytes exhibit antigen specificity against an antigen expressed by cancer cells. The disclosure also includes cell of any type, including lymphocytes that comprise at least one DNA vector made according to any method of this disclosure. Such lymphocytes can recognize any cancer cell type and any antigen that is the same as the cancer cell types and antigens that T cells in the starting material sample can recognize. Such lymphocytes may have also exhibit improved antigen recognizing properties.

The disclosure also provides kits that contain combinations of primers described herein, as well as reagents for performing the methods of this disclosure, such as a destination vector(s) comprising a suitable restriction endonuclease recognition sequences, and a segment encoding a cysteine-modified Cα fragment. The reagents may also include one or more buffers for performing first strand cDNA synthesis, and/or second strand cDNA synthesis, and for example, a reverse transcriptase and/or a DNA polymerase.

DESCRIPTION OF THE DRAWINGS

FIG. 1. Amplification of TCR genes and cloning into retroviral plasmid vectors. (A) Schematic representation of the TCR-expressing cassette. Abbreviations used are: LTR, long terminal repeats; ψ, packaging signal; SA, splice acceptor site; and WRE: Woodchuck hepatitis virus posttranscriptional regulatory element. (B) TCR amplification and cloning procedures. Detailed procedures are described in Examples. Steps 1-4 were shown only for TCR chain for simplicity. For α chain, steps 2-4 are performed in a separate tube using different primers: HTTCR#F in step 2 and HTTCR#D and #E in step 4. The sequence of the oligo dT segment is SEQ ID NO:120. Combined TCR β chain and TCR α chain synthesis are shown in FIG. 13. The sequence of the Oligo-dT is SEQ ID NO:132.

FIG. 8. Recognition of naturally processed NY-ESO-1 by MHC class II-restricted NY-ESO-1-specific TCR-expressing T cells. NY-ESO-1-specific TCR-expressing retroviral vectors were constructed from 5 NY-ESO-1-specific CD4+ T-cell clones: SB, JM, 3B5, 5B8, and PB-T. Polyclonally activated T cells from healthy donor PBMC were transduced by retroviral vectors and co-cultured for 6 hours with the indicated MHC class II-expressing cancer cell line that expressed NY-ESO-1 or were pulsed with NY-ESO-1 protein in the presence of monensin. Intracellular IFN-γ and TNF-α were stained following cell surface CD4 staining. Staining of cells gated on CD4 is shown.

FIG. 13. Amplification of TCR genes and cloning into retroviral plasmid vectors as an expanded version of FIG. 1 to include TCR α chain synthesis.

FIG. 15. Alternative method to amplify TCR variable chain fragments using multiplexed primers when the sample is single T-cells or T-cell clones. This method is not suitable for use with oligoclonal T-cell samples.

DETAILED DESCRIPTION

Figure 2:
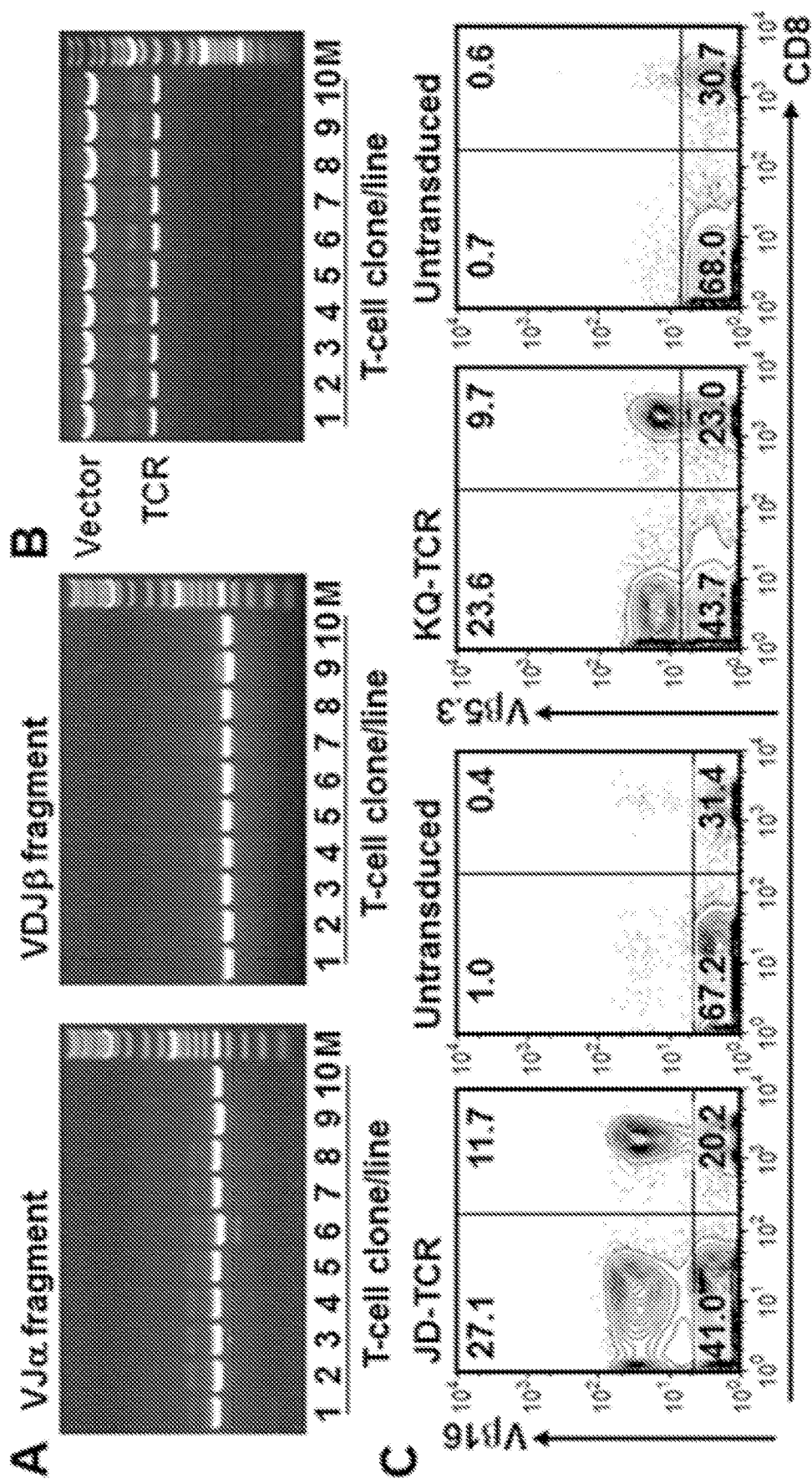
FIG. 2. Construction of TCR-expressing retroviral vectors from tumor antigen-specific T-cell clones. (A) Amplification of VJα and VDJβ fragments. PCR amplification of TCR gene was performed as depicted in FIG. 1B and the product was electrophoresed on an agarose gel and visualized by ethidium bromide. Lanes 1-4: NY-ESO-1-specific CD8+ T-cell clones; lanes 5-9: NY-ESO-1-specific CD4+ T-cell clones; and lane 10: Jurkat T lymphoma cell line. (B) Excision of TCR-expressing cassette from the bulk plasmid vector. Bulk plasmid was obtained from pooled *E. coli* colonies and digested with NotI and PacI restriction enzymes. (C) Expression of TCR transgene after retroviral transduction. Bulk plasmids were used for production of retroviral particles. Polyclonally activated T cells that were transduced by retroviral vectors were stained by Vβ subtype-specific antibodies. (D) Binding of TCR gene-transduced T cells to a specific MHC/peptide tetramer. HLA B*35-restricted NY-ESO-1 (94-102) peptide-specific KQ-TCR and HLA A*02-restricted NY-ESO-1 (157-165) peptide-specific JD-TCR transduced T cells were stained with the corresponding tetramers and analyzed by flow cytometry. (E) Recognition of NY-ESO-1-expressing cancer cell lines. TCR gene-transduced T cells were co-cultured with cancer cells for 6 hours in the presence of Monensin. Expression of IFN-γ and TNF-α was examined by intracellular staining.
Figure 2:
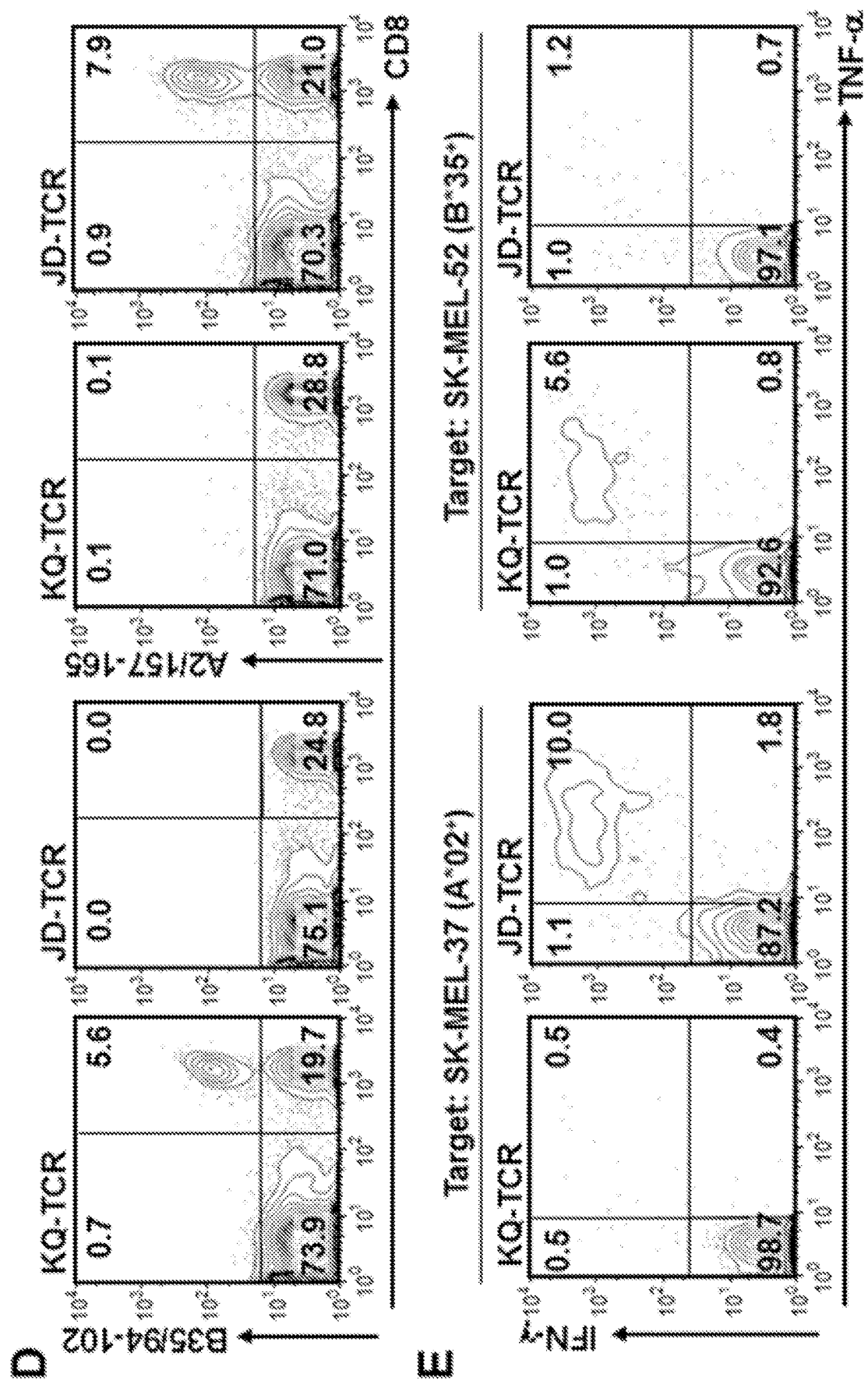

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure relates generally to adoptive transfer of autologous tumor antigen-specific T cells, which is an effective therapeutic treatment for cancer patients. Gene-engineering of patients' peripheral T cells with tumor antigen-specific TCR or chimeric antigen receptor (CAR) gene is a practical approach to overcome challenges in obtaining sufficient numbers of tumor antigen-specific T cells from patients' specimens. In solid tumors, because most known tumor-specific antigens are intracellular proteins, such as cancer-testis antigens, TCR rather than CAR genes may be more suitable for manufacture of therapeutic T-cell products. However, because of a wide variety of HLA types and tumor antigen expression patterns, a large panel of TCR genes specific for different tumor antigens and HLA restriction elements are required for treatment of wide population of patients with different tumor types. The present disclosure relates to the discovery of tumor antigen-specific TCR α and chain pairs, and provides a rapid method to construct randomly paired TCR-expression library from tumor tissues that are infiltrated by tumor antigen-specific T cells. In contrast to other methods that require single cell suspension, the current method only requires snap frozen tumor specimens, which can be prepared at most clinical sites, although it is applicable to freshly obtained samples. As described in more detail below, following total RNA extraction and reverse transcription, variable regions of TCR α and β chains were amplified by common primers, but not TCR Vα or Vβ-specific multiplexed primers, in order to minimize PCR bias. These variable fragments were assembled as expression cassettes using a highly efficient cloning platform. Through the compositions and methods provided by the present disclosure, a tumor-infiltrating T cell-derived TCR library can be prepared as retroviral expression plasmids within 24-hours, as outlined in FIG. 20. We then retrovirally transduce the TCR library into peripheral T cells, in order to screen relevant tumor antigen-specific TCRs. We successfully identified tumor antigen-specific TCR pairs from 2 out of 3 frozen ovarian tumor specimens after a single round of screening. Importantly, the TCRs obtained by this unique approach were functional as evidenced by in vitro tumor recognition. Moreover, we demonstrated the therapeutic potential of the library-derived TCRs by adoptively transferring the T cells in a tumor xenograft model.

The robustness of the present approach is demonstrated by the ability to identify tumor-reactive TCRs despite the relatively low frequencies of T cells infected by tumor-derived TCR-expression library at suboptimal viral titers. Interestingly, one of the tumor-derived library (tumor #1) did not contain significant fraction of tumor-reactive TCRs, although the original tumor specimen contained high frequency tetramer-reactive CD8+ T cells. It is possible that the specimen that was used for single cell suspension for T-cell staining and that for RNA extraction contained different fractions of tetramer-reactive T cells. Alternatively, tetramer-reactive T cells could be composed of oligoclonal populations, for which the probability to form functional TCR pairs in the library exponentially decreases. In the present disclosure, a library ($3\times10^5$) was used to perform screening. This library size is considered to be sufficient to obtain correct TCR pairs from a T-cell clone of more than 1% frequency among total T cells, and given the benefit of this disclosure, the library size could be easily expanded by the use of electro-competent cells to identify specific TCR pairs from less frequent T-cell clones.

It is known that randomly paired libraries of immunoglobulin heavy and light chains have been used to identify novel antibodies against therapeutic targets including cancer (D. Sanchez-Martin, et al. Trends Biotechnol. 33, 292-301 (2015)). In general, immunoglobulin heavy and light chains are PCR-amplified and randomly fused via a linker peptide to generate single chain variable fragments. Then, pairs with desired specificity are isolated by screening of library for binding to the target antigens. However, this method has not been used to identify antigen-specific TCR heterodimer genes. The results of this disclosure for the first time demonstrate that a tumor-derived randomly paired TCR library is a useful resource to efficiently identify tumor antigen-specific TCR pairs. In addition, we were able to quickly and directly generate viral vector constructs containing the new TCRs, which not only speeds-up the screening process, but provides an effective tool to genetically engineer T cells for adoptive transfer studies. In contrast to other methods to obtain paired TCR α and β chain sequences from a single cell by single-cell PCR, emulsion PCR, or the pairSEQ platform, the present approach generated artificial TCR pairs that recognized cancer targets with extremely high affinity in comparison to the natural tumor antigen-specific TCR pair. However, it has been known that artificial TCR pairs have a potential to cross-react against other antigens including those highly expressed in normal tissues. Off-target toxicity of TCR gene-engineered T cell product is a serious problem in identification of high affinity non-natural TCRs as found in an affinity enhanced TCR or a murine TCR. For clinical applications, although testing off-target reactivity is important for any therapeutic TCR gene, candidates for therapeutic TCR genes identified by the current method can be more extensively tested for cross-reactivity against a panel of normal tissues and genes that contain homologous sequences of the TCR epitope. Thus, the present disclosure establishes a new and fast method for discovery and identification of relevant TCRs that can be directly utilized in a viral vector construct form for downstream translational validation towards an effective therapeutic adoptive cell therapy for cancer.

In more detail, the present disclosure relates generally to compositions and methods for use in rapid cloning of TCRs, and methods for producing recombinant TCRs, such as a library of TCRs. As used in this disclosure, a "recombinant TCR" means a TCR that is encoded by and capable of being expressed from a polynucleotide that is introduced into a cell, meaning prior to the introduction of the polynucleotide the TCR was not encoded by a chromosomal sequence in the cell.

This disclosure includes each and every polynucleotide sequence disclosed herein, and all combinations and all sub-combinations of the distinct sequences. In certain embodiments, compositions and methods provided by this disclosure include oligonucleotide primers, and thus can include a primer component. In certain aspects the primer component of this disclosure comprises or consists of any combination of the primer sequences, wherein the primer sequences are selected from the sequences that are presented in the Table of this disclosure. The disclosure includes all cloning steps, and all cloning intermediates, including but not necessarily to primers annealed to RNA and/or DNA, fully and partially double stranded amplicons, restriction digests and fragments thereof, including fragments that are blunt ended or have 5' or 3' single stranded overhangs, linearized plasmids, overlapping primers, and the like. Certain steps of the methods described herein can be performed sequentially, or concurrently, and can be performed in single or separate reactions, as will be apparent from the description of particular embodiments and the figures.

As will be described in more detail below and by way of the Figures of this disclosure, methods are provided for amplifying TCR coding sequences from populations of mammalian cells, such that the TCR coding sequences can be incorporated into expression vectors that encode and express functional TCRs. Thus, the disclosure relates to cloning, expression, and functional characterization of TCRs that are expected to be useful in development of, and use in, therapeutic approaches applicable to a wide variety of conditions. Thus the disclosure pertains to the identification and cloning of TCRs that are useful for generating T-cells that are programmed to have specificity for a desired antigen, and wherein the TCRs are compatible with the HLA type of any given individual.

Figure 11:
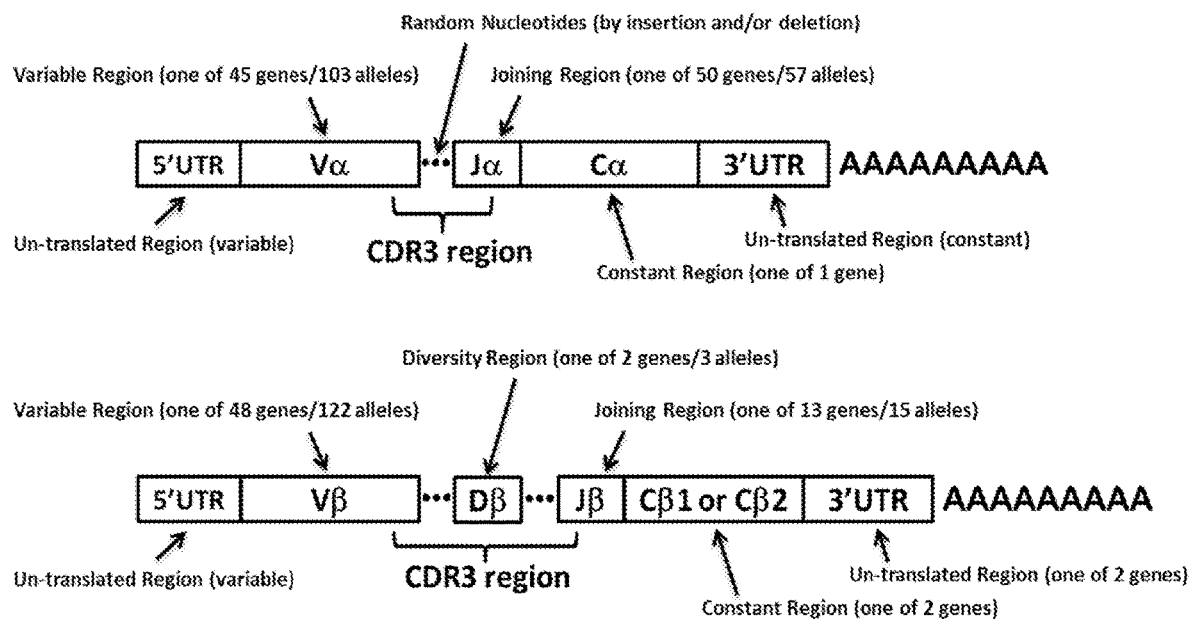
FIG. 11. Structure of TCR α and β chain mRNA. During recombination of Vα and Jα, and Vβ, Dβ, and Jβ, nucleotides are randomly inserted or deleted at junctions, which results in extremely high diversity in the CDR3 region.

In general, the method comprises subjecting a population of mammalian cells comprising or consisting of T cells to a polynucleotide extraction step, amplifying TCR coding regions from the extracted polynucleotides, modifying the amplified polynucleotides such that they are suitable for incorporation into a recombinant vector, and incorporating the polynucleotide sequences encoding at least TCR α and β chain coding sequences into a recombinant expression vector. The incorporated sequences can accordingly comprise a combination of Vβ, Dβ, Jβ, sequences, constant regions (i.e., a β chain constant region and a α chain constant region), and a Vα and Jα region, as well as other sequences. The expression vector(s) is accordingly configured to express recombinant TCR polypeptides that were amplified from population of cells obtained from one or more individuals. A non-limiting illustration of a PCR amplification template of this disclosure is provided by FIG. 11, which depicts a TCR α and β chain mRNA.

The type of cells that provide the starting material for the TCR cloning process of this disclosure are not particularly limited, provided that at least some cells that are subjected to the cloning procedure include cells that encode TCRs. In this regard the disclosure includes rapid TCR cloning approaches that are suitable for use with biological samples comprising T cells obtained from any mammal, including humans and non-human mammals, and is therefore expected to be suitable for identifying native TCR sequences, and generating recombinant TCRs that can be used in human and veterinary therapeutic implementations. The biological sample can be any biological sample that would be expected to contain T cells, including but not necessarily limited to liquid biological samples, such as blood lymph or bone marrow, and solid biological samples of, for example, lymph nodes, spleen, tumors, or thymus.

In certain embodiments the method is performed on a population of cells that are obtained from an individual, wherein the population is expected to include T cells that comprise and/or encode a TCR α and a TCR β chain. The population may also include T cells that include γδ T cells, but the γδ TCR will not be detected using the methods of this disclosure. In certain embodiments, the cells that are used for the TCR cloning procedure of this disclosure can comprise peripheral blood mononuclear cells (PBMCs) and thus may comprise T cells, B cells, natural killer cells, natural killer T cells, and monocytes. The T-cells may be a mixture of T cell types or single cells, which include but are not necessarily limited to CD4+ T cells and CD8+ T cells. Thus the T cells may be T helper cells ($T_H$ cells), Cytotoxic T cells ($T_C$ cells, or CTLs), suppressor T cells, such as CD4$^+$ $T_{reg}$ cells, or naïve, stem cell memory, effector, memory, intra-epithelial, or tissue-resident memory T cells. In alternative embodiments, the cells may be a partially or fully purified population of cells, or T cell clones that can be obtained using established techniques, such as by cell sorting or by cell culture.

Figure 12:
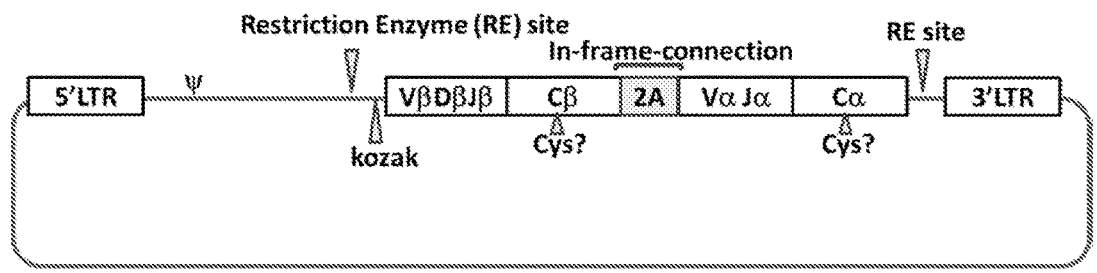
FIG. 12. Example of expression vector and modifications of TCR expression cassette. This example is shown for a retroviral plasmid vector. Restriction enzyme sites provides a cloning site for TCR insert. Kozak sequence, which is generally defined as GCCRCC where R is A or G, enables efficient translation. TCR α and β chains are connected by 2A translational skipping site including F2A, E2A, T2A, or P2A, which enables stoichiometric expression of two chains. Alternatively, other sequences such as internal ribosomal entry site (IRES), can be used. The constant regions (Cα and Cβ) can be modified to include a cysteine residue to enhance pairing of expressed TCR α and β chains by forming a disulfide bond.

With respect to the expression vectors generated using methods of this disclosure, at least some of them will encode functional TCRs which comprise a TCR α and a TCR β chain, wherein subsequent to expression the two chains are present in a physical association with one another (e.g., in a complex) and are non-covalently joined to one another, or wherein the two chains are distinct polypeptides but are covalently joined to one another, such as by a disulfide or other covalent linkage that is not a peptide bond, or wherein the two chains are connected by a polypeptide linker, i.e., a single chain TCR. In other embodiments, two polypeptides that constitute the TCR α and a TCR β chain can both be included in a single polypeptide, such as a fusion protein. In certain embodiments, the fusion protein comprises a TCR α chain amino acid sequence and a TCR β chain amino acid sequence that have been translated from the same open reading frame (ORF), or distinct ORFs, or an ORF that contain a signal that results in non-continuous translation. In one embodiment, the ORF comprises a 2A-mediated translation skipping site positioned between the TCR α and TCR β chain. Constructs for making 2A containing proteins (also referred to as 2A Peptide-Linked multicistronic vectors) are known in the art. (See, for example, *Gene Transfer: Delivery and Expression of DNA and RNA, A Laboratory Manual*, (2007), Friedman et al., International Standard Book Number (ISBN) 978-087969765-5). Briefly, 2A peptide sequences, when included between coding regions, allow for stoichiometric production of discrete protein products within a single vector through a novel cleavage event that occurs in the 2A peptide sequence. 2A peptide sequences are generally short sequence comprising 18-22 amino acids and can comprise distinct amino-terminal sequences. Thus, in one embodiment, a fusion protein of the invention includes a P2A amino acid sequence. In embodiments, a fusion protein of the invention can comprise a linker sequence between the TCR α and TCR β chains. In certain embodiments, the linker sequence can comprise from 3-30 amino acids, inclusive. In embodiments, the linker sequences comprises a GSG (Gly-Ser-Gly) linker or an SGSG (Ser-Gly-Ser-Gly) (SEQ ID NO:118) linker. In certain embodiments, the TCR α and TCR β chains are connected to one another by an amino acid sequence that comprises a furin protease recognition site, such as an RAKR (Arg-Ala-Lys-Arg) (SEQ ID NO:119) site. A non-limiting example of an expression vector that can be made using the rapid cloning approaches of this disclosure is shown in FIG. 12, which relates to FIG. 1, step 5.

In one embodiment, the expression construct that is made using the rapid cloning methods of this disclosure encodes a TCR and may also include additional or alternative polynucleotides. The additional polynucleotides can be such that they enable cloning of TCR into expression plasmids, for example restriction enzyme sites or overlapping sequences with plasmids. The additional polynucleotides can be such that they enhance expression of TCR, for example the Kozak consensus sequence. The additional polynucleotides can be such that they enhance formation of TCR heterodimer complex, for example cysteine modifications in the TCR constant regions. The additional polynucleotide can be such that they enable identification of TCR expressing cells, such as by adding a short tag sequence detected by antibodies such as c-Myc, V5, or poly-histidine or by encoding a detectable marker, such as a fluorescent or luminescent protein. The additional polynucleotides can be such that they encode an element that allows for selective elimination of TCR expressing cells, such as a thymidine kinase gene.

In one aspect the disclosure provides a method that is applicable to rapid cloning of TCRs from single cells/T cell clones, and is also applicable to rapid cloning of TCRs from oligoclonal T cells. An "oligoclonal population of T cells" as used herein means a plurality of distinct T cells wherein each T cell in the plurality has a distinct TCR, and wherein the plurality of distinct T cells has in common antigenic agent that comprises at least one antigen that can be recognized by at least some T cells in the population. Antigenic agents as such may comprise pathogens, including but not limited to pathogenic microorganisms and viruses, and mammalian proteins and other antigenic determinants. For example, cancer cells may be antigenic agents that express one or more cancer antigens that can be recognized either directly by at least some of the T cells in the oligoclonal population, or can be recognized when presented to the T cells by other cells such as dendritic cells in the context of, for example, a major histocompatibility complex (MHC), i.e., in the context of human leukocyte antigen (HLA).

In one embodiment an oligoclonal population of T Cells can be obtained from a tissue sample. In an embodiment the tissue sample comprises a sample of a tumor, wherein the T cells have infiltrated the tumor, the sample thus comprising an oligoclonal population tumor-infiltrating T-lymphocytes. In one embodiment, the disclosure comprises obtaining total RNA from a sample. "Obtaining" RNA can mean taking a sample, or receiving any sample that contains RNA. In embodiments, total RNA or mRNA can if desired be separated from any sample using any of a variety of known approaches. In embodiments, separation of mRNA is not necessary because total RNA, or a cell lysate containing RNA, can be used as starting material for amplification of mRNA encoding TCR RNAs as further described herein. If the sample is of a tumor, the sample can comprise any portion of the tumor, including but not limited to a single or pooled tumor biopsies, whole tumors, samples of primary tumors, metastasized tumors, metastatic foci, and the like. In certain embodiments the disclosure comprises determining TCRs from tumor infiltrating T cells, wherein the tumor is any solid tumor, or a solid tumor formed from, for example, a liquid tumor. In embodiments, the cancer comprise a type of cancer selected from bladder, brain, breast, ovarian, lung, renal, colon, stomach, pancreas, prostate or liver cancer, myeloma, a sarcoma, leukemia, lymphoma, or melanoma. In embodiments, the cancer comprises cancer cells that express one or more immunogenic tumor antigens. The one or more cancer antigens can comprise any of NY-ESO-1, WT1, MUC1, LMP2, HPV E6 and E7, EGFRvIII, HER2/neu, MAGE-A3, p53, NY-ESO-1, PSMA, GD2, CEA, MalanA/MART1, mutated Ras, gp100, Proteinase 3, bcr-abl, Tyrosinase, Survivin, PSA, hTERT, MAGE-A1, MAGE-A4, MAGE-C1, MAGE-C2, PLAC1, Sp17, TRP-2, Cyclin B1, Mesothelin, or Folate Receptor alpha. The cancer can express patient specific neoantigens, i.e., a newly formed antigen that has not been previously recognized by the immune system.

Tumor-infiltrating T cells can be isolated for example by using antibodies for T cells, but isolation of tumor-infiltrating T cells is not compulsory to perform methods of this disclosure. The cancer may be of any stage. There is no particular limit to the individual from whom the sample is obtained, and thus the individual can be a human, a non-human mammal, and can be any age, gender, or ethnicity. Further, the individual may be of any HLA type. The sample can be any size, provided that the sample contains at least one T cell. For example, a single T cell from tumor tissue, or any size sample of tumor tissue can be used in embodiments of this disclosure. In embodiments, a tumor biopsy can be used.

The diversity of TCRs as determined by distinct combinations of specific α chain and β chain variable sequences in an oligoclonal population of T cells of this disclosure can range from, for example, several distinct TCRs, to several hundred-thousand distinct TCRs. The disclosure thus comprises determining at least one distinct TCR, and up to one hundred thousand TCRs, or more, from an oligoclonal T cell population.

In one aspect the disclosure comprises obtaining a sample of a tumor from an individual, separating T cells from the tumor or using the whole tumor tissue, isolating total or mRNA containing TCR-α and β chain coding mRNA from the T cells, producing single stranded and/or double stranded cDNA from the mRNA, cloning the cDNA into a vector, and determining the sequence of the DNA encoding the TCR-α and β chains, and/or determining the amino acid sequence of the TCR-α and β chains. The disclosure includes optionally expressing the TCR-α and β chains recombinantly for, for example, adoptive immunotherapy for an individual who has a type of cancer that expresses an antigen that can be recognized by lymphocytes that express the recombinant TCR. Libraries comprising TCR-encoding polynucleotides obtained from oligoclonal T cell populations are included.

The disclosure also includes cells, such as a plurality of distinct cells and/or cell types, which comprise the recombinant polynucleotides. The cells can be isolated cells, cells grown and/or expanded and/or maintained in culture, and can be prokaryotic or eukaryotic cells or recombinant viruses. Prokaryotic and eukaryotic cell cultures and recombinant viruses can be used, for example, to propagate or amplify the TCR expression vectors of the invention. In embodiments, modified T cells that are engineered to express a TCR identified by methods of this disclosure are tested for specificity for any particular antigen. Thus the disclosure provides for screening, including but not necessarily limited to high-throughput approaches, a plurality of TCRs that are incorporated into expression vectors as described herein. Screening can be based on the capability to bind to the MHC/peptide complex, such as by staining with fluorescent MHC/peptide multimers. Screening can be based on the capability to produce molecules upon binding to the MHC/peptide complex, such as cytokines. TCRs can be expressed on reporter cell lines that are engineered to express fluorescent or luminescent molecules or molecules that are detected by antibodies upon binding to MHC/peptide complex.

Expression vectors for use with embodiments of this disclosure can be any suitable expression vector. In embodiments, the expression vector comprises a modified viral polynucleotide, such as from a retroviral or such as a lentiviral vector.

Figure 18:
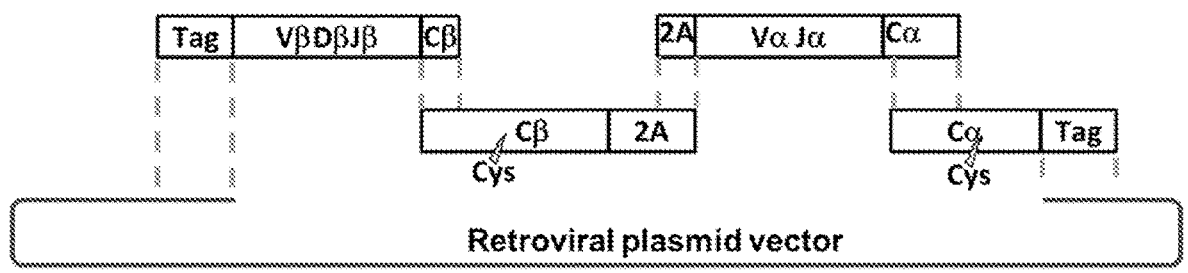
FIG. 18. Alternative method to assemble 4 fragments by ligation-independent cloning. Tag-VβDβJβ-Xβ, Cβ-2A, 2A-VαJα-Cα fragments are obtained as described. Cα-Tag fragment is obtained by PCR amplification using HTTCR#I and HTTCR#J and using template containing this fragment such as the plasmid.

In one approach the disclosure comprises the steps as outlined in FIG. 1 and FIG. 13 namely: 1) obtaining mRNA encoding TCR α and chain variable sequences from a population of T cells, such as a population of oligoclonal T cells from, for example, a tumor sample, and generating single stranded cDNA from the mRNA, including single stranded cDNA encoding the TCR α chains and single stranded cDNA encoding the TCR β chains, wherein the single stranded cDNAs are generated using any suitable reverse transcriptase and, for example oligo-dT primers or any other suitable primers;

2) dividing the cDNA preparation from 1) into two separate reactions (outlined in FIG. 13) and performing second-strand cDNA synthesis to generate in a single cycle DNA polymerase reaction (a first reaction) double stranded cDNA fragments encoding the TCR chains using the primers HTTCR#C-1 through HTTCR#C-45, that can be used as a mixture or independently, as shown in Table 1, and in a second single cycle DNA polymerase reaction (a second reaction) double stranded cDNA fragments encoding the TCR α chains using the primers HTTCR#F-1 through HTTCR#F-49, that can be used as mixture or independently, as shown in Table 1;

3) Subjecting the reactions from step 2) to an exonuclease I, such as DNA Exonuclease I, to degrade unused primers and single stranded cDNA that, for example, is all non-TCR encoding cDNA, followed by heat-inactivation of the nuclease activity;

4) Subjecting the reactions comprising the double stranded cDNA fragments from 3) to i) PCR on the double-stranded cDNA comprising the TCR β chain sequences using the HTTCR#A ACT-TAAGCTTGGTACCGAGCTCGGATCTGCGGCCGC-CACCATG (SEQ ID NO:1) and primer HTTCR#B CTCAAACACAGCGACCTCGGGTGGGAACAC (SEQ ID NO:2) to obtain amplicons encoding the TCR β chains and ii) PCR on the double-stranded cDNA comprising the TCR α chain sequences using HTTCR#D-GGAGACGTG-GAAGAAAACCCCGGTCCCATG (SEQ ID NO:48) and HT-TCR#E AGGCAGACAGACTTGTCACTGGATT-TAGAG (SEQ ID NO:49). Without intending to be constrained by any particular theory it is considered that amplification by a tag-specific primer and common constant region-specific primer minimizes the bias in amplifying multiple TCR species from oligoclonal or polyclonal T-cell populations;

5) Assembling the TCR β chain amplicons and the TCR α chain amplicons from 4) into a vector to provide a vector comprising segments encoding the TCR β chain and the TCR α chain connected by a DNA linker fragment such as 2A-translational skipping site fragment, wherein the assembling is performed by, for example: i) mixing the amplicons with one or two DNA fragments, such as with a common or invariable TCR Cβ-2A fragment or TCR Cβ-2A fragment and TCR Cα fragment as shown in FIG. 1 step 5 and FIG. 18, and using for example ligation-independent cloning, Gibson assembly cloning, or a similar technique to assemble the vector. Alternatively, fragments are assembled as a single fragment comprising the segments encoding the TCR Vβ, Cβ, 2A, Vα sequence by overlapping PCR using for example the HTTCR#A β chain-tag-specific forward primer and the HTTCR#E reverse primer as outlined in FIG. 16A, In embodiments, the disclosure includes using subsets of the primers in Table 1, and in certain implementations includes using subsets of the #C primers, and using subsets of the #F primers. For example, a subset of primers can be selected where a specific Vβ subtype(s) is used by the tumor antigen-specific T cells. In an embodiment, this can be ascertained from, for example, flow cytometry using Vβ or Vα subtype-specific antibodies. In embodiments, the disclosure includes subpools of primer mixes, for example, instead of mixing all the #C primers and mixing all the #F primers, 5 subpools of about 10 primers/each subpool can be used, i.e., primer subpools A,B,C,D,E for alpha and F,G,H,I,J for beta.

In embodiments of this disclosure a common TCR Cβ-2A fragment can be used, and can be prepared by for example, PCR using primers HTTCR#G and HTTCR#H from the template plasmid containing Cβ-2A fragment. Preparation of TCR Cβ-2A fusion fragments by PCR amplification from a template plasmid is shown in FIG. 16C. If the amplicons are mixed with two DNA fragments they can be mixed with, for example, the Cβ-2A fragment and a Cα fragment as shown in FIG. 18 and assembled into a contiguous fragment by, for example, ligation-independent cloning.

Those skilled in the art will recognize that the foregoing steps can all be performed in the case where the T cells are polyclonal or oligoclonal as well as for single T cells and T cell clones, but it is preferable for single T cells and T cell clones (i.e., there is only one TCR species per reaction where PCR bias by multiplexed Vα or Vβ-specific primers is not a concern) to omit step 3 (subjecting the reactions the nuclease treatment), and to combine steps 2 and 4, i.e., there is no need for a nuclease or heat inactivation of unused primers, and the second-strand cDNA synthesis to produce the cDNA amplicons encoding the TCR β chains the cDNA amplicons encoding the TCR α chains (in separate reactions) can be performed concurrently. For example, steps 2 and 4 can be combined for β chain amplification by using all of the HTTCR#A β chain-tag-specific forward primers, the HTTCR#B Cβ-specific reverse primer, and all of the HTTCR#C primers. Likewise, for the α chain amplification, all of the HTTCR#D primers can be used with the HTTRC#E Cα-specific reverse primer, and all of the HTTCR#F primers. All primer concentrations depicted the figures are included in this disclosure. Aspects of the current approach were tested in multiple configurations and conditions, using distinct primer combinations, polymerases and purification methods, yielding more than 10 failed attempts to achieve suitable results.

As described above, in certain embodiments the disclosure includes use of two different destination vectors, one of which is suitable for ligation-independent cloning and the other is suitable for restriction enzyme-ligase cloning. The Cα region which is included in these vectors are modified to introduce restriction enzyme sites, but the sequence after cloning encodes the natural Cα sequence, and thus in certain embodiments the cloning approach is scar-free with respect to the Cα sequence.

In more detail, an expression vector can contain a Cα fragment. To provide a sequence that can cleave a vector at Cα fragment, artificial restriction enzyme site is introduced in the Cα region. In this example, GGGCCC sequence which is recognized by PspOMI (or Bsp120I) enzyme was introduced. A forward (PspOMI—Cα-F) and reverse primers (PspOMI—Cα-R) that contain GGGCCC sequence was designed. Two PCR reactions is performed using unmodified TCR-expression cassette as a template using HTTCR#A and PspOMI—Cα-R, and HTTCR#J and PspOMI—Cα-F. Resulting amplicons are connected by overlapping PCR using HTTCR#A and HTTCR#J and cloned into an expression vector.

Additional Primer Sequence include:

```
PspOMI-Ca-F:
                                        (SEQ ID NO: 99)
ACCAGCTGGGGCCCTCTAAATCCAGTGACAAGTCTGTCTGCC

PspOMI-Ca-R:
                                       (SEQ ID NO: 101)
GAGGGCCCCAGCTGGTACACGGCAGGG
```

Ligation of TCR Vα PCR fragment into PspOMI-treated expression vector is performed using ligation-independent cloning methods such as Gibson Assembly and NEBuilder HiFi DNA Assembly, both of which are available as a kit from New England Biolabs. These methods utilize 5' Exonuclease to create complementary ends between two fragments. 5' Exonuclease destroy 5' overhang produced by PspOMI. As a result, ligation product becomes the natural Cα sequence. Similar ligation-independent cloning methods may use 3' Exonuclease such as InFusion cloning which is available from Clontech. In this case, ApaI, which recognizes the same GGGCCC sequence but produces 3' overhang, may be used.

In another approach, the disclosure provides a vector and related method to clone assembled fragments using restriction enzymes. In particular, an assembled TCR Vβ-Cβ-Vα fragment can be cloned into an expression plasmid vector containing TCR Cα fragment by using DNA ligase followed by restriction enzymes. To provide a sequence that can cleave a vector at Cα fragment, artificial restriction enzyme site is introduced in the Cα region. In this example, TCGCGA sequence which is recognized by NruI (or RruI) enzyme was introduced. A forward (NruI-Cα-F) and reverse primers (NruI-Cα-R) that contain TCGCGA sequence was designed. Two PCR reactions is performed using unmodified TCR-expression cassette as a template using HTTCR#A and NruI-Cα-R, and HTTCR#J and NruI-Cα-F. Resulting amplicons are connected by overlapping PCR using HTTCR#A and HTTCR#J and cloned into an expression vector. Additional primer sequences include:
NruI-Cα-F: TTCACCGATCGCGATTCTCAAACAAATGTGTCACAAAGTAAGG (SEQ ID NO:102)
NruI-Cα-R: GAGAATCGCGATCGGTGAATAGGCAGACAGACTT (SEQ ID NO:103). An example is provided in 16B, which shows introduction of NruI restriction enzyme site in the Cα region.

To create a restriction enzyme site at 3' end of TCR Vα fragment to ligate to NruI-treated blunt end of the plasmid, HTTCR#E was replaced by HTTCR#E-SwaI primer which contains ATTTAAAT sequence which is recognized by SwaI (or SmiI). NNN represents any 3 nucleotide sequence to increase efficiency of restriction enzyme reaction.

Figure 16:
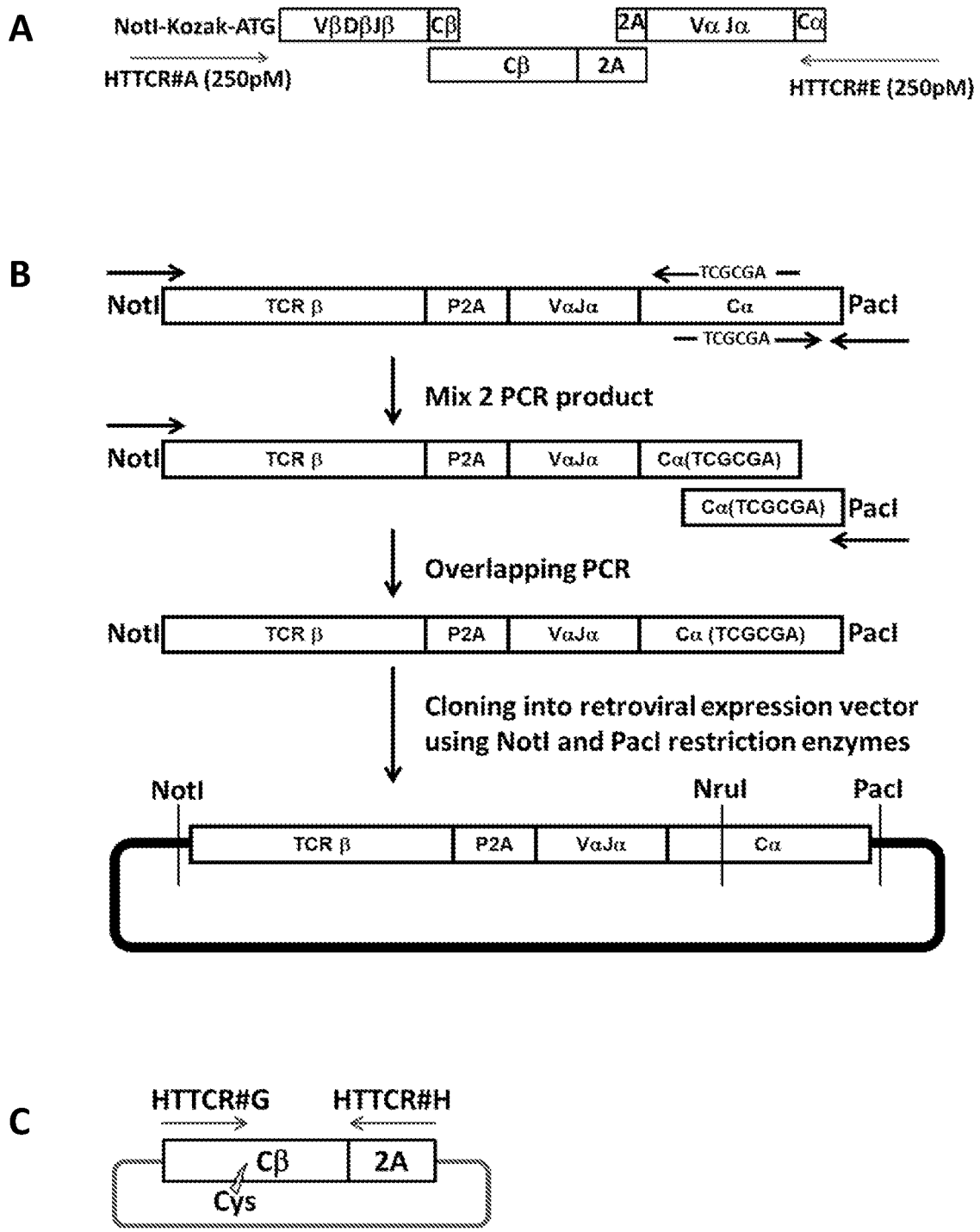
FIG. 16. Alternative method to assemble TCR Vβ, Cβ, Vα fragments by overlapping PCR (A). Introduction of NruI restriction enzyme site in the Cα region (B). This plasmid is used as an alternative destination vector for cloning of the NotI/SwaI-treated amplicon obtained by overlapping PCR using HTTCR#A and HTTCR#E-SwaI as shown in (A). Preparation of TCR Cβ-2A fusion fragments by PCR amplification from a template plasmid (C).

An additional primer sequence includes: HTTCR#E-SwaI NNNATTTAAATCGGTGAATAGGCAGACAGACTTGT (SEQ ID NO:104). In one embodiment, an assembled TCR Vβ-Cβ-2A-Vα fragment, for example created by 3 fragments overlapping PCR as shown in FIG. 16, is treated with NotI and SwaI restriction enzymes. NotI-recognizing sequence (GCGGCCGC) and SwaI-recognizing sequence (ATTTAAAT) are not present in any previously known TCR Vα, Jα, Cα, Vβ, Dβ, Jβ, or Cβ fragments and 2A sequences. Furthermore, the probability to create these 8 nucleotides sequence by random nucleotide insertion and deletion during TCR recombination process is extremely low. Therefore, treatment with NotI and SwaI is not expected to internally cut the assembled TCR product. The NruI-modified plasmid vector is treated by NotI and NruI restriction enzymes. Assembled TCR fragment and plasmid vector are ligated by using DNA ligase. Ligation of SwaI-treated TCR fragment and NruI-treated Cα fragment in the plasmid produces nucleotide sequence encoding natural Cα amino acid sequence.

As discussed above, in general, methods of this disclosure comprise amplifying TCR coding regions from polynucleotides extracted from T cells, modifying the amplified polynucleotides such that they are suitable for incorporation into a recombinant vector, and incorporating the polynucleotide sequences encoding at least TCR α and β chain coding sequences into a recombinant expression vector. This is performed using an ordered series of steps that are described above. Primers of this disclosure are used in general in a cloning scheme, non-limiting representations of which is provided in FIGS. 1 and 13. With respect to primers of Table 1, each of the primer sequences of this disclosure can exclude the sequence AAGGATCCGAATTCCTGCAGG (SEQ ID NO:105), and can exclude the sequence TGGAGGAGAACCCTGGACCT (SEQ ID NO:106), and can exclude these sequences from being present at the 5' end, 3' end, or at any other position in the primer sequences.

Primers of this disclosure, such as the TCR Variable Beta primers of Table 1 can each comprise the sequence CGGCCGCCACC (SEQ ID NO:107), which may be the 5' terminal end functions as a tag in the PCR. This sequence can include ATG, which is the initiation codon for TCR β chain, at the 3' terminal end. Primers of this disclosure, such as the TCR Variable Alpha primers in Table 1, can each comprise at the sequence AACCCCGGTCCC (SEQ ID NO:108), which may be at the 5' terminal end.

Complementary DNA (cDNA) can be synthesized from total RNA or mRNA of T cells using a reverse transcriptase and an oligo dT primer. Other primers such as random hexamer and TCR gene-specific primers can be used to prime reverse transcription. In this example, second strand cDNA is synthesized using combinations of primers described in Table 1. In particular, a combination of 45 and 49 forward primers containing the ATG initiation codon were designed to amplify any TCR with known Vβ and Vα segments, respectively. TCR Vβ-specific primers (those beginning with primer name "HTTCR#C" in Table 1) are flanked with an incomplete NotI-restriction site and the Kozak consensus sequence before initiation codon (CGGCCGCCACC(ATG)) (SEQ ID NO:109). TCR Vα-specific HTTCR#F primers (those beginning with primer name "HTTCR#F" in Table 1) are flanked with a part of 2A sequence (AACCCCGGTCCC (ATG)) (SEQ ID NO:110) before the initiation codon. These flanked sequences function as tags in the PCR amplification process, a non-limiting illustration of which is provided in FIG. 1, Step 4. As shown in FIG. 13 Step 4, variable regions for TCR α and β chains are amplified by PCR using common primer sets, for example, HTTCR#A and HTTCR#B for Vβ and HTTCR#D and HTTCR#E for Vα. The use of the common primer sets in PCR allows unbiased amplification of TCR genes when it is applied to oligoclonal T cell population.

Figure 14:
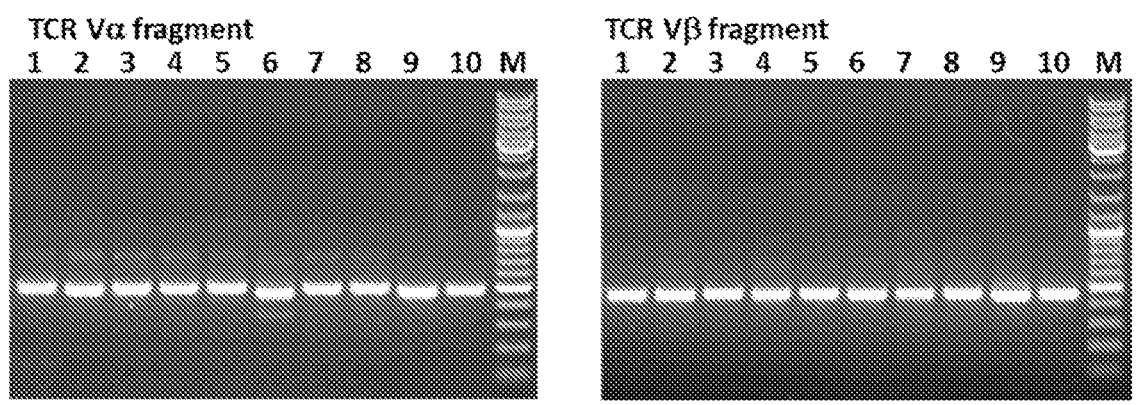
FIG. 14. Example of PCR amplification of Vα and vβ cDNA from T-cell clones. Clones #1/#2/#3/#4 are CD8+ T cell clones, #5/#6/#7/#8 are CD4+ T-cell clones, and #10 is Jurkat T lymphoma cells. M is a marker, GeneRuler DNA Ladder Mix from Thermo Scientific.

FIG. 2A and FIG. 14 show one non-limiting example of TCR Vα and Vβ PCR amplification from T-cell clones through procedures described in FIG. 1 and FIG. 13. However, to amplify TCR from T-cell clones, the second-strand cDNA synthesis and PCR reactions in FIG. 1 (and FIG. 13), Step 2 and Step 4, can be combined while Step 3 can be omitted. This alternative method for use with T-cell clones or single T-cells is outlined in FIG. 15. This method is preferred if the sample comprises T-cell clones or single T-cells, where different amplification efficiency by multiplexed primers is not a problem, but does not work with oligoclonal T-cell samples. Amplified TCR α and β chain variable fragments are purified by agarose gel electrophoresis and or using commercially available reagents, such as Zymoclean™ Gel DNA Recovery kit from Zymo Research. The next step which is shown in FIG. 13 Step 5 comprises assembly with constant fragments and cloning into a plasmid. In particular, the TCR β chain constant region+2A sequence fusion fragment is amplified from a stocked template containing the fusion gene depicted in FIG. 12. This fragment overlaps with β and α chain variable region fragments at Cβ and 2A sites, respectively. This constant region fragment can contain an artificial Cysteine modification, which enhances paring with Cysteine-modified TCR α chain by forming a disulfide-bond, but those skilled in the art will recognize given the benefit of this disclosure that various embodiments permit the constant region to be an unmodified fragment, or it may comprise any other modification, some of which are described above. Modifications can be one or more of the following: (1) replacement by TCR constant regions from other species such as those from murine TCR, (2) addition of leucine zipper motif, (3) addition of T-cell activating domains such as intracellular domains from CD3, CD28, 4-1BB, OX-40, GITR, ICOS.

Figure 17:
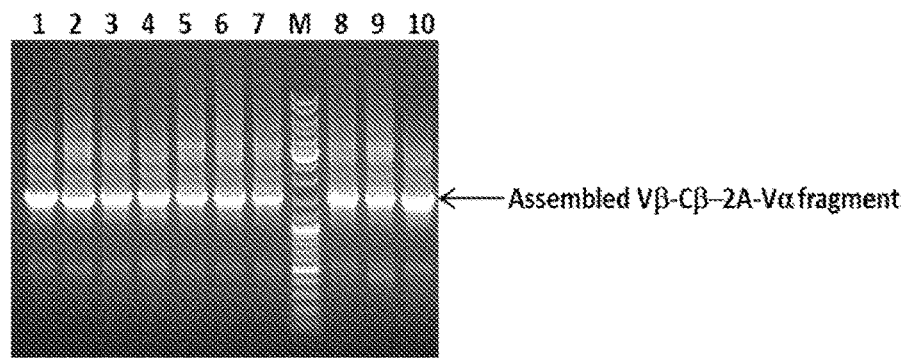
FIG. 17. Example of assembling of TCR Vβ, Cβ, and Vα fragments by overlapping PCR. #1 Clones #2/#3/#4/#5 are CD4+ T cell clones, #6/#7/#8/#9/#10 are CD8+ T-cell clones, and #1 is Jurkat T lymphoma cells. M is a marker, GeneRuler DNA Ladder Mix from Thermo Scientific.

Alternatively, three fragments can be fused by overlapping PCR. An example is shown in FIG. 16A. In this example, three fragments are mixed and amplified using HTTCR#A and HTTCR#E primers by PCR. Fused fragment can be cloned into expression vector by ligation-independent cloning or related methods, or by using a DNA ligase. An example of assembling of three fragments by overlapping PCR is shown in FIG. 17.

The plasmid vector, in which assembled TCR α and β variable regions and Cβ region is cloned, contains the constant region of TCR α chain which was modified by a Cysteine, which enhances paring with the Cystein-modified TCR β chain in this example. Modifications of TCR α chain constant region can be one or more of the following: (1) replacement by TCR constant regions from other species such as those from murine TCR, (2) addition of leucine zipper motif, (3) addition of T-cell activating domains such as intracellular domains from CD3, CD28, 4-1BB, OX-40, GITR, ICOS. This TCR Cα overlaps with α chain variable fragments. The cloning vector contains tag-sequence which overlaps with β chain variable fragment. The ligation product is used to transform competent cells (such as Stb13 or NEBStable) and plated on agar plate with antibiotics.

Figure 19:
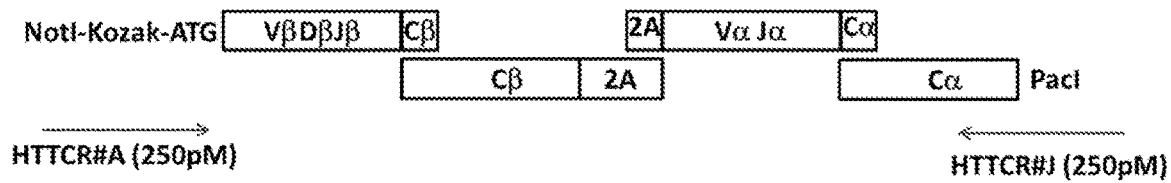
FIG. 19. Alternative method to assemble 4 fragments by overlapping PCR. The amplicon, which is the complete TCR expressing cassette, is cloned in the expression plasmid vector using ligation independent cloning or using restriction enzymes (NotI and PacI in this example) and DNA ligase.

As an alternative to the three fragment cloning scheme (see FIG. 16, for example) it is also possible to use a four fragment approach, which is summarized in FIGS. 18 and 19, but it is generally known that the efficiency of assembling 4 fragments by ligation-independent cloning is lower than assembling 3 fragments. The assembled PCR product is cloned into a plasmid for example by using NotI and PacI restriction enzyme sites by a DNA ligase, or by using ligation-independent cloning method such as Gibson Assembly cloning.

Figure 20:
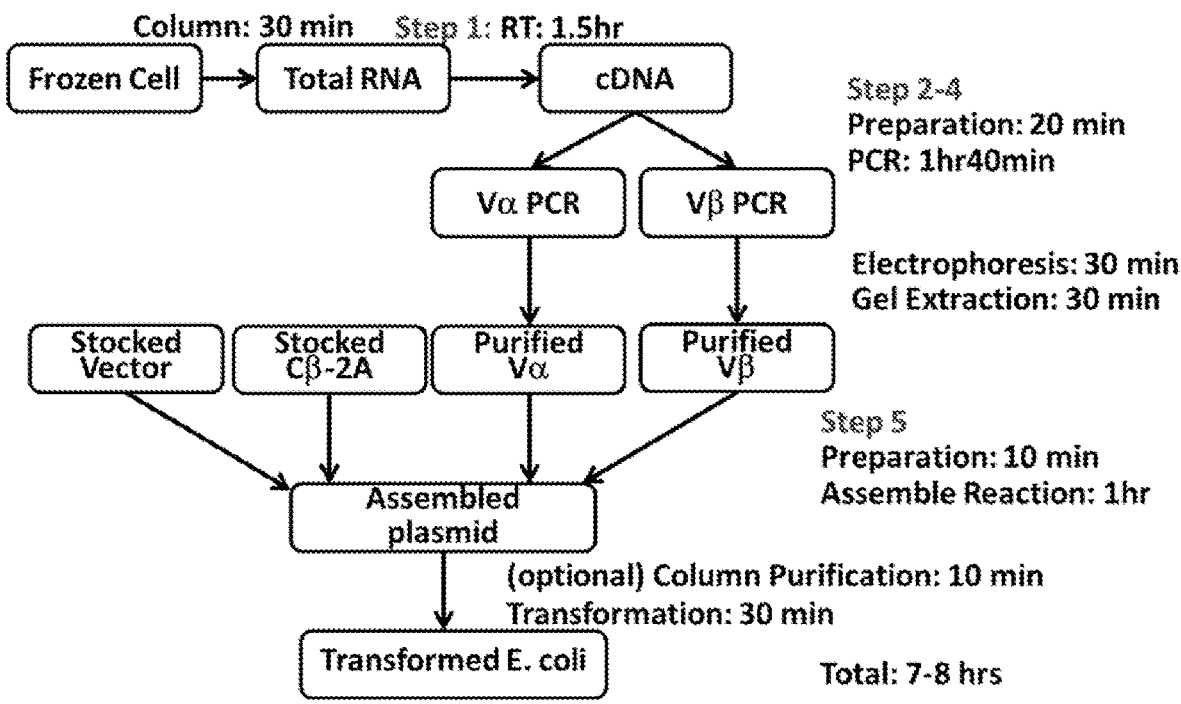
FIG. 20 provides a representative flow chart of "High-Throughput" 1-day TCR cloning protocol.

In view of the foregoing, it will be apparent to those skilled in the art that the present disclosure provides a high-throughput TCR cloning protocol that is capable of being performed in a single day, as illustrated by the non-limiting flow chart depicted in FIG. 20.

Table 1 provides primer sequences and names for primers that can be used in embodiments of this disclosure. Accordingly, the disclosure includes kits comprising combinations of these primers that are suitable for use in the rapid TCR cloning processes described herein. The kits can comprise one or more primers, such as mixtures of primers in any combination(s), and such mixtures can be provided in one or more separate containers. In certain embodiments the primer combinations in the kit can comprise or consist of the 45 and 49 primer combinations that contain the ATG initiation codon for amplifying any TCR with known Vβ and Vα alleles, respectively. These include the TCR Vβ-specific primers that begin with primer name "HTTCR#C" in Table 1 and the TCR Vα-specific primers that being with "HTTCR#F" in Table 1. The kits can comprise reagents for amplification of TCRs, and for cloning the TCRs into expression vectors. The kits may include printed materials that instruct a user as to how to clone TCRs from samples of TCR-expressing cells. In addition to the sequences provided in Table 1, the disclosure includes the following sequence: NxGCGGCCGCCACCATG (Nx represents 0-50) (SEQ ID NO:111), which can be used for instance as an alternative to HT-TCR#A. "Nx" in this sequence represents any nucleotide sequences of up to 50 nts long that could be included in the primers, depending on the cloning method, such as to facilitate use of restriction enzymes, and/or ligation-independent cloning including but not necessarily limited to Gibson assembly, InFusion cloning, NEBuilder cloning, and the like.

| Primer Name | Description | Bases | Sequence |
|---|---|---|---|
| HT-TCR#I | HT-TCR#6Ca-F | 30 | CTCTAAATCCAGTGACAAGTCTGTCTGCCT (SEQ ID NO: 112) |
| HT-TCR#J | HT-TCR#8Pac1-STOP-Ca-R | 29 | NxTTAATTAATCAGCTGGACCACAGCCG (Nx represents any three nucleotides, one example of which is CAG)(SEQ ID NO: 113) |

TABLE 1

Sequences of primers used in the TCR gene amplification

| Name | Description | Length | Sequence | SEQ ID NO: |
|---|---|---|---|---|
| HT-TCR#A | β chain-tag-specific forward | 43 | ACTTAAGCTTGGTACCGAGCTCGGATCTGCGGCCGCCACCATG | 1 |
| HT-TCR#B | Cβ-specific Reverse | 30 | CTCAAACACAGCGACCTCGGGTGGGAACAC | 2 |
| TCR Variable Beta primers | | | | |
| HTTCR#C-1 forward | TRBV2*1,2-specific- | 34 | CGGCCGCCACCATGGATACCTGGCTCGTATGCTG | 3 |
| HTTCR#C-2 forward | TRBV2*3-specific- | 34 | CGGCCGCCACCATGGATACCTGGCTGTATGCTGG | 4 |
| HTTCR#C-3 forward | TRBV3-1*1-specific- | 28 | CGGCCGCCACCATGGGCTGCAGGCTCCT | 5 |
| HTTCR#C-4 | TRBV3-1*2/9*1,2,3-specific-forward | 30 | CGGCCGCCACCATGGGCTTCAGGCTCCTCT | 6 |
| HTTCR#C-5 | TRBV4-1,2,3-specific-forward | 27 | CGGCCGCCACCATGGGCTGCAGGCTGC | 7 |

TABLE 1-continued

Sequences of primers used in the TCR gene amplification

| Name | Description | Length | Sequence | SEQ ID NO: |
|---|---|---|---|---|
| HTTCR#C-6 | TRBV5-1*1-specific-forward | 28 | CGGCCGCCACCATGGGCTCCAGGCTGCT | 8 |
| HTTCR#C-7 | TRBV5-4,5-specific-forward-specific-forward | 26 | CGGCCGCCACCATGGGCCCTGGGCTC | 9 |
| HTTCR#C-8 | TRBV5-6*1-specific-forward-specific-forward | 24 | CGGCCGCCACCATGGGCCCCGGGC | 10 |
| HTTCR#C-9 | TRBV5-8*1,2-specific-forward-specific-forward | 28 | CGGCCGCCACCATGGGACCCAGGCTCCT | 11 |
| HTTCR#C-10 | TRBV6-1*1/6-9*1-specific-forward | 30 | CGGCCGCCACCATGAGCATCGGGCTCCTGT | 12 |
| HTTCR#C-11 | TRBV6-2*1/6-3*1/6-8*1-specific-forward | 28 | CGGCCGCCACCATGAGCCTCGGGCTCCT | 13 |
| HTTCR#C-12 | TRBV6-4*1-specific-forward | 34 | CGGCCGCCACCATGAGAATCAGGCTCCTGTGCTG | 14 |
| HTTCR#C-13 | TRBV6-4*2-specific-forward | 32 | CGGCCGCCACCATGAGCATCAGGCTCCTGTGC | 15 |
| HTTCR#C-14 | TRBV6-5*1-specific-forward | 30 | CGGCCGCCACCATGAGCATCGGCCTCCTGT | 16 |
| HTTCR#C-15 | TRBV6-6*1,2,3,4,5-specific-forward | 32 | CGGCCGCCACCATGAGCATCAGCCTCCTGTGC | 17 |
| HTTCR#C-16 | TRBV7-2,3,4/7-8*1,2-specific-forward | 28 | CGGCCGCCACCATGGGCACCAGGCTCCT | 18 |
| HTTCR#C-17 | TRBV7-6*1/11-2*1,2,3-specific-forward | 32 | CGGCCGCCACCATGGGCACCAGTGTCCTATGT | 19 |
| HTTCR#C-18 | TRBV7-6*2-specific-forward | 32 | CGGCCGCCACCATGGGCACCAGTCTCCTATGC | 20 |
| HTTCR#C-19 | TRBV7-7*1-specific-forward | 35 | CGGCCGCCACCATGGGTACCAGTCTCCTATGCTGG | 21 |
| HTTCR#C-20 | TRBV7-9*1,2,3,7-specific-forward | 28 | CGGCCGCCACCATGGGCACCAGCCTCCT | 22 |
| HTTCR#C-21 | TRBV7-9*4-specific-forward | 28 | CGGCCGCCACCATGGGGACCAGCCTCCT | 23 |
| HTTCR#C-22 | TRBV7-9*6-specific-forward | 30 | CGGCCGCCACCATGGCCCTGTGTCTCCTGG | 24 |
| HTTCR#C-23 | TRBV10-1*1,2-specific-forward | 30 | CGGCCGCCACCATGGGCACGAGGCTCTTCT | 25 |
| HTTCR#C-24 | TRBV10-2*1/7-2*2-specific-forward | 30 | CGGCCGCCACCATGGGCACCAGGCTCTTCT | 26 |
| HTTCR#C-25 | TRBV10-2*2-specific-forward | 32 | CGGCCGCCACCATGTGGCCCTTTGTCTGCTGT | 27 |
| HTTCR#C-26 | TRBV10-3*1,2,3,4-specific-forward | 37 | CGGCCGCCACCATGGGCACAAGGTTGTTCTTCTATGT | 28 |
| HTTCR#C-27 | TRBV11-1*1-specific-forward | 32 | CGGCCGCCACCATGAGCACCAGGCTTCTCTGC | 29 |
| HTTCR#C-28 | TRBV11-3*1,2,3-specific-forward | 31 | CGGCCGCCACCATGGGTACCAGGCTCCTCTG | 30 |
| HTTCR#C-29 | TRBV12-3*1-specific-forward | 32 | CGGCCGCCACCATGGACTCCTGGACCTTCTGC | 31 |
| HTTCR#C-30 | TRBV12-4*1-specific-forward | 31 | CGGCCGCCACCATGGACTCCTGGACCCTCTG | 32 |
| HTTCR#C-31 | TRBV12-4*2-specific-forward | 29 | CGGCCGCCACCATGGGCTCCTGGACCCTC | 33 |
| HTTCR#C-32 | TRBV12-5*1-specific-forward | 28 | CGGCCGCCACCATGGCCACCAGGCTCCT | 34 |
| HTTCR#C-33 | TRBV13*1,2-specific-forward | 33 | CGGCCGCCACCATGCTTAGTCCTGACCTGCCTG | 35 |
| HTTCR#C-34 | TRBV14*1,2-specific-forward | 38 | CGGCCGCCACCATGGTTTCCAGGCTTCTCAGTTTAGTG | 36 |
| HTTCR#C-35 | TRBV15*1,2,3-specific-forward | 30 | CGGCCGCCACCATGGGTCCTGGGCTTCTCC | 37 |
| HTTCR#C-36 | TRBV16*1,3-specific-forward | 36 | CGGCCGCCACCATGAGCCCAATATTCACCTGCATCA | 38 |
| HTTCR#C-37 | TRBV18*1-specific-forward | 34 | CGGCCGCCACCATGGACACCAGAGTACTCTGCTG | 39 |
| HTTCR#C-38 | TRBV19*1,2,3-specific-forward | 31 | CGGCCGCCACCATGAGCAACCAGGTGCTCTG | 40 |
| HTTCR#C-39 | TRBV20-1*1,2,3,4,5,6,7-specific-forward | 30 | CGGCCGCCACCATGCTGCTGCTTCTGCTGC | 41 |
| HTTCR#C-40 | TRBV24-1*1-specific-forward | 30 | CGGCCGCCACCATGGCCTCCCTGCTCTTCT | 42 |

TABLE 1-continued

Sequences of primers used in the TCR gene amplification

| Name | Description | Length | Sequence | SEQ ID NO: |
|---|---|---|---|---|
| HTTCR#C-41 | TRBV25-1*1-specific-forward | 36 | CGGCCGCCACCATGACTATCAGGCTCCTCTGCTACA | 43 |
| HTTCR#C-42 | TRBV27*1-specific-forward | 26 | CGGCCGCCACCATGGGCCCCCAGCTC | 44 |
| HTTCR#C-43 | TRBV28*1-specific-forward | 33 | CGGCCGCCACCATGGGAATCAGGCTCCTCTGTC | 45 |
| HTTCR#C-44 | TRBV29-1*1,2,3-specific-forward | 35 | CGGCCGCCACCATGCTGAGTCTTCTGCTCCTTCTC | 46 |
| HTTCR#C-45 | TRBV30*1,2,5-specific-forward | 34 | CGGCCGCCACCATGATGCTCTGCTCTCTCCTTGC | 47 |

TCR Variable Alpha primers

| Name | Description | Length | Sequence | SEQ ID NO: |
|---|---|---|---|---|
| HT-TCR#D | α chain tag-specific forward | 29 | GGAGACGTGGAAGAAAACCCCGGTCCCATG | 48 |
| HT-TCR#E | Cα-specific reverse | 30 | AGGCAGACAGACTTGTCACTGGATTTAGAG | 49 |
| HTTCR#F-1 | TRAV1-1*1,2-specific forward | 37 | AACCCCGGTCCCATGTGGGGAGCTTTCCTTCTCTATG | 50 |
| HTTCR#F-2 | TRAV1-2*1-specific forward | 42 | AACCCCGGTCCCATGTGGGGAGTTTTCCTTCTTTATGTTTCC | 51 |
| HTTCR#F-3 | TRAV2*1-specific forward | 33 | AACCCCGGTCCCATGGCTTTGCAGAGCACTCTG | 52 |
| HTTCR#F-4 | TRAV3*1-specific forward | 31 | AACCCCGGTCCCATGGCCTCTGCACCCATCT | 53 |
| HTTCR#F-5 | TRAV4*1-specific forward | 32 | AACCCCGGTCCCATGAGGCAAGTGGCGAGAGT | 54 |
| HTTCR#F-6 | TRAV5*1-specific forward | 41 | AACCCCGGTCCCATGAAGACATTTGCTGGATTTTCGTTCCT | 55 |
| HTTCR#F-7 | TRAV6*1,3,4-specific forward | 34 | AACCCCGGTCCCATGGAGTCATTCCTGGGAGGTG | 56 |
| HTTCR#F-8 | TRAV6*2,5,6-specific forward | 32 | AACCCCGGTCCCATGGAGTCATCCCTGGGAGG | 57 |
| HTTCR#F-9 | TRAV7*1-specific forward | 34 | AACCCCGGTCCCATGGAGAAGATGCGGAGACCTG | 58 |
| HTTCR#F-10 | TRAV8-1*1,2-specific forward | 35 | AACCCCGGTCCCATGCTCCTGTTGCTCATACCAGT | 59 |
| HTTCR#F-11 | TRAV8-2,4,6-specific forward | 31 | AACCCCGGTCCCATGCTCCTGCTGCTCGTCC | 60 |
| HTTCR#F-12 | TRAV8-3*1,2,3-specific forward | 34 | AACCCCGGTCCCATGCTCCTGGAGCTTATCCCAC | 61 |
| HTTCR#F-13 | TRAV9-1*1-specific forward | 39 | AACCCCGGTCCCATGAATTCTTCTCTAGGACCAGCGATT | 62 |
| HTTCR#F-14 | TRAV9-2*1,2,3,4-specific forward | 47 | AACCCCGGTCCCATGAACTATTCTCCAGGCTTAGTATCTCTGATACT | 63 |
| HTTCR#F-15 | TRAV10*1-specific forward | 40 | AACCCCGGTCCCATGAAAAAGCATCTGACGACCTTCTTGG | 64 |
| HTTCR#F-16 | TRAV12-1*1,2-specific forward | 46 | AACCCCGGTCCCATGATGATATCCTTGAGAGTTTTACTGGTGATCC | 65 |
| HTTCR#F-17 | TRAV12-2-specific forward | 47 | AACCCCGGTCCCATGATGAAATCCTTGAGAGTTTTACTAGTGATCCT | 66 |
| HTTCR#F-18 | TRAV12-3*1-specific forward | 46 | AACCCCGGTCCCATGATGAAATCCTTGAGAGTTTTACTGGTGATCC | 67 |
| HTTCR#F-19 | TRAV12-3*2-specific forward | 46 | AACCCCGGTCCCATGATGAAATCCTTGAGAGTTTTACTGGTCATCC | 68 |
| HTTCR#F-20 | TRAV13-1*1,2,3-specific forward | 46 | AACCCCGGTCCCATGACATCCATTCGAGCTGTATTTATATTCCTGT | 69 |
| HTTCR#F-21 | TRAV13-2*1,2-specific forward | 45 | AACCCCGGTCCCATGATGGCAGGCATTCGAGTTTTATTTATGTAC | 70 |
| HTTCR#F-22 | TRAV14/DV4*1,2,3,4-specific forward | 37 | AACCCCGGTCCCATGTCACTTTCTAGCCTGCTGAAGG | 71 |
| HTTCR#F-23 | TRAV16*1-specific forward | 34 | AACCCCGGTCCCATGAAGCCCACCCTCATCTCAG | 72 |
| HTTCR#F-24 | TRAV17*1-specific forward | 35 | AACCCCGGTCCCATGGAAACTCTCCTGGGAGTGTC | 73 |
| HTTCR#F-25 | TRAV18*1-specific forward | 33 | AACCCCGGTCCCATGCTGTCTGCTTCCTGCTCA | 74 |
| HTTCR#F-26 | TRAV19*1-specific forward | 33 | AACCCCGGTCCCATGAACATGCTGACTGCCAGC | 75 |
| HTTCR#F-27 | TRAV20*1,2,3,4-specific forward | 40 | AACCCCGGTCCCATGGAGAAAATGTTGGAGTGTGCATTCA | 76 |
| HTTCR#F-28 | TRAV21*1,2-specific forward | 31 | AACCCCGGTCCCATGGAGACCCTCTTGGGCC | 77 |
| HTTCR#F-29 | TRAV22*1-specific forward | 37 | AACCCCGGTCCCATGAAGAGGATATTGGGAGCTCTGC | 78 |

TABLE 1-continued

Sequences of primers used in the TCR gene amplification

| Name | Description | Length | Sequence | SEQ ID NO: |
|---|---|---|---|---|
| HTTCR#F-30 | TRAV23/DV6*1,2,3,4-specific forward | 47 | AACCCCGGTCCCATGGACAAGATCTTAGGAGCATCATTTTTAGTTCT | 79 |
| HTTCR#F-31 | TRAV24*1,2-specific forward | 36 | AACCCCGGTCCCATGGAGAAGAATCCTTTGGCAGCC | 80 |
| HTTCR#F-32 | TRAV25*1-specific forward | 44 | AACCCCGGTCCCATGCTACTCATCACATCAATGTTGGTCTTATG | 81 |
| HTTCR#F-33 | TRAV26-1*1,2,3-specific forward | 34 | AACCCCGGTCCCATGAGGCTGGTGGCAAGAGTAA | 82 |
| HTTCR#F-34 | TRAV26-2*1-specific forward | 40 | AACCCCGGTCCCATGAGGTTGGTGACAAGCATTACTGTAC | 83 |
| HTTCR#F-35 | TRAV26-2*02-specific forward | 42 | AACCCCGGTCCCATGAAGTTGGTGACAAGCATTACTGTACTC | 84 |
| HTTCR#F-36 | TRAV27*1,2,3-specific forward | 36 | AACCCCGGTCCCATGGTCCTGAAATTCTCCGTGTCC | 85 |
| HTTCR#F-37 | TRAV29/DV5*1-specific forward | 29 | AACCCCGGTCCCATGGCCATGCTCCTGGG | 86 |
| HTTCR#F-38 | TRAV30*1,3,4-specific forward | 38 | AACCCCGGTCCCATGGAGACTCTCCTGAAAGTGCTTTC | 87 |
| HTTCR#F-39 | TRAV30*2-specific forward | 35 | AACCCCGGTCCCATGGAGACTCTCCTGAAAGTGCC | 88 |
| HTTCR#F-40 | TRAV34*1-specific forward | 37 | AACCCCGGTCCCATGGAGACTGTTCTGCAAGTACTCC | 89 |
| HTTCR#F-41 | TRAV35*1,2-specific forward | 49 | AACCCCGGTCCCATGCTCCTTGAACATTTATTAATAATCTTGTGGATGC | 90 |
| HTTCR#F-42 | TRAV36/DV7*1-specific forward | 33 | AACCCCGGTCCCATGATGAAGTGTCCGCAGGCT | 91 |
| HTTCR#F-43 | TRAV36/DV7*2,3,4-specific forward | 38 | AACCCCGGTCCCATGATGAAGTGTCCACAGGCTTTACT | 92 |
| HTTCR#F-44 | TRAV38-1*1,2,3-specific forward | 35 | AACCCCGGTCCCATGACACGAGTTAGCTTGCTGTG | 93 |
| HTTCR#F-45 | TRAV38-1*4-specific forward | 35 | AACCCCGGTCCCATGACACCAGTTAGCTTGCTGTG | 94 |
| HTTCR#F-46 | TRAV38-2/DV8*1-specific forward | 29 | AACCCCGGTCCCATGGCATGCCCTGGCTT | 95 |
| HTTCR#F-47 | TRAV39*1-specific forward | 42 | AACCCCGGTCCCATGAAGAAGCTACTAGCAATGATTCTGTGG | 96 |
| HTTCR#F-48 | TRAV40*1-specific forward | 43 | AACCCCGGTCCCATGAACTCCTCTCTGGACTTTCTAATTCTGA | 97 |
| HTTCR#F-49 | TRAV41*1-specific forward | 39 | AACCCCGGTCCCATGGTGAAGATCCGGCAATTTTGTTG | 98 |
| TCR Constant Beta Primers | | | | |
| HTTCR#G | Cβ-specific forward | 30 | GTGTTCCCACCCGAGGTCGCTGTGTTTGAG | 99 |
| HTTCR#H | P2A-specific Reverse | 30 | CATGGGACCGGGGTTTTCTTCCACGTCTCC | 100 |

The following Examples are intended to illustrate but not limit the invention.

Example 1

Amplification and Cloning of TCR Genes

Figure 6:
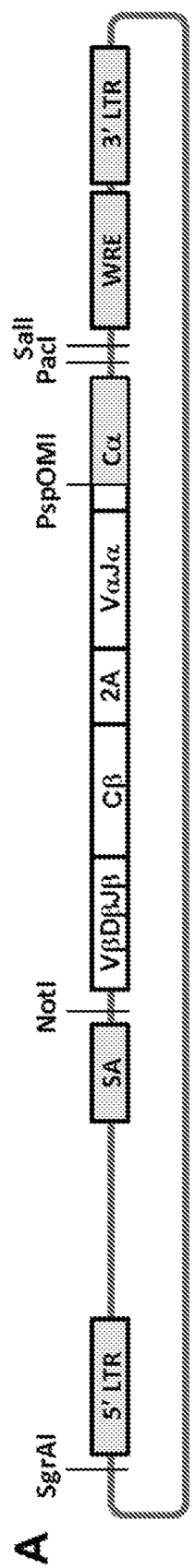
FIG. 6. Construction of a destination plasmid for TCR gene cloning. (A) Schematic representation of the destination plasmid vector. To create the destination plasmid, fragment from 5' Long Terminal Repeat (LTR) to the multiple cloning site (MCS) in a pDON-5 retroviral vectors was amplified by PCR using the sense primer:
TGGCGCCGGTGATGTGAAAGACCCCACCTGTAG
(SEQ ID NO:116) (SgrAI site italicized) and anti-sense primer:
AATGTCGACTATGCGGCCGCA-
GATCCGAGCTCGGTACC (SEQ ID NO:117) (SalI and NotI sites italicized). The DNA fragment was column-purified and treated with SgrAI and SalI restriction enzymes and inserted into a Murine Stem Cell Virus (MSCV)-based retroviral plasmid pMIG-w (Addgene plasmid #12282)). The plasmid contains TCR-expressing cassette as a stuffer gene fragment. In the stuffer TCR-expressing cassette, Cα region was modified to provide a PspOMI-recognition site for excision of the stuffer fragment together with NotI, leaving 3' part of Cα-coding region in the vector fragment. To create PspOMI-containing TCR-expressing cassette, Two DNA fragments containing PspOMI-recognizing site in the α chain constant region was prepared by using (1) sense primer:
ACCAGCTGGGGCCCTCTAAATCCAGTGACAAGT
CTGTCTGCC (SEQ ID NO:99) (PspOMI site italicized) and anti-sense primer:
ATTGTCGACTTAATTAATCAGCTGGACCACAGCCG
(SEQ ID NO:100) (SalI and PacI sites italicized) and (2) vector-specific sense primer AATTGATCCGCGGCCGC-CACCATG (SEQ ID NO:131) (NotI site italicized) and anti-sense primer:
GAGGGCCCCAGCTGGTACACGGCAGGG (SEQ ID NO:101) (PspOMI site italicized). Two PCR fragments were fused by the overlap extension PCR. The fused fragment was introduced into the NotI and SalI site in the plasmid vector. Abbreviations used are: 5' LTR: 5' HCMV/MLV hybrid long terminal repeats; SA: the splice acceptor site from the human elongation factor 1a intron-exon junction; WRE; Woodchuck Hepatitis Virus Posttranscriptional Regulatory Element; 3' LTR; MSCV LTR. (B) Correction of PspOMI modification during assembling reaction. (1) TCR α chain constant region was modified to provide PspOMI-recognizing sequence; (2) Sequences of TCR VJα and restriction enzyme-treated and purified vector fragments before assembling; (3) During assembling reaction, both fragments were degraded by a 5'-to-3' exonuclease in the reaction mix, by which artificial PspOMI-recognizing sequence in the vector fragment is removed; and (4) After assembling, positive-strand DNA of TCR VJα fragment and negative-strand DNA of the vector fragment form the natural TCR Cα sequence.

A schematic TCR-expressing cassette designed for construction of retroviral vectors as discussed above is shown in FIG. 1A. To enable stoichiometric expression of TCR α and β chains from a single transcript, TCR α and β chains were genetically connected via the P2A translational-skipping site J. Matsuzaki, et al. Sci. Rep. 5, 14896 (2015); N. Banu, et al. Sci. Rep. 4, 4166 (2014)). The start codon for TCR β chain was preceded by the Kozak consensus sequence (GCCACC) for efficient translation. The constant regions of both chains were modified by a cysteine residue to create an artificial disulfide bond which enhances paring of transgenic TCR α and β chains and inhibits pairing with endogenous TCRs (C. J. Cohen, Y. et al., Cancer Res. 67, 3898-3903 (2007).). In the TCR-expressing cassette, the TCR α and chain variable (Vα/Vβ), joining (Jα/Jβ) and the TCR R chain diverse (Dβ) regions that are critical for antigen recognition are required to be obtained from antigen-specific T cells. In contrast, the constant regions can be prepared as stocked fragments that contain artificial modifications such as cysteine modification and fusion to the P2A site (a suitable procedure for making such a constant region is illustrated in FIG. 16C). In addition, the TCR α chain constant region can be included in the destination plasmid vector to reduce the number of fragments to be assembled. A destination retroviral expression plasmid was constructed as shown in FIG. 6A. The destination plasmid contains a TCR-expressing cassette as the stuffer fragment in which TCR Cα region was modified to contain PspOMI-recognizing site (GGGCCC) for excision of the stuffer fragment together with the NotI restriction enzyme. This artificial sequence was corrected to the natural Cα sequence during assembling reaction (FIG. 6B).

The 5' part of TCR α and β chains, Vα and Vβ, are highly variable. Therefore, without the knowledge of TCR sequences, a large number of multiplexed forward primers are required for PCR amplification. Two sets of multiplexed forward primers were designed for all known Vα and Vβ reported in the IMGT database (M. P. Lefranc, et al., Nucleic Acids Res. 43, D413-422 (2015)). Sequences of primers used in this study are listed in Table 1. The TCR Vβ-specific primer set consisted of 45 primers that have the common 5' tag sequence before the start codon. Similarly, 49 Vα-specific primers had another common tag sequence (the 3' region of the P2A site). The procedures for amplification and cloning of TCR genes are depicted in FIG. 1B. In all experiments for this study, we used standard cDNA prepared from the total RNA using oligo dT primers and a reverse transcriptase as PCR template (Step 1). Because PCR amplification by multiplexed primers can cause an amplification bias due to different efficiencies for each primer, amplification of Vα and Vβ regions was performed using the tag-specific forward primers and TCR constant region (Cα and Cβ)-specific reverse primers. To end this, the second-strand TCR cDNA was synthesized by a single-cycle polymerase reaction primed by multiplexed primers, thereby adding a tag sequence to 5' end of the second strand-cDNA (Step 2), followed by elimination of excess primers by Exonuclease I treatment (Step 3). Then, Vα and Vβ fragments were amplified by PCR using tag-specific forward and TCR common region (Cβ or Cα)-specific reverse primer pair (Step 4). The tag sequence for Vα has a 30 nucleotides overlap with a cloning site in the destination plasmid vector, while that for Vα has an overlap with a P2A-sequence. Cysteine-modified constant region for TCR β chain linked to P2A-sequence was PCR-amplified from the destination plasmid containing this fragment. Three fragments, VDJβ. Cβ-P2A, and VJα, were assembled with a linearized destination retroviral plasmid vector containing the cysteine-modified Cα fragment by a modified Gibson assembly using NEBuilder HiFi DNA Assembly Master Mix (Step 5). Using frozen stocked Cβ-P2A and linearized destination vector fragments, assembled vectors for transform *E. coli* competent cells were prepared within 4 hours.

Example 2

Construction of TCR-Expressing Retroviral Vectors from Tumor Antigen-Specific T-Cell Clones To validate the rapid TCR-cloning method, we constructed TCR-expressing retroviral vectors for four CD8$^+$ and five CD4$^+$ NY-ESO-1-specific T-cell clones that have unique combinations of TCR α and β chain genes from our cell bank. As a control T-cell clone, Jurkat T-lymphoma cell line (ATCC; TIB-152) was included. Vβ and Vα fragments were amplified as a single band for all T-cell clones tested (FIG. 2A). The assembled TCR-expressing vectors were used to transform chemically competent *E. coli*. Transformed cells were spread and incubated overnight on agar plates to produce confluent colonies. To confirm that the TCR-expressing cassette was correctly assembled, bulk plasmids that were obtained from pooled colonies were digested by NotI and PacI restriction enzymes, which excise full length TCR-expressing cassettes (FIG. 1A). As shown in FIG. 2B, a single band with expected size for the TCR-expressing cassette was excised from the plasmid at around 1.8 kb, indicating that our cloning procedures correctly assembled fragments as the expressing cassette.

Figure 7:
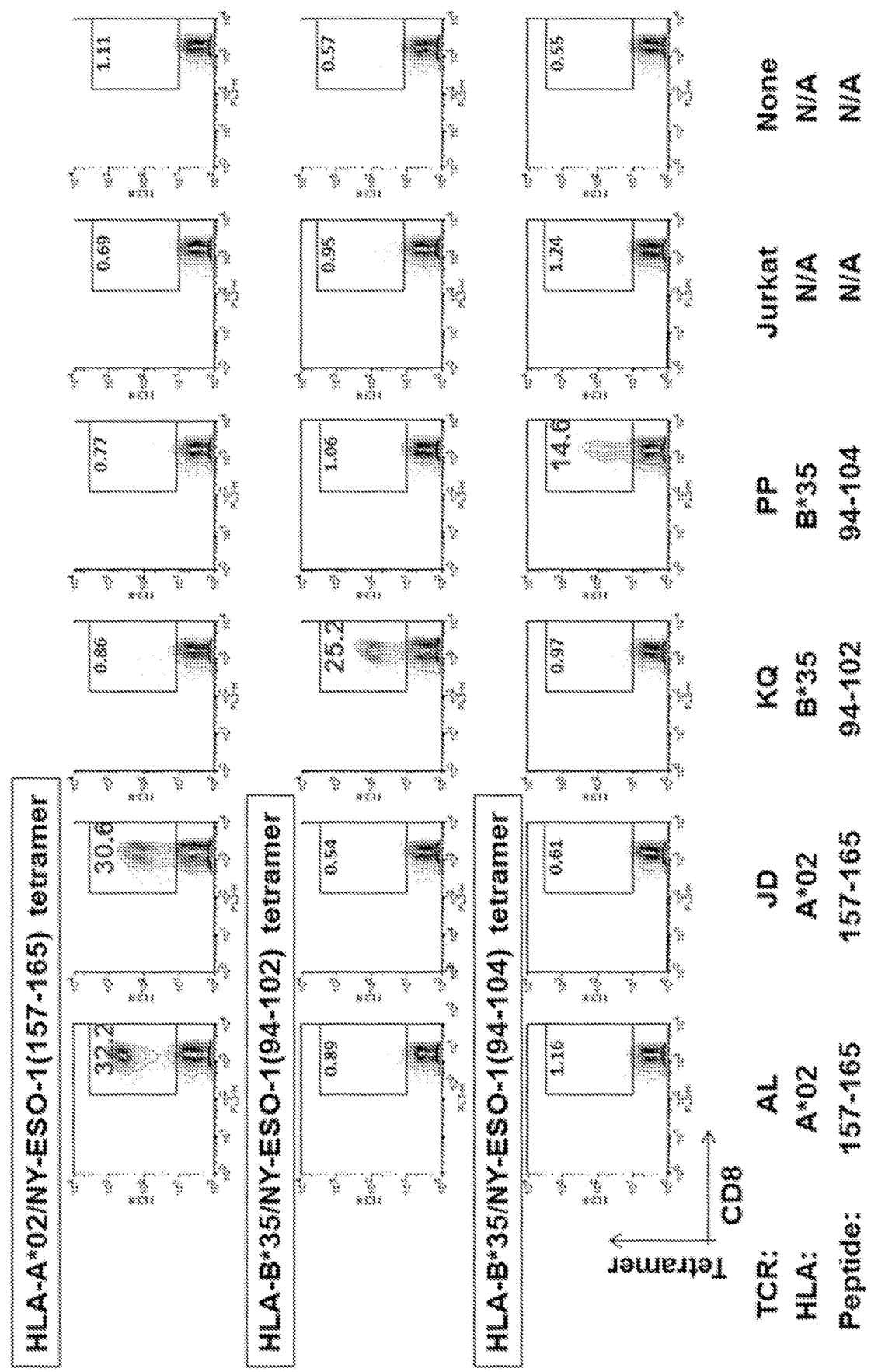
FIG. 7. Tetramer staining of NY-ESO-1-specific TCR-expressing T cells. NY-ESO-1-specific TCR-expressing retroviral vectors were constructed from 4 NY-ESO-1-specific CD8+ T-cell clones: AL, JD, KQ, and PP. As a control TCR gene, a TCR-expressing vector was constructed from Jurkat. Polyclonally activated T cells from healthy donor PBMC were transduced by retroviral vectors and stained with the indicated tetramer. Staining of cells gated on CD8 is shown.

To test the functionality of the cloned TCR, healthy donor T cells were polyclonally activated and infected with retroviruses generated from bulk plasmids containing T-cell clone-derived TCR-expressing cassettes. After a single infection, 25-35% of T cells expressed transduced TCR as determined by the increase in TCR Vβ subtype expression where appropriate antibodies are available (FIG. 2C). Functional expression of antigen-specific TCR α and β chain pairs was determined by MHC/peptide tetramer staining. Staining of untransduced and irrelevant TCR gene-transduced T cells was negligible. All 4 HLA class I-restricted TCR expressed on CD8$^+$ T cells were stained by corresponding tetramers (FIG. 2D and FIG. 7). TCR-transduced T cells produced IFN-γ and TNF-α upon co-culturing with the antigen and HLA-expressing cancer cell lines (FIG. 2E). To assess functional expression of HLA class II-restricted NY-ESO-1-specific TCRs for which MHC/peptide-tetramer reagents were not available, TCR gene-transduced T cells were co-cultured with antigen-pulsed target cells or MHC class II and NY-ESO-1-coexpressing cancer cells followed by intracellular cytokine staining. As shown in FIG. 8, HLA class II-restricted TCR gene-transduced T cells produced IFN-γ and TNF-α upon antigen stimulation. These results demonstrate that our cloning protocol rapidly constructs functional TCR-expressing vectors for all T-cell clones tested without the need of TCR sequence information.

Example 3

Figure 3:
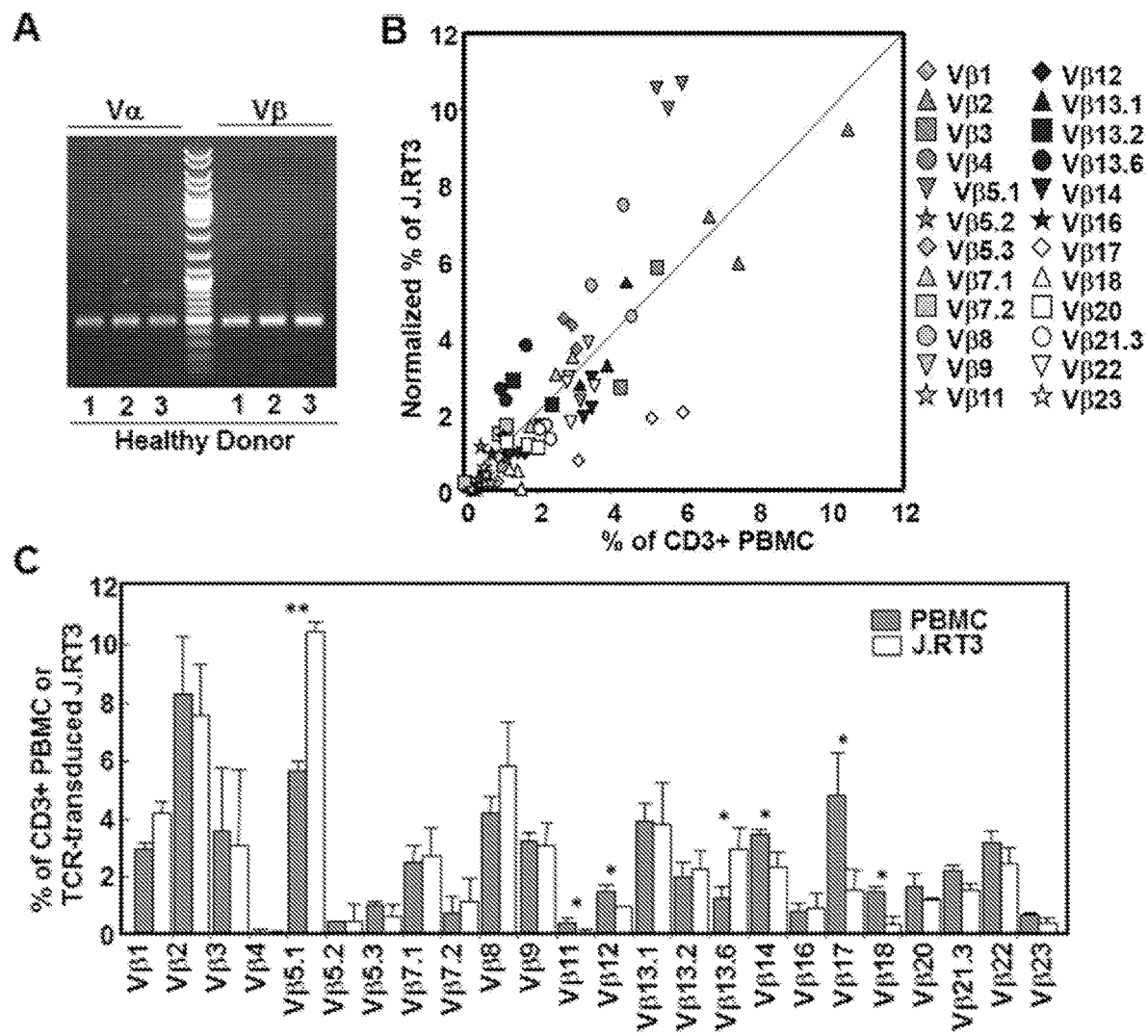
FIG. 3. Construction and characterization of TCR-gene library of peripheral polyclonal T cells. (A) Amplification of VJα and VDJβ fragments from polyclonal T cells. TCR genes were amplified from cDNA of PBMC from 3 healthy individuals and the product was electrophoresed on an agarose gel and visualized by ethidium bromide. (B, C) Comparison of Vβ subtype frequencies in peripheral T cells and TCR gene library-transduced J.RT3. Frequencies Vβ-subtype expressing CD3+ T cells in PBMC and TCR gene library-transduced J.RT3 was determined by flow-cytometry. Because of the limited availability of Vβ subtype-specific antibodies, total percentages of peripheral T cells that were stained by any of these antibodies were 59, 62, and 57% for 3 donors. Frequency for J.RT3 was normalized to the corresponding percentages in peripheral T cells. (B) Frequencies of Vβ-subtype expressing CD3+ PBMC were plotted against the corresponding values in J.RT3. (C) Mean frequencies for CD3+ PBMC and J.RT3 were compared. Each bar shows mean frequency and the standard deviation. *: $p<0.05$; **: $p<0.01$ by the two-tailed paired t-test.

Construction and Characterization of Randomly Paired TCR Libraries from Polyclonal T Cells Next, we applied our TCR-cloning protocol to construct randomly paired TCR-expression library from polyclonal T-cell populations. We first tested feasibility of constructing TCR-expression library from polyclonal T cells from peripheral blood mononuclear cells (PBMC) of 3 healthy donors. Both TCR Vα and Vβ were efficiently amplified from PBMC cDNA (FIG. 3A). Assembled plasmids were amplified in competent cells and purified from pooled colonies. The size of the library from one 50 μl vial of the competent cells was determined to be $2.8 \pm 0.5 \times 10^5$ (Mean±SD for 3 donors) by serial dilution of the transformed cells.

To investigate whether TCR gene amplification using the common primer sets against tag-specific forward and common TCR constant region-specific reverse primers enables unbiased amplification of different TCR species, we compared usage of TCR Vβ subtypes in CD3$^+$ T cells in PBMC and plasmid library by flow cytometry using Vβ subtype-specific antibodies. TCR Vβ usage in TCR-expressing retroviral library was investigated by infecting retroviral particles into TCR β chain-mutated J.RT3-T3.5 (J.RT3) Jurkat T-lymphoma subline (ATCC: TIB-153). J.RT3 was transduced with retroviral library at suboptimal viral titers that transduce less than 30% of cells to minimize multi-copy transduction. Expression of cell surface TCR Vβ was tested by flow cytometry using 24 different antibodies against Vβ subtypes. FIG. 3B shows the relationship between the frequency of each Vβ subtypes in CD3$^+$ T cells in PBMC and library-transduced J.RT3 for 3 independent libraries from different donors. Overall, Vβ usage in CD3$^+$ T cells was retained in the library. FIG. 3C compares mean percentages of Vβ usage with results of statistical analyses by paired t tests. Although there were a few significant differences in the Vβ usage between PBMC and TCR library such as overrepresentation of Vl35.1 in the library and several minor differences, the Vβ usage in peripheral T cells was well reproduced in the library. These results support that the majority of TCR gene species in the polyclonal T-cell population were PCR-amplified and assembled without significant bias.

Example 4

Identification of Tumor Antigen-Specific TCR Pairs from Tumor-Derived TCR-Expression Library Next, we tested whether a protocol of this disclosure could identify a tumor antigen-specific TCR gene from polyclonal T-cell population without isolating tumor antigen-specific T cells. It is known that immunogenic tumors are highly enriched by tumor antigen-specific T cells (J. Matsuzaki, et al. Proc. Natl. Acad. Sci. USA 107, 7875-7880 (2010)). Therefore, we analyzed whether randomly assembled TCR library from tumor specimens could be a valuable source to identify tumor antigen-specific TCR genes (FIG. 4A) Using a TCR amplification and assembly protocol described above, we a constructed TCR gene library from 3 frozen tumor specimens that were known to be infiltrated by high frequency HLA-Cw*03-restricted NY-ESO-1-specific $CD8^+$ T cells. TCR variable fragments were amplified from cDNA of frozen ovarian tumor specimens and assembled as retroviral plasmid vectors. Then, retroviral particles were produced using the bulk plasmid library.

Figure 4:
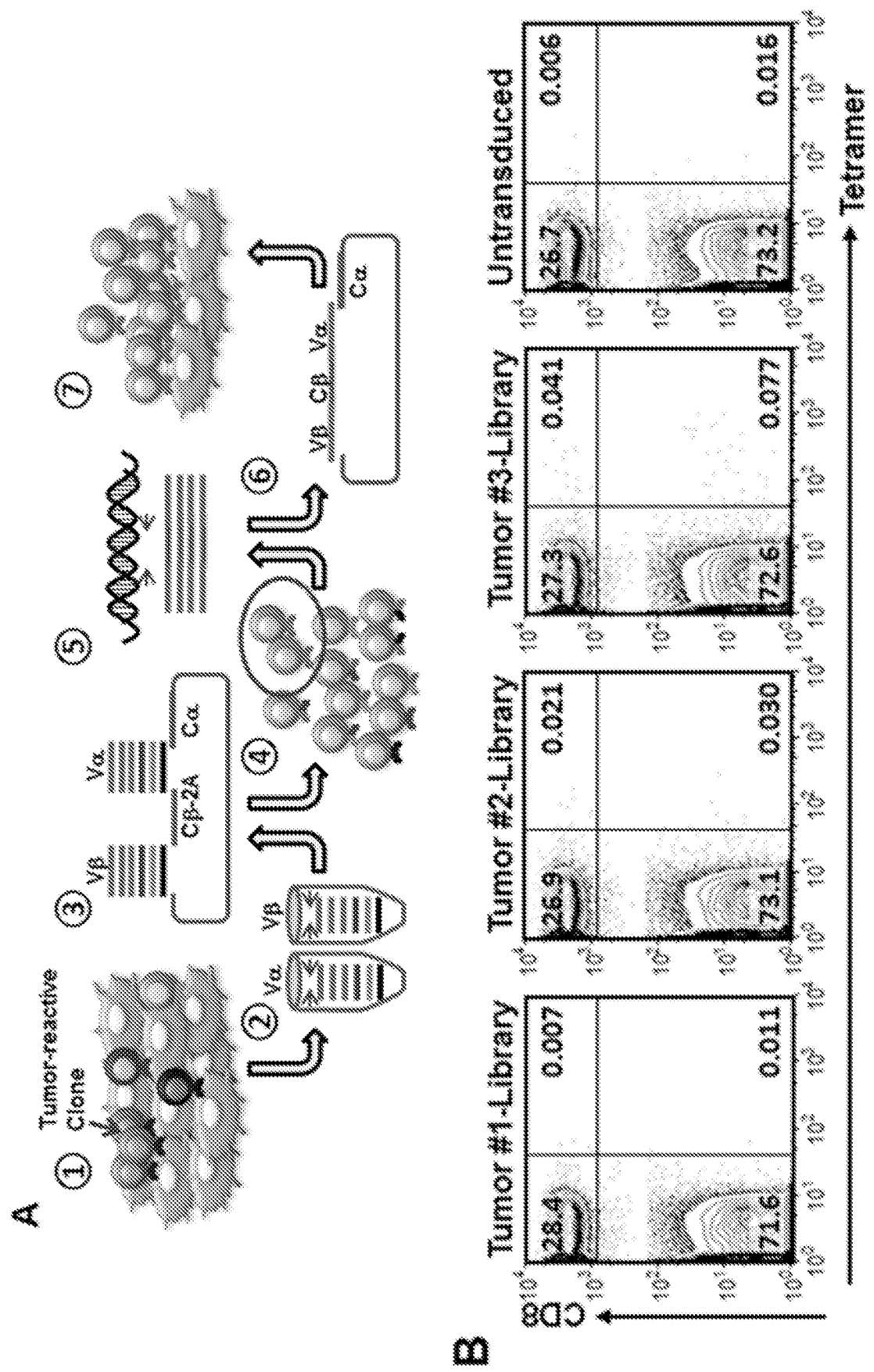
FIG. 4. Construction of tumor-derived TCR gene library. (A) Procedures for TCR gene library construction and screening. (1) Tumor specimens that are enriched with tumor-reactive T cells were selected for experiments. (2) TCR gene was amplified from cDNA and (3) randomly assembled into the destination plasmid vector together with β chain constant region-P2A fusion gene fragment. (4) Activated peripheral T cells from healthy individuals were transduced with the TCR library and sorted for tumor antigen-specificity using the MHC/peptide tetramer reagent. (5) TCR transgene was amplified from genomic DNA of the sorted tetramer-stained cells and (6) re-assembled into the destination vector. (7) Activated T cells were transduced by the secondary library and tested for tumor antigen-specificity. (B) Staining of TCR library-transduced T cells by HLA-Cw*03/NY-ESO-1 (92-100) tetramer. Activated T cells were transduced with tumor-derived TCR-expression retroviral library. Two days after transduction, cells were stained by the tetramer followed by CD8.
Figure 5:
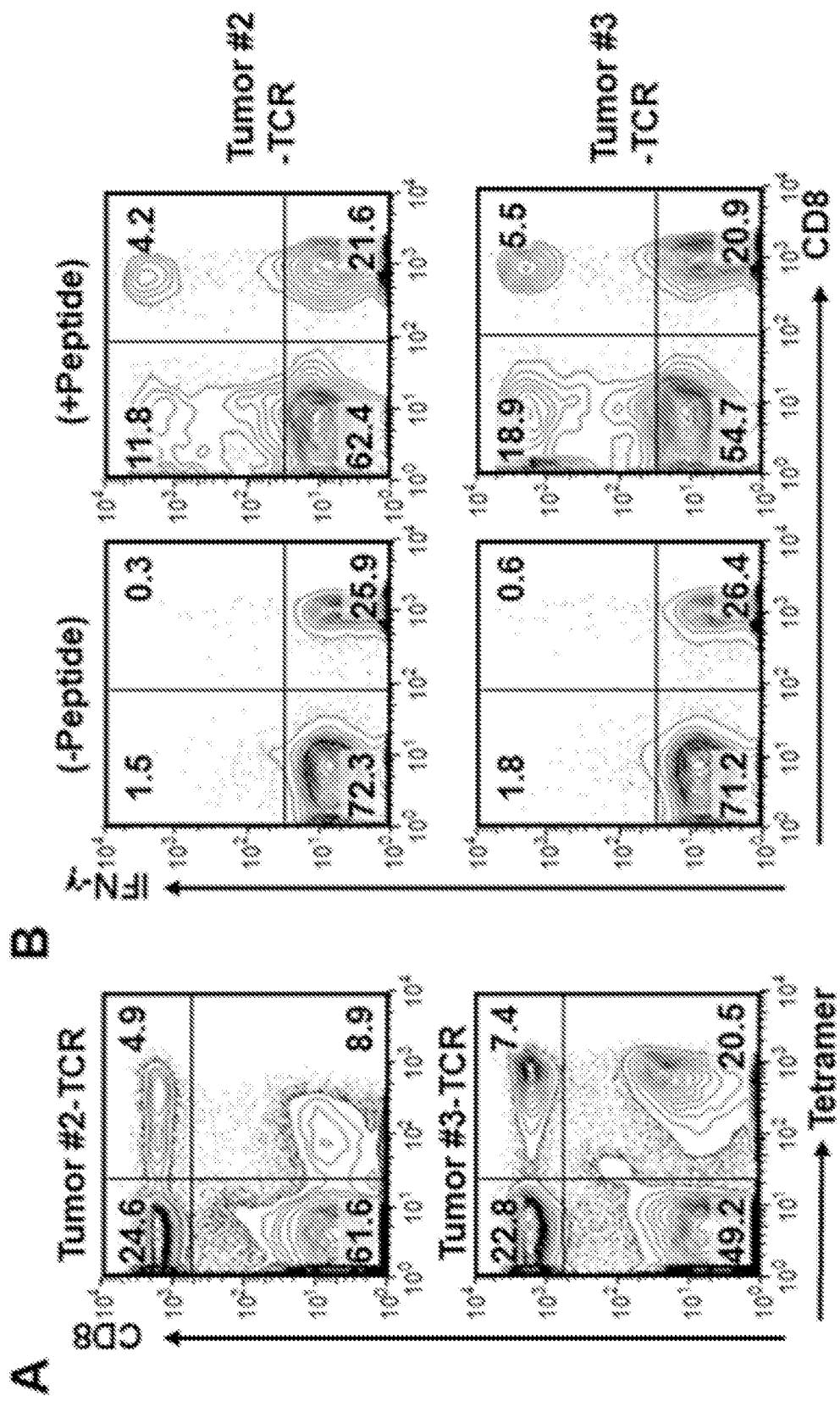
FIG. 5. Characterization of library-derived tumor antigen-specific TCR. (A) Tetramer staining of T cells transduced with the secondary TCR gene library. (B) Reactivity of the secondary TCR gene library-transduced T cells against the cognate peptide. Transduced T cells were cocultured with NY-ESO-1 (92-100) peptide-pulsed or unpulsed Cw*03+ target cells for 6 hours in the presence of Monensin and intracellularly stained for IFN-γ following cell surface CD8 staining. (C) Reactivity to cancer cells. Cw*03+NY-ESO-1+A2780 were treated with or without IFN-γ for 2 days and were used as target cells in intracellular IFN-γ staining of TCR gene-transduced T cells. (D) Therapeutic effect of secondary TCR gene library-transduced T cells. Cw*03+ NY-ESO-1+A2780 was treated in vitro with IFN-γ for 2 days and subcutaneously inoculated in NSG mice. On day 3, mice were infused with the secondary TCR library-transduced or untransduced T cells or untreated. Tumor growth was monitored by measuring tumor diameters. *: $p<0.05$ by the two-tailed t-test.
Figure 5:
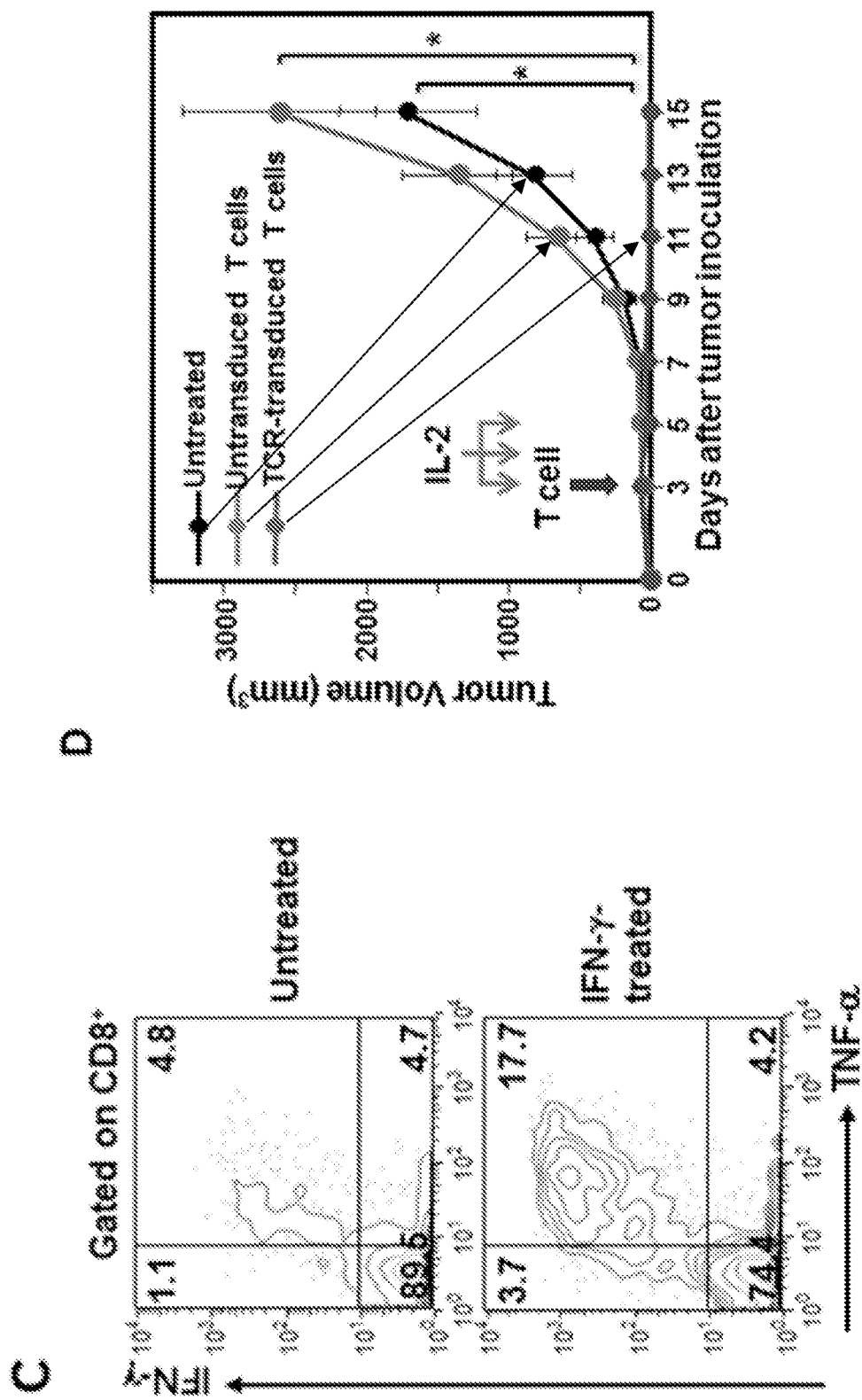
Figure 9:
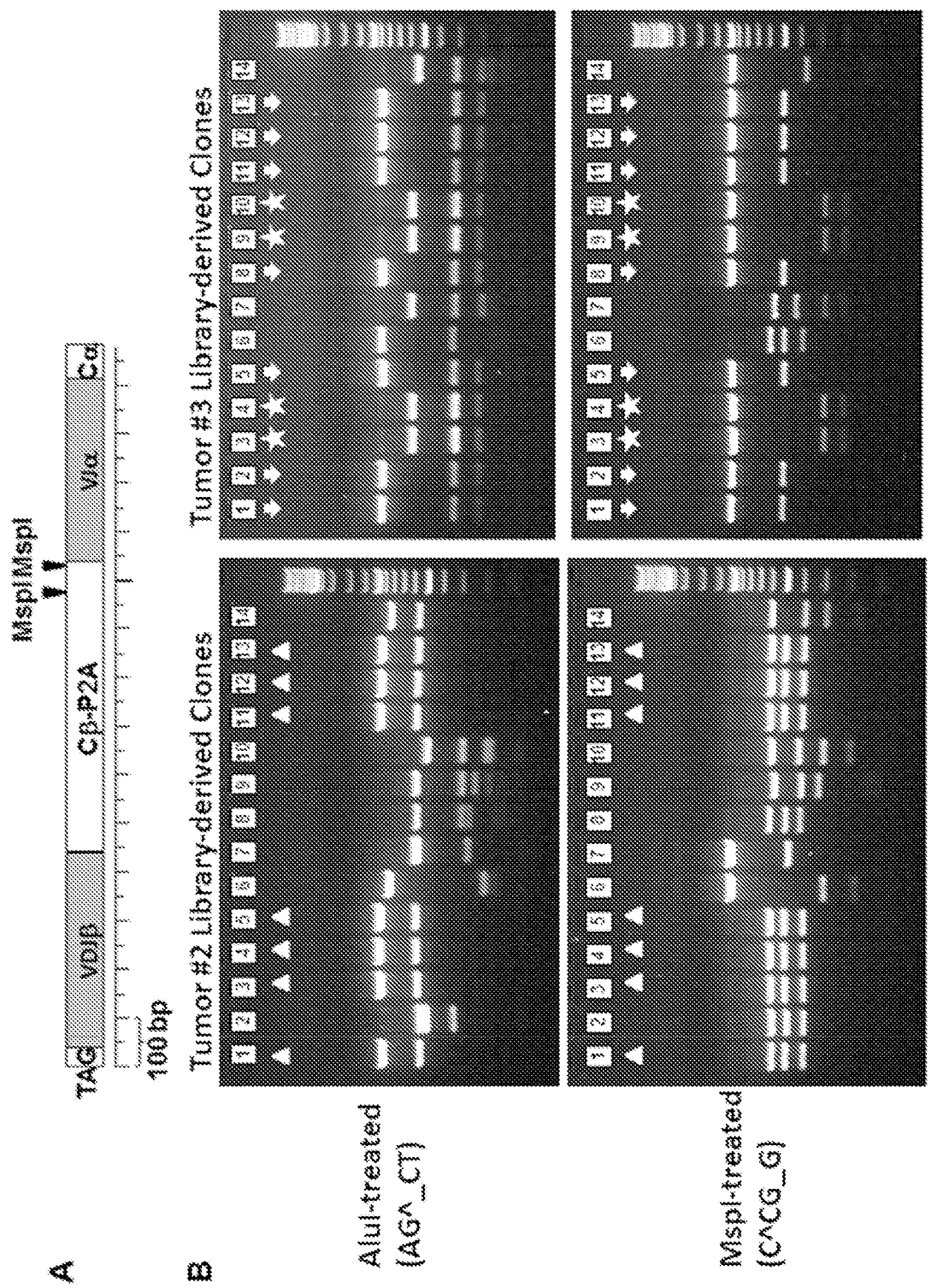
FIG. 9. Characterization of individual clones in the tumor-derived TCR-expressing secondary library. The secondary library was constructed from isolated tetramer+ T cells in T cells transduced by the primary library. E. coli competent cells were transformed by the secondary library plasmids. (A) TCR inserts in the clones were PCR amplified by HTTCR#A and HTTCR#E primers by colony PCR. In the DNA fragment shown, gray regions are derived from the T cells, while open regions are common regions. These common regions contain no AluI-recognizing site and two MspI-recognizing sites. (B) PCR amplicons in (A) were digested by the indicated restriction enzyme and agarose gel electrophoresed. Enriched clones were identified by the digestion patterns and identical clones were indicated by triangle, arrow and star symbols.
Figure 10:
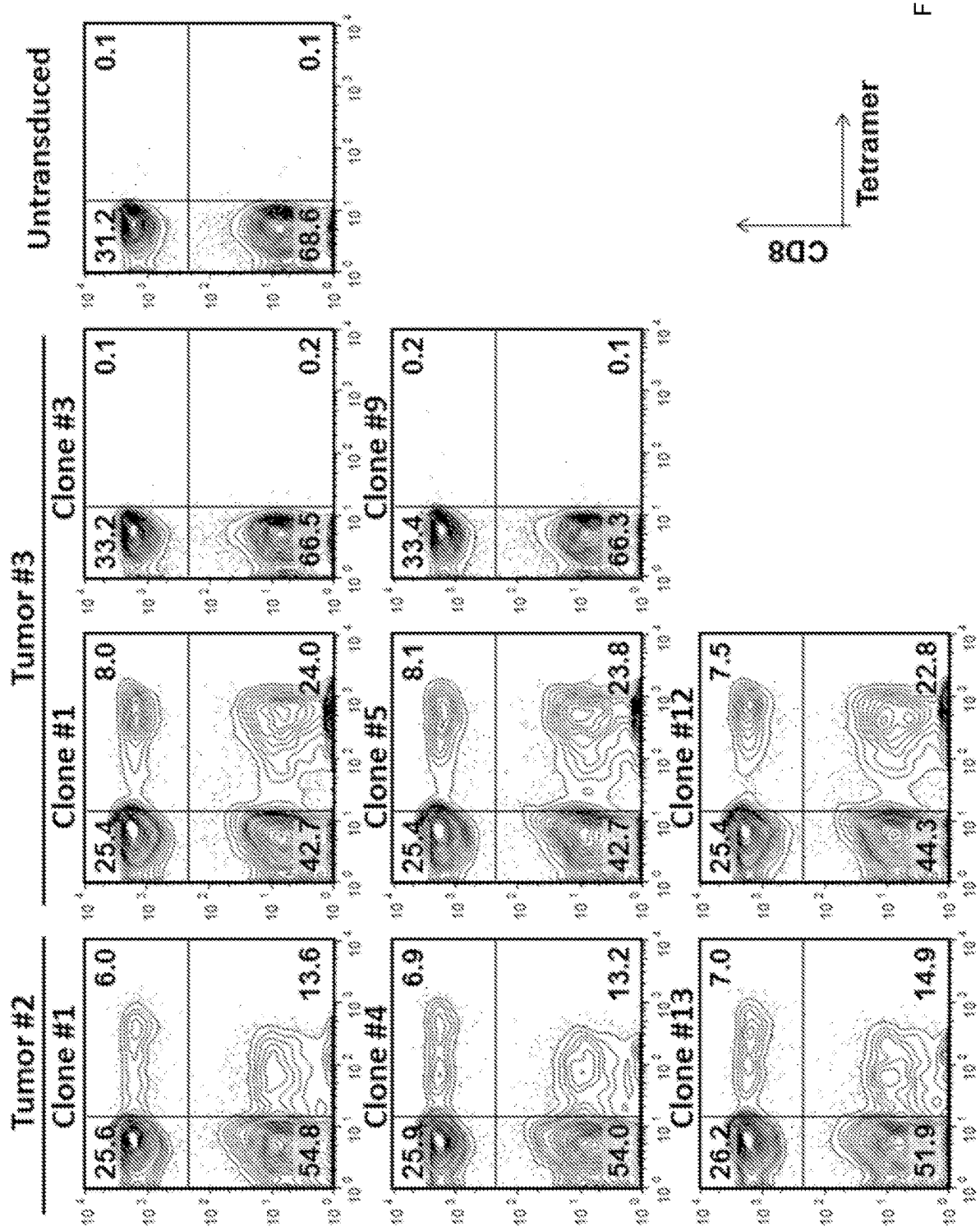
FIG. 10. Selection of NY-ESO-1-specific TCR clones from the secondary library. Identification of NY-ESO-1-specific TCR clones in the secondary library. Plasmids were isolated from selected clones in FIG. S4. Polyclonally activated T cells from healthy donor PBMC were transduced by retroviral vectors and stained with the HLA-Cw*03/NY-ESO-1 (92-100) tetramer.

Polyclonally activated T cells were infected once with tumor-derived TCR-expression library at suboptimal viral titers to minimize multi-copy transduction. As shown in FIG. 4B, significant increase in Cw*03/NY-ESO-1 tetramer-reactive $CD8^+$ and $CD4^+$ (which is $CD8^-$ cells) T cells compared to untransduced T cells was observed in 2 (#2 and #3) out of 3 libraries tested albeit at low frequencies because of random pairing. To isolate NY-ESO-1-specific TCR α and β chain genes, the tetramer-stained T cells were sorted by flow-cytometry and genomic DNA that were integrated by retroviral TCR transgene were extracted. TCR transgene was amplified by a nested PCR from genomic DNA and was re-assembled into TCR-expressing plasmid. This secondary TCR library was used to prepare retroviral vectors to transduce primary T cells. A large fraction of the secondary TCR library-transduced T cells were reactive to the cognate antigen, as demonstrated by specific tetramer staining (FIG. 5A) and cytokine release against specific peptide-pulsed target cells (FIG. 5B). These results demonstrated that even though frequencies of correctly paired TCR in the primary library are low, tumor antigen-specific TCR genes can be efficiently identified by isolation of TCR-transduced cells with desired functions, such as tetramer binding, and efficient PCR amplification of integrated TCR transgenes by nested PCR. TCR clones in the secondary library were characterized by TCR transgene DNA fingerprinting by digestion with restriction enzymes. As shown FIG. 9, the secondary TCR library for tumor #2 was significantly enriched by a single clone (7/14 clones), while tumor #3 was enriched with 2 clones (clonotype 3A: 7/14 and clonotype 3B: 4/14). Transduction with the enriched TCR clone from tumor #2 and the clonotype 3A but not 3B from tumor #3 induced $tetramer^+$ T cells. (FIG. 10).

We next investigated if a newly identified TCR would be ultimately functional and capable of rejecting tumors. We utilized an in vivo tumor xenograft model to study the therapeutic effect of the secondary TCR library-transduced T cells. Consistent with a recent report that NY-ESO-1 (92-100) epitope is generated by immunoproteasome (K. Woods, et al. J. Immunother. Cancer 4, 10 (2016).), in vitro recognition of A2780 ovarian cancer cell line (which was engineered to express Cw*03 and NY-ESO-1) by engineered T cells was significantly enhanced by IFN-γ treatment of cancer cells (FIG. 5C). NOD/SCID/common γ chain-deficient (NSG) mice were inoculated subcutaneously with HLA-Cw*03$^+$NY-ESO-1$^+$ A2780. On day 3 when palpable tumor was established, mice were intravenously infused with $4\times10^6$ TCR gene-transduced or untransduced T cells. While untransduced T cells showed no anti-tumor effects, TCR gene-transduced T-cell products completely eliminated established tumors in all animals (FIG. 5D).

Example 5

Materials and Methods

Specimens

Ovarian tumor specimens were obtained at the surgery at RPCI. A part of specimen was frozen in liquid nitrogen and stored at −80° C. Remaining specimens were minced by using scissors and the gentleMACS Dissociators (Miltenyi) and mononuclear cells were isolated by the density gradient method. Tumor single cell suspension was stored in 90% fetal bovine serum (FBS) and 10% dimethyl sulfoxide (DMSO) in a liquid nitrogen tank. Generation of NY-ESO-1-specific T cells was performed as described previously (J. Matsuzaki, et al. Proc. Natl. Acad. Sci. USA 107, 7875-7880 (2010)). Briefly, peripheral or tumor-infiltrating T cells from ovarian cancer patients, who had spontaneous immunity against NY-ESO-1 evidenced by the presence of serum anti-NY-ESO-1 autoantibodies, were in vitro stimulated with the NY-ESO-1 peptide(s) and cultured in the presence of 10 U/ml recombinant human (rh) IL-2 (Roche Diagnostics) and 10-20 ng/ml rhIL-7 (R&D Systems). Peptide-reactive T cells were identified by either staining with NY-ESO-1-specific tetramer reagents or IFN-γ secretion assay reagents (Miltenyi) and were isolated by cell sorting using FACSAriaII instrument. Cells were further expanded by stimulating with phytohemagglutinin (PHA; Remel) and irradiated allogeneic PBMCs in the presence of rhIL-2 and rhIL-7.

Total RNA from NY-ESO-1-specific T cells was obtained using TFI Reagent followed by Phenol/Chroloform extraction or the Direct-zol RNA MiniPrep kit (Zymo Research). Total RNA from tumor specimens (70-100 mg weight) was obtained by using tissue homogenizer in TRI Reagen followed by column purification with the Direct-zol RNA MiniPrep kit. Reverse transcription was performed using RevertAid First Strand cDNA Synthesis Kit using an oligo-dT primer (Thermo-Fisher).

PCR Amplification and Purification of TCR Variable Regions

Primer sequences were listed in Table 1. To provide tag-sequence for PCR amplification by tag-specific primers, cDNA was mixed with HTTCR#F for TCR α chain or HTTCR#C for TCR β chain in separate tubes in 1×Phusion polymerase reaction master mix (Thermo-Fisher). A single cycle of 98° C. for 40 seconds, rapid cooling to 72° C. then slow (−0.1° C./second) cooling to 66° C., 66° C. for 30 seconds and 72° C. for 5 minutes was performed to synthesize the second-strand DNA. Unused multiplexed primers and all single strand cDNA were destroyed by adding Exonuclease I and incubation at 37° C. for 15 minutes followed by inactivation at 85° C. for 15 minutes.

Each reaction was added with a tag-specific forward and TCR constant region-specific reverse primer pair, i.e., HTTCR#D and HTTCR#E for TCR α chain and HTTCR#A and HTTCR#B for TCR β chain in 1×Phusion polymerase reaction master mix. PCR was performed by 1 cycle of 98° C. for 30 seconds; 2 cycles of 98° C. for 10 seconds, 62° C. for 30 seconds, and 72° C. for 30 seconds; 30 cycles of 98° C. for 10 seconds and 72° C. for 60 seconds; and 1 cycle of 72° C. for 2 minutes. The reaction was load on 1% agarose gel containing SYBR Safe DNA Gel Stain (Thermo Fisher Scientific) and electrophored at 90V for 30 minutes. The main band of TCR variable fragments at around 450 bp was excised under the transilluminator (Invitrogen) and DNA fragments were extracted using Zymoclean Gel DNA Recovery Kit (Zymo Research). DNA concentration was measured by absorbance at 260 nm.

To amplify integrated TCR transgene from TCR gene-transduced T cells, genomic DNA from TCR-transduced T cells was mixed with vector-specific primer pairs amplifying the entire TCR expressing cassette (Forward: CGAATTCCCAAACTTAAGCTTGGTACCG (SEQ ID NO:114); and Reverse: GCAGCGTATCCACATAGCGTAAAAGG (SEQ ID NO:115) in 1×Phusion polymerase reaction mix. The PCR was performed by 1 cycle of 98° C. for 30 seconds; 35 cycles of 98° C. for 10 seconds, 71° C. for 30 seconds, and 72° C. for 40 seconds; and 1 cycle of 72° C. for 2 minutes. Then, 1 μl of the reaction was mixed with Vβ-tag-specific forward primer (HTTCR#A) and Cα-specific reverse primer (HTTCR#E) in 1×Phusion polymerase reaction mix and cycled for 1 cycle of 98° C. for 30 seconds; 35 cycles of 98° C. for 10 seconds and 72° C. for 70 seconds; and 1 cycle of 72° C. for 2 minutes. Amplified DNA fragments were isolated and quantified as described above.

Assembling of TCR Expressing Cassette into a Plasmid Vector.

A DNA fragment coding cysteine-modified TCR Cβ-P2A fusion protein was amplified by PCR from a plasmid containing this fragment and gel-purified. Description of the destination plasmid vector is provided in FIG. 6. Essentially, the destination plasmid was based on the MSCV retroviral vector with the modification of the splice acceptor site from human elongation factor 1a promoter before the TCR cloning site and contain cysteine-modified Cα fragment. The linearized destination plasmid (50 ng), which was treated with NotI and PspOMI and gel purified, was mixed with equimolar amount of Vβ, Cβ-P2A (obtained by PCR using HTTCR#F and HTTCR#G primers from the destination plasmid), Vα fragments in 10 μl 1×NEBuilder HiFi DNA Assembly Master Mix (New England Biolabs) and incubated at 50° C. for 60 minutes. To clone TCR expressing cassette amplified from genomic DNA of transduced T cells, linearized plasmid and TCR-expressing cassette insert was mixed at 1:2 molar ratio in 10 μl 1×NEBuilder HiFi DNA Assembly Master Mix and incubated at 50° C. for 60 minutes. The assembled product was used to transform chemically competent E. coli, NEBStable, after purification by DNA Clean & Concentrator kit (Zymo Research). Transformed E. coli was spread over three 10 cm agar plates and incubated 14-16 hours at 37° C. Confluent E. coli colonies in three plates were pooled and plasmids were purified by ZymoPURE Plasmid Midiprep Kit (Zymo Research). Quality of this bulk plasmid preparation was examined by restriction enzyme treatment with NotI and PacI which excise TCR expressing cassette from the plasmid backbone, followed by electrophoresis in an agarose gel.

In some experiments, plasmids obtained from pooled E. coli colonies were used to re-transform competent cells to obtain single colonies. A part of colonies were tested for DNA fingerprinting of TCR transgene by direct colony PCR using OneTaq (New England Biolabs) using a primer pair HTTCR#A and HTTCR#E and the reaction was treated with AluI or MspI restriction enzyme (Thermo Scientific).

Retroviral Transduction

Retroviral particles were produced by co-transfection of TCR-encoding transfer plasmids and pVSV-G envelope plasmids into the GP2-293 packaging cell line (Clontech) by Lipofectamine 2000 (Invitrogen-Thermo Scientific). Packaging cells were co-incubated with plasmids for 7 hours and culture medium was replaced. After 36 hours, supernatant was harvested, centrifuged for 5 minutes at 400×g for 5 minutes and immediately used for transduction of T cells.

PBMC were obtained from healthy donors' buffy coat using the density gradient method using lymphocyte separation medium and stored in a liquid nitrogen tank in 90% FBS plus 10% DMSO. PBMC were pre-activated by 10 μg/ml PHA for 40 hours in RPMI1640 medium supplemented with 10% FBS, Penicillin, Streptomycin and L-Glutamine in the presence of 10 U/ml rhIL-2 10 ng/ml rhIL-7, and 20 ng/ml rhIL-12p70 (Peprotech). Pre-activated PBMC ($1 \times 10^5$) were harvested, counted and plated on 96-well flat-bottom plate precoated overnight with 10 μg/ml Retronecting and 5 μg/ml anti-human CD3 monoclonal antibodies (mAb) (OKT3; eBioscience) in the presence of rhIL-2, rhIL-7 and rhIL-12. Typically, 125 μl retroviral supernatant was added to transduce T cells and culture for 24 hours. Cells were expanded in the presence of rhIL-2 and rhIL-7 without rhIL-12 and used for evaluation within 7 days after transduction. Transduction of Jurkat (E6-1; ATCC) or J.RT3-T3.5 (ATCC) was performed similarly but without activating reagents and cytokines and using reduced volumes of retroviral supernatant.

Detection and Isolation of Antigen-Specific T Cells

NY-ESO-1-specific T cells were detected by specific MHC/peptide tetramer reagent (Ludwig Center for Cancer Research, University of Lausanne). TCR gene-transduced T cells were washed in PBS containing 1% FBS and incubated at 37° C. for 15 minutes in the presence of 6 μg/ml phycoerythrin (PE)-conjugated tetramer in 1% FBS-PBS. Cells were then stained by allophycocyanin (APC)-conjugated anti-CD4 mAb and PerCP/Cy5.5-conjugated anti-CD8 mAb (Biolegend) at 4° C. for 15 minutes. Fluorescent signals were acquired by FACSCalibur instrument and analyzed by FlowJo software. In some experiments, tetramer$^+$ T cells were sorted using FACSAria instrument. Genomic DNA of sorted cells was obtained using Quick-gDNA MicroPrep kit (Zymo Research).

Cytokine production from TCR gene-transduced T cells was tested by intracellular cytokine staining. Target cells were NY-ESO-1-expressing melanoma cell lines (HLA-A*02$^+$DRB1*01$^+$DPB1*04$^+$SK-MEL-37; HLA-B*35$^+$ SK-MEL-52; HLA-DRB1*04$^+$DP*04$^+$ COLO 316 retrovirally transduced with NY-ESO-1 and CIITA genes) or NY-ESO-1-negative HLA-Cw*03$^+$ MZ-MEL-12. To test Cw*03-restricted NY-ESO-1-specific reactivity, a Cw*03-negative and NY-ESO-1-negative A2780 ovarian cancer cell line was engineered by the Sleeping Beauty transposon system. Cw*03 and NY-ESO-1 co-expressing transposon plasmid was constructed by inserting human elongation factor 1α promoter followed by Cw*03-P2A-EGFP(A206K)-T2A-NY-ESO-1 expressing cassette into pT2/BH (Addgene plasmid #26556). A2780 was nucleofected using the 4D-Nucleofector system (Lonza) with pCMV(CAT)T7-SB100 (Addgene plasmid #34879) and pT2-EF-Cw3-GFP-ESO. GFP$^+$ clones were obtained by limiting dilution. To induce immunoproteasome expression in Cw*03$^+$NY-ESO-1$^+$ A2780, cells were pre-treated with 1,000 U/ml rhIFN-γ (Peprotech) for 2 days. Before co-culture with T cells, target cells were unpulsed or pulsed overnight with 10 μg/ml synthetic NY-ESO-1 peptide (Genscript) or 10 μg/ml recombinant NY-ESO-1 protein (Ludwig Institute for Cancer Research) and extensively washed in RPMI1640 medium. T cells were cocultured with target cells for 6 hours in the presence of GolgiStop (BD Biosciences). Cells were stained by fluorescein isothiocyanate (FITC)-conjugated anti-CD4 and PerCP/Cy5.5-conjugated anti-CD8 mAbs, permeabilized using BD Cytofix/Cytoperm Plus Fixation/Permeabilization Kit (BD Biosciences), and stained with PE-conjugated anti-TNF-α and APC-conjugated anti-IFN-γ mAbs (BioLegend). Cells were analyzed by FACSCalibur instrument and FlowJo software.

Tumor Xenograft Model

NSG mice (Jackson Laboratory) were bred at the Laboratory Animal Resource at RPCI. Mice were inoculated with $1 \times 10^6$ IFN-γ-treated Cw3$^+$NY-ESO-1$^+$ A2780. Therapeutic T cells were generated by retroviral transduction of the Cw*03-restricted NY-ESO-1 (92-100)-specific secondary TCR library (Tumor #3). On day 3, mice received $4 \times 10^6$ TCR-transduced or untransduced T cells, or untreated. On days 3-5, all T cell-infused animals were intraperitoneally injected with $5 \times 10^4$ IL-2 (Peprotech). Tumor growth was measured every other day. Tumor volume was calculated by a formula 0.5×(longer diameter)×(shorter diameter). Animals were sacrificed when tumor volume reached 2,000 mm$^3$.

Statistical Analysis

Student's t-test was used to evaluate statistically significant differences between the values in two groups.

Although the invention has been described in detail for the purposes of illustration, it is understood that such detail is solely for that purpose, and variations can be made therein by those skilled in the art without departing from the spirit and scope of the invention which is defined by the following claims, which are intended to illustrate embodiments of the disclosure but are not meant to be limiting.

What is claimed is:

1. A method for cloning a plurality of TCR α and β chain variable sequences from T-cell receptors (TCRs) from an oligoclonal population of T cells, the method comprising:
 1) obtaining RNA from the oligoclonal population of T cells, wherein the RNA comprises mRNA encoding the TCR α and β chain variable sequences, and generating first single strand cDNA from the mRNA, wherein the first single strand cDNA includes single stranded cDNA encoding the TCR α chains and single stranded cDNA encoding the TCR β chains, wherein the single stranded cDNAs are generated using reverse transcription and oligo-dT primers, to obtain a sample of first strand cDNA amplified from the mRNA;
 2) Dividing the sample from 1) into first and second samples and performing polymerase chain reactions (PCR) reactions comprising:
 in the first sample a second-strand cDNA synthesis to obtain double stranded cDNA amplicons encoding the TCR β chains using all of the primers:

| | | |
|---|---|---|
| HTTCR#C-1 | CGGCCGCCACCATGGATACCTGGCTCGTATGCTG | SEQ ID NO: 3 |
| HTTCR#C-2 | CGGCCGCCACCATGGATACCTGGCTGTATGCTGG | SEQ ID NO: 4 |
| HTTCR#C-3 | CGGCCGCCACCATGGGCTGCAGGCTCCT | SEQ ID NO: 5 |
| HTTCR#C-4 | CGGCCGCCACCATGGGCTTCAGGCTCCTCT | SEQ ID NO: 6 |
| HTTCR#C-5 | CGGCCGCCACCATGGGCTGCAGGCTGC | SEQ ID NO: 7 |
| HTTCR#C-6 | CGGCCGCCACCATGGGCTCCAGGCTGCT | SEQ ID NO: 8 |
| HTTCR#C-7 | CGGCCGCCACCATGGGCCCTGGGCTC | SEQ ID NO: 9 |
| HTTCR#C-8 | CGGCCGCCACCATGGGCCCCGGGC | SEQ ID NO: 10 |
| HTTCR#C-9 | CGGCCGCCACCATGGGACCCAGGCTCCT | SEQ ID NO: 11 |
| HTTCR#C-10 | CGGCCGCCACCATGAGCATCGGGCTCCTGT | SEQ ID NO: 12 |
| HTTCR#C-11 | CGGCCGCCACCATGAGCCTCGGGCTCCT | SEQ ID NO: 13 |
| HTTCR#C-12 | CGGCCGCCACCATGAGAATCAGGCTCCTGTGCTG | SEQ ID NO: 14 |
| HTTCR#C-13 | CGGCCGCCACCATGAGCATCAGGCTCCTGTGC | SEQ ID NO: 15 |
| HTTCR#C-14 | CGGCCGCCACCATGAGCATCGGCCTCCTGT | SEQ ID NO: 16 |
| HTTCR#C-15 | CGGCCGCCACCATGAGCATCAGCCTCCTGTGC | SEQ ID NO: 17 |
| HTTCR#C-16 | CGGCCGCCACCATGGGCACCAGGCTCCT | SEQ ID NO: 18 |
| HTTCR#C-17 | CGGCCGCCACCATGGGCACCAGTGTCCTATGT | SEQ ID NO: 19 |
| HTTCR#C-18 | CGGCCGCCACCATGGGCACCAGTCTCCTATGC | SEQ ID NO: 20 |
| HTTCR#C-19 | CGGCCGCCACCATGGGTACCAGTCTCCTATGCTGG | SEQ ID NO: 21 |
| HTTCR#C-20 | CGGCCGCCACCATGGGCACCAGCCTCCT | SEQ ID NO: 22 |

```
                         SEQ ID NO: 23
HTTCR#C-21  CGGCCGCCACCATGGGGACCAGCCTCCT

SEQ ID NO: 24
HTTCR#C-22  CGGCCGCCACCATGGCCCTGTGTCTCCTGG

SEQ ID NO: 25
HTTCR#C-23  CGGCCGCCACCATGGGCACGAGGCTCTTCT

SEQ ID NO: 26
HTTCR#C-24  CGGCCGCCACCATGGGCACCAGGCTCTTCT

SEQ ID NO: 27
HTTCR#C-25  CGGCCGCCACCATGTGGCCCTTTGTCTGCTGT

SEQ ID NO: 28
HTTCR#C-26  CGGCCGCCACCATGGGCACAAGGTTGTTCTTCTATGT

SEQ ID NO: 29
HTTCR#C-27  CGGCCGCCACCATGAGCACCAGGCTTCTCTGC

SEQ ID NO: 30
HTTCR#C-28  CGGCCGCCACCATGGGTACCAGGCTCCTCTG

SEQ ID NO: 31
HTTCR#C-29  CGGCCGCCACCATGGACTCCTGGACCTTCTGC

SEQ ID NO: 32
HTTCR#C-30  CGGCCGCCACCATGGACTCCTGGACCCTCTG

SEQ ID NO: 33
HTTCR#C-31  CGGCCGCCACCATGGGCTCCTGGACCCTC

SEQ ID NO: 34
HTTCR#C-32  CGGCCGCCACCATGGCCACCAGGCTCCT

SEQ ID NO: 35
HTTCR#C-33  CGGCCGCCACCATGCTTAGTCCTGACCTGCTG

SEQ ID NO: 36
HTTCR#C-34  CGGCCGCCACCATGGTTTCCAGGCTTCTCAGTTTAGTG

SEQ ID NO: 37
HTTCR#C-35  CGGCCGCCACCATGGGTCCTGGGCTTCTCC

SEQ ID NO: 38
HTTCR#C-36  CGGCCGCCACCATGAGCCCAATATTCACCTGCATCA

SEQ ID NO: 39
HTTCR#C-37  CGGCCGCCACCATGGACACCAGAGTACTCTGCTG

SEQ ID NO: 40
HTTCR#C-38  CGGCCGCCACCATGAGCAACCAGGTGCTCTG

SEQ ID NO: 41
HTTCR#C-39  CGGCCGCCACCATGCTGCTGCTTCTGCTGC

SEQ ID NO: 42
HTTCR#C-40  CGGCCGCCACCATGGCCTCCCTGCTCTTCT

SEQ ID NO: 43
HTTCR#C-41  CGGCCGCCACCATGACTATCAGGCTCCTCTGCTACA

SEQ ID NO: 44
HTTCR#C-42  CGGCCGCCACCATGGGCCCCAGCTC

SEQ ID NO: 45
HTTCR#C-43  CGGCCGCCACCATGGGAATCAGGCTCCTCTGTC

SEQ ID NO: 46
HTTCR#C-44  CGGCCGCCACCATGCTGAGTCTTCTGCTCCTTCTC

SEQ ID NO: 47
HTTCR#C-45  CGGCCGCCACCATGATGCTCTGCTCTCTCCTTGC

SEQ ID NO: 50
HTTCR#F-1   AACCCCGGTCCCATGTGGGGAGCTTTCCTTCTCTATG

SEQ ID NO: 51
HTTCR#F-2   AACCCCGGTCCCATGTGGGGAGTTTTCCTTCTTTATG
            TTTCC

SEQ ID NO: 52
HTTCR#F-3   AACCCCGGTCCCATGGCTTTGCAGAGCACTCTG

SEQ ID NO: 53
HTTCR#F-4   AACCCCGGTCCCATGGCCTCTGCACCCATCT

SEQ ID NO: 54
HTTCR#F-5   AACCCCGGTCCCATGAGGCAAGTGGCGAGAGT

SEQ ID NO: 55
HTTCR#F-6   AACCCCGGTCCCATGAAGACATTTGCTGGATTTTCGT
            TCCT

SEQ ID NO: 56
HTTCR#F-7   AACCCCGGTCCCATGGAGTCATTCCTGGGAGGTG

SEQ ID NO: 57
HTTCR#F-8   AACCCCGGTCCCATGGAGTCATCCCTGGGAGG

SEQ ID NO: 58
HTTCR#F-9   AACCCCGGTCCCATGGAGAAGATGCGGAGACCTG

SEQ ID NO: 59
HTTCR#F-10  AACCCCGGTCCCATGCTCCTGTTGCTCATACCAGT

SEQ ID NO: 60
HTTCR#F-11  AACCCCGGTCCCATGCTCCTGCTGCTCGTCC

SEQ ID NO: 61
HTTCR#F-12  AACCCCGGTCCCATGCTCCTGGAGCTTATCCCAC

SEQ ID NO: 62
HTTCR#F-13  AACCCCGGTCCCATGAATTCTTCTCTAGGACCAGCGA
            TT

SEQ ID NO: 63
HTTCR#F-14  AACCCCGGTCCCATGAACTATTCTCCAGGCTTAGTAT
            CTCTGATACT

SEQ ID NO: 64
HTTCR#F-15  AACCCCGGTCCCATGAAAAAGCATCTGACGACCTTCT
            TGG

SEQ ID NO: 65
HTTCR#F-16  AACCCCGGTCCCATGATGATATCCTTGAGAGTTTTAC
            TGGTGATCC

SEQ ID NO: 66
HTTCR#F-17  AACCCCGGTCCCATGATGAAATCCTTGAGAGTTTTAC
            TAGTGATCCT

SEQ ID NO: 67
HTTCR#F-18  AACCCCGGTCCCATGATGAAATCCTTGAGAGTTTTAC
            TGGTGATCC

SEQ ID NO: 68
HTTCR#F-19  AACCCCGGTCCCATGATGAAATCCTTGAGAGTTTTAC
            TGGTCATCC

SEQ ID NO: 69
HTTCR#F-20  AACCCCGGTCCCATGACATCCATTCGAGCTGTATTTA
            TATTCCTGT
``` in the second sample a second-strand cDNA synthesis to obtain double stranded cDNA amplicons encoding the TCR α chains using all of the primers:

| | | |
|---|---|---|
| HTTCR#F-21 | SEQ ID NO: 70 | AACCCCGGTCCCATGATGGCAGGCATTCGAGTTTTATTTATGTAC |
| HTTCR#F-22 | SEQ ID NO: 71 | AACCCCGGTCCCATGTCACTTTCTAGCCTGCTGAAGG |
| HTTCR#F-23 | SEQ ID NO: 72 | AACCCCGGTCCCATGAAGCCCACCCTCATCTCAG |
| HTTCR#F-24 | SEQ ID NO: 73 | AACCCCGGTCCCATGGAAACTCTCCTGGGAGTGTC |
| HTTCR#F-25 | SEQ ID NO: 74 | AACCCCGGTCCCATGCTGTCTGCTTCCTGCTCA |
| HTTCR#F-26 | SEQ ID NO: 75 | AACCCCGGTCCCATGAACATGCTGACTGCCAGC |
| HTTCR#F-27 | SEQ ID NO: 76 | AACCCCGGTCCCATGGAGAAAATGTTGGAGTGTGCATTCA |
| HTTCR#F-28 | SEQ ID NO: 77 | AACCCCGGTCCCATGGAGACCCTCTTGGGCC |
| HTTCR#F-29 | SEQ ID NO: 78 | AACCCCGGTCCCATGAAGAGGATATTGGGAGCTCTGC |
| HTTCR#F-30 | SEQ ID NO: 79 | AACCCCGGTCCCATGGACAAGATCTTAGGAGCATCATTTTTAGTTCT |
| HTTCR#F-31 | SEQ ID NO: 80 | AACCCCGGTCCCATGGAGAAGAATCCTTTGGCAGCC |
| HTTCR#F-32 | SEQ ID NO: 81 | AACCCCGGTCCCATGCTACTCATCACATCAATGTTGGTCTTATG |
| HTTCR#F-33 | SEQ ID NO: 82 | AACCCCGGTCCCATGAGGCTGGTGGCAAGAGTAA |
| HTTCR#F-34 | SEQ ID NO: 83 | AACCCCGGTCCCATGAGGTTGGTGACAAGCATTACTGTAC |
| HTTCR#F-35 | SEQ ID NO: 84 | AACCCCGGTCCCATGAAGTTGGTGACAAGCATTACTGTACTC |
| HTTCR#F-36 | SEQ ID NO: 85 | AACCCCGGTCCCATGGTCCTGAAATTCTCCGTGTCC |
| HTTCR#F-37 | SEQ ID NO: 86 | AACCCCGGTCCCATGGCCATGCTCCTGGG |
| HTTCR#F-38 | SEQ ID NO: 87 | AACCCCGGTCCCATGGAGACTCTCCTGAAAGTGCTTTC |
| HTTCR#F-39 | SEQ ID NO: 88 | AACCCCGGTCCCATGGAGACTCTCCTGAAAGTGCC |
| HTTCR#F-40 | SEQ ID NO: 89 | AACCCCGGTCCCATGGAGACTGTTCTGCAAGTACTCC |
| HTTCR#F-41 | SEQ ID NO: 90 | AACCCCGGTCCCATGCTCCTTGAACATTTATTAATAATCTTGTGGATGC |
| HTTCR#F-42 | SEQ ID NO: 91 | AACCCCGGTCCCATGATGAAGTGTCCGCAGGCT |
| HTTCR#F-43 | SEQ ID NO: 92 | AACCCCGGTCCCATGATGAAGTGTCCACAGGCTTTACT |
| HTTCR#F-44 | SEQ ID NO: 93 | AACCCCGGTCCCATGACACGAGTTAGCTTGCTGTG |
| HTTCR#F-45 | SEQ ID NO: 94 | AACCCCGGTCCCATGACACCAGTTAGCTTGCTGTG |
| HTTCR#F-46 | SEQ ID NO: 95 | AACCCCGGTCCCATGGCATGCCCTGGCTT |
| HTTCR#F-47 | SEQ ID NO: 96 | AACCCCGGTCCCATGAAGAAGCTACTAGCAATGATTCTGTGG |
| HTTCR#F-48 | SEQ ID NO: 97 | AACCCCGGTCCCATGAACTCCTCTCTGGACTTTCTAATTCTGA |
| HTTCR#F-49 | SEQ ID NO: 98 | AACCCCGGTCCCATGGTGAAGATCCGGCAATTTTTGTTG |

3) incubating the first and second samples with an exonuclease for a period of time sufficient to degrade primers that were not incorporated into the amplicons and single stranded cDNA if present, and subsequently inactivating the exonuclease using a heat treatment;

4) performing in the first sample a PCR amplification of the amplicons encoding the TCR β chains using tag-specific primer HTTCR #A-ACT-TAAGCTTGGTACCGAGCTCG-GATCTGCGGCCGCCACCATG (SEQ ID NO:1) and primer HTTCR#B-CT-CAAACACAGCGACCTCGGGTGGGAACAC (SEQ ID NO:2) to obtain amplicons encoding the TCR β chains, wherein the amplicons encoding the TCR β chains further comprise a restriction endonuclease recognition site, a Kozak sequence and a translation initiating ATG sequence;

performing in the second sample a PCR amplification of the amplicons encoding the TCR α chains using tag-specific primer HTTCR #D GGAGACGTG-GAAGAAAACCCCGGTCCCATG (SEQ ID NO:48) and HT-TCR#E AGGCAGACAGACTTGTCACTG-GATTTAGAG (SEQ ID NO:49) to obtain amplicons encoding the TCR α chains, wherein the amplicons comprising the TCR α chains further comprise a P2A sequence and an initiating ATG sequence; and 5) assembling the amplicons encoding the TCR β chains and the TCR α chains from 4) into DNA vectors to provide a plurality of DNA vectors each comprising DNA segments encoding only one of the TCR β chains and only one of the TCR α chains, wherein the vectors comprise a Cα-2A fusion segment between segments encoding the TCR β chain and the TCR α chain, thereby providing a plurality of DNA vectors, each vector in the plurality encoding only a single TCR β chain and a single TCR α chain from the TCRs from the oligoclonal population of T cells.

2. The method of claim 1, wherein the oligoclonal population of T cells is obtained from a cancer tumor.

3. The method of claim 2, wherein the tumor comprises bladder, brain, breast, ovarian, lung, renal, colon, stomach, pancreas, prostate or liver cancer, myeloma, a sarcoma, a tumor formed from leukemia, lymphoma, or a melanoma, and/or wherein the tumor comprises cancer cells that express immunogenic tumor antigens comprising at least one of NY-ESO-1, WT1, MUC1, LMP2, HPV E6 and E7, EGFRvIII, HER2/neu, MAGE-A3, p53, NY-ESO-1, PSMA, GD2, CEA, MalanA/MART1, mutated Ras, gp100, Proteinase 3, bcr-abl, Tyrosinase, Survivin, PSA, hTERT, MAGE-A1, MAGE-A4, MAGE-C1, MAGE-C2, PLAC1, Sp17, TRP-2, Cyclin B1, Mesothelin, Folate Receptor alpha, and patient specific neoantigens.

4. The method of claim 2, wherein the DNA vectors of 5) are capable of expressing the TCR α and the TCR β chains in lymphocytes such that the lymphocytes exhibit antigen specificity against an antigen expressed by the cancer tumor.

5. The method of claim 2, comprising introducing into lymphocytes at least one of the DNA vectors of 5) and allowing expression of the TCR β chain and the TCR α chain encoded by the at least one vector such that the lymphocytes express a functional TCR comprising the TCR β chain and the TCR α chain.

6. The method of claim 2, comprising introducing into lymphocytes at least one of the DNA vectors of 5), allowing expression of the TCR β chain and the TCR α chain encoded by the at least one vector, and subsequently exposing the lymphocytes comprising the at least one DNA vector to cancer cells of the same type of cancer as the cancer tumor, and determining whether or not the lymphocytes exhibit antigen specificity against an antigen expressed by the cancer cells.

7. The method of claim 6, further comprising determining that the lymphocytes exhibit antigen specificity against an antigen expressed by the cancer cells.

8. The method of claim 7, wherein the cancer cells comprise bladder, brain, breast, ovarian, lung, renal, colon, stomach, pancreas, prostate or liver cancer cells, myeloma cells, sarcoma cells, cells from a tumor formed from leukemia, lymphoma, or cells from a melanoma, and/or wherein cancer cells express immunogenic tumor antigens comprising at least one of NY-ESO-1, WT1, MUC1, LMP2, HPV E6 and E7, EGFRvIII, HER2/neu, MAGE-A3, p53, NY-ESO-1, PSMA, GD2, CEA, MalanA/MART1, mutated Ras, gp100, Proteinase 3, bcr-abl, Tyrosinase, Survivin, PSA, hTERT, MAGE-A1, MAGE-A4, MAGE-C1, MAGE-C2, PLAC1, Sp17, TRP-2, Cyclin B1, Mesothelin, Folate Receptor alpha, or a patient specific neoantigen.

9. The method of claim 1, wherein at least some of the DNA vectors in the plurality of DNA vectors encode a TCR β chain and TCR α chain combination that is not expressed by any of the T cells in the oligoclonal population of T cells.

10. The method of claim 9, further comprising introducing into lymphocytes at least one of the DNA vectors, allowing expression of the TCR β chain and the TCR α chain encoded by the at least one vector, and subsequently exposing the lymphocytes comprising the at least one DNA vector to cancer cells of the same type of cancer as a cancer tumor from which the oligoclonal population of T cells was obtained, and determining whether or not the lymphocytes exhibit antigen specificity against an antigen expressed by the cancer cells, and optionally further determining whether or not the lymphocytes exhibit antigen specificity against an antigen expressed by non-cancer cells.

11. A lymphocyte comprising at least one DNA vector made according to the method of claim 1 for making the plurality of DNA vectors.

12. The lymphocyte of claim 11, wherein the lymphocyte is a CD4+ lymphocyte, or a CD8+ lymphocyte.

13. The lymphocyte of claim 12, wherein the lymphocyte expresses the TCR β chain and the TCR α chain in a functional TCR, wherein the lymphocyte exhibits antigen specificity to cancer selected from bladder, brain, breast, ovarian, lung, renal, colon, stomach, pancreas, prostate, or liver cancer, myeloma, a sarcoma, a tumor formed from leukemia, lymphoma, or a melanoma.

14. The lymphocyte of claim 12, wherein the lymphocyte expresses the TCR β chain and the TCR α chain encoded by the at least one vector in a functional TCR, wherein the lymphocyte exhibits antigen specificity to at least one of NY-ESO-1, WT1, MUC1, LMP2, HPV E6 and E7, EGFRvIII, HER2/neu, MAGE-A3, p53, NY-ESO-1, PSMA, GD2, CEA, MalanA/MART1, mutated Ras, gp100, Proteinase 3, bcr-abl, Tyrosinase, Survivin, PSA, hTERT, MAGE-A1, MAGE-A4, MAGE-C1, MAGE-C2, PLAC1, Sp17, TRP-2, Cyclin B1, Mesothelin, Folate Receptor alpha, or a patient specific neoantigen.

15. A kit comprising all of the primers: HTTCR #A (ACTTAAGCTTGGTACCGAGCTCG-GATCTGCGGCCGCCACCATG; SEQ ID NO:1) and:

```
HTTCR#C-1    CGGCCGCCACCATGGATACCTGGCTCGTATGCTG        SEQ ID NO: 3
HTTCR#C-2    CGGCCGCCACCATGGATACCTGGCTGTATGCTGG       SEQ ID NO: 4
HTTCR#C-3    CGGCCGCCACCATGGGCTGCAGGCTCCT             SEQ ID NO: 5
HTTCR#C-4    CGGCCGCCACCATGGGCTTCAGGCTCCTCT           SEQ ID NO: 6
HTTCR#C-5    CGGCCGCCACCATGGGCTGCAGGCTGC              SEQ ID NO: 7
HTTCR#C-6    CGGCCGCCACCATGGGCTCCAGGCTGCT             SEQ ID NO: 8
HTTCR#C-7    CGGCCGCCACCATGGGCCCTGGGCTC               SEQ ID NO: 9
HTTCR#C-8    CGGCCGCCACCATGGGCCCCGGGC                 SEQ ID NO: 10
HTTCR#C-9    CGGCCGCCACCATGGGACCCAGGCTCCT             SEQ ID NO: 11
HTTCR#C-10   CGGCCGCCACCATGAGCATCGGGCTCCTGT           SEQ ID NO: 12
HTTCR#C-11   CGGCCGCCACCATGAGCCTCGGGCTCCT             SEQ ID NO: 13
HTTCR#C-12   CGGCCGCCACCATGAGAATCAGGCTCCTGTGCTG       SEQ ID NO: 14
HTTCR#C-13   CGGCCGCCACCATGAGCATCAGGCTCCTGTGC         SEQ ID NO: 15
HTTCR#C-14   CGGCCGCCACCATGAGCATCGGCCTCCTGT           SEQ ID NO: 16
HTTCR#C-15   CGGCCGCCACCATGAGCATCAGCCTCCTGTGC         SEQ ID NO: 17
HTTCR#C-16   CGGCCGCCACCATGGGCACCAGGCTCCT             SEQ ID NO: 18
HTTCR#C-17   CGGCCGCCACCATGGGCACCAGTGTCCTATGT         SEQ ID NO: 19
```

| | | SEQ ID NO: 20 |
|---|---|---|
| HTTCR#C-18 | CGGCCGCCACCATGGGCACCAGTCTCCTATGC | |

| | | SEQ ID NO: 21 |
|---|---|---|
| HTTCR#C-19 | CGGCCGCCACCATGGGTACCAGTCTCCTATGCTGG | |

| | | SEQ ID NO: 22 |
|---|---|---|
| HTTCR#C-20 | CGGCCGCCACCATGGGCACCAGCCTCCT | |

| | | SEQ ID NO: 23 |
|---|---|---|
| HTTCR#C-21 | CGGCCGCCACCATGGGGACCAGCCTCCT | |

| | | SEQ ID NO: 24 |
|---|---|---|
| HTTCR#C-22 | CGGCCGCCACCATGGCCCTGTGTCTCCTGG | |

| | | SEQ ID NO: 25 |
|---|---|---|
| HTTCR#C-23 | CGGCCGCCACCATGGGCACGAGGCTCTTCT | |

| | | SEQ ID NO: 26 |
|---|---|---|
| HTTCR#C-24 | CGGCCGCCACCATGGGCACCAGGCTCTTCT | |

| | | SEQ ID NO: 27 |
|---|---|---|
| HTTCR#C-25 | CGGCCGCCACCATGTGGCCCTTTGTCTGCTGT | |

| | | SEQ ID NO: 28 |
|---|---|---|
| HTTCR#C-26 | CGGCCGCCACCATGGGCACAAGGTTGTTCTTCTATGT | |

| | | SEQ ID NO: 29 |
|---|---|---|
| HTTCR#C-27 | CGGCCGCCACCATGAGCACCAGGCTTCTCTGC | |

| | | SEQ ID NO: 30 |
|---|---|---|
| HTTCR#C-28 | CGGCCGCCACCATGGGTACCAGGCTCCTCTG | |

| | | SEQ ID NO: 31 |
|---|---|---|
| HTTCR#C-29 | CGGCCGCCACCATGGACTCCTGGACCTTCTGC | |

| | | SEQ ID NO: 32 |
|---|---|---|
| HTTCR#C-30 | CGGCCGCCACCATGGACTCCTGGACCCTCTG | |

| | | SEQ ID NO: 33 |
|---|---|---|
| HTTCR#C-31 | CGGCCGCCACCATGGGCTCCTGGACCCTC | |

| | | SEQ ID NO: 34 |
|---|---|---|
| HTTCR#C-32 | CGGCCGCCACCATGGCCACCAGGCTCCT | |

| | | SEQ ID NO: 35 |
|---|---|---|
| HTTCR#C-33 | CGGCCGCCACCATGCTTAGTCCTGACCTGCCTG | |

| | | SEQ ID NO: 36 |
|---|---|---|
| HTTCR#C-34 | CGGCCGCCACCATGGTTTCCAGGCTTCTCAGTTTAGTG | |

| | | SEQ ID NO: 37 |
|---|---|---|
| HTTCR#C-35 | CGGCCGCCACCATGGGTCCTGGGCTTCTCC | |

| | | SEQ ID NO: 38 |
|---|---|---|
| HTTCR#C-36 | CGGCCGCCACCATGAGCCCAATATTCACCTGCATCA | |

| | | SEQ ID NO: 39 |
|---|---|---|
| HTTCR#C-37 | CGGCCGCCACCATGGACACCAGAGTACTCTGCTG | |

| | | SEQ ID NO: 40 |
|---|---|---|
| HTTCR#C-38 | CGGCCGCCACCATGAGCAACCAGGTGCTCTG | |

| | | SEQ ID NO: 41 |
|---|---|---|
| HTTCR#C-39 | CGGCCGCCACCATGCTGCTGCTTCTGCTGC | |

| | | SEQ ID NO: 42 |
|---|---|---|
| HTTCR#C-40 | CGGCCGCCACCATGGCCTCCCTGCTCTTCT | |

| | | SEQ ID NO: 43 |
|---|---|---|
| HTTCR#C-41 | CGGCCGCCACCATGACTATCAGGCTCCTCTGCTACA | |

| | | SEQ ID NO: 44 |
|---|---|---|
| HTTCR#C-42 | CGGCCGCCACCATGGGCCCCAGCTC | |

| | | SEQ ID NO: 45 |
|---|---|---|
| HTTCR#C-43 | CGGCCGCCACCATGGGAATCAGGCTCCTCTGTC | |

| | | SEQ ID NO: 46 |
|---|---|---|
| HTTCR#C-44 | CGGCCGCCACCATGCTGAGTCTTCTGCTCCTTCTC | |

| | | SEQ ID NO: 47 |
|---|---|---|
| HTTCR#C-45 | CGGCCGCCACCATGATGCTCTGCTCTCTCCTTGC | | and HTTCR#B (CT-CAAACACAGCGACCTCGGGTGGGAACAC; SEQ ID NO:2), and:

| | | SEQ ID NO: 50 |
|---|---|---|
| HTTCR#F-1 | AACCCCGGTCCCATGTGGGGAGCTTTCCTTCTCTATG | |

| | | SEQ ID NO: 51 |
|---|---|---|
| HTTCR#F-2 | AACCCCGGTCCCATGTGGGGAGTTTTCCTTCTTTATGTTTCC | |

| | | SEQ ID NO: 52 |
|---|---|---|
| HTTCR#F-3 | AACCCCGGTCCCATGGCTTTGCAGAGCACTCTG | |

| | | SEQ ID NO: 53 |
|---|---|---|
| HTTCR#F-4 | AACCCCGGTCCCATGGCCTCTGCACCCATCT | |

| | | SEQ ID NO: 54 |
|---|---|---|
| HTTCR#F-5 | AACCCCGGTCCCATGAGGCAAGTGGCGAGAGT | |

| | | SEQ ID NO: 55 |
|---|---|---|
| HTTCR#F-6 | AACCCCGGTCCCATGAAGACATTTGCTGGATTTTCGTTCCT | |

| | | SEQ ID NO: 56 |
|---|---|---|
| HTTCR#F-7 | AACCCCGGTCCCATGGAGTCATTCCTGGGAGGTG | |

| | | SEQ ID NO: 57 |
|---|---|---|
| HTTCR#F-8 | AACCCCGGTCCCATGGAGTCATCCCTGGGAGG | |

| | | SEQ ID NO: 58 |
|---|---|---|
| HTTCR#F-9 | AACCCCGGTCCCATGGAGAAGATGCGGAGACCTG | |

| | | SEQ ID NO: 59 |
|---|---|---|
| HTTCR#F-10 | AACCCCGGTCCCATGCTCCTGTTGCTCATACCAGT | |

| | | SEQ ID NO: 60 |
|---|---|---|
| HTTCR#F-11 | AACCCCGGTCCCATGCTCCTGCTGCTCGTCC | |

| | | SEQ ID NO: 61 |
|---|---|---|
| HTTCR#F-12 | AACCCCGGTCCCATGCTCCTGGAGCTTATCCCAC | |

| | | SEQ ID NO: 62 |
|---|---|---|
| HTTCR#F-13 | AACCCCGGTCCCATGAATTCTTCTCTAGGACCAGCGATT | |

| | | SEQ ID NO: 63 |
|---|---|---|
| HTTCR#F-14 | AACCCCGGTCCCATGAACTATTCTCCAGGCTTAGTATCTCTGATACT | |

| | | SEQ ID NO: 64 |
|---|---|---|
| HTTCR#F-15 | AACCCCGGTCCCATGAAAAGCATCTGACGACCTTCTTGG | |

| | | SEQ ID NO: 65 |
|---|---|---|
| HTTCR#F-16 | AACCCCGGTCCCATGATGATATCCTTGAGAGTTTTACTGGTGATCC | |

| | | SEQ ID NO: 66 |
|---|---|---|
| HTTCR#F-17 | AACCCCGGTCCCATGATGAAATCCTTGAGAGTTTTACTAGTGATCCT | |

| | | SEQ ID NO: 67 |
|---|---|---|
| HTTCR#F-18 | AACCCCGGTCCCATGATGAAATCCTTGAGAGTTTTACTGGTGATCC | |

| | |
|---|---|
| HTTCR#F-19 | AACCCCGGTCCCATGATGAAATCCTTGAGAGTTTTACTGGTCATCC (SEQ ID NO: 68) |
| HTTCR#F-20 | AACCCCGGTCCCATGACATCCATTCGAGCTGTATTTATATTCCTGT (SEQ ID NO: 69) |
| HTTCR#F-21 | AACCCCGGTCCCATGATGGCAGGCATTCGAGTTTTATTTATGTAC (SEQ ID NO: 70) |
| HTTCR#F-22 | AACCCCGGTCCCATGTCACTTTCTAGCCTGCTGAAGG (SEQ ID NO: 71) |
| HTTCR#F-23 | AACCCCGGTCCCATGAAGCCCACCCTCATCTCAG (SEQ ID NO: 72) |
| HTTCR#F-24 | AACCCCGGTCCCATGGAAACTCTCCTGGGAGTGTC (SEQ ID NO: 73) |
| HTTCR#F-25 | AACCCCGGTCCCATGCTGTCTGCTTCCTGCTCA (SEQ ID NO: 74) |
| HTTCR#F-26 | AACCCCGGTCCCATGAACATGCTGACTGCCAGC (SEQ ID NO: 75) |
| HTTCR#F-27 | AACCCCGGTCCCATGGAGAAAATGTTGGAGTGTGCATTCA (SEQ ID NO: 76) |
| HTTCR#F-28 | AACCCCGGTCCCATGGAGACCCTCTTGGGCC (SEQ ID NO: 77) |
| HTTCR#F-29 | AACCCCGGTCCCATGAAGAGGATATTGGGAGCTCTGC (SEQ ID NO: 78) |
| HTTCR#F-30 | AACCCCGGTCCCATGGACAAGATCTTAGGAGCATCATTTTTAGTTCT (SEQ ID NO: 79) |
| HTTCR#F-31 | AACCCCGGTCCCATGGAGAAGAATCCTTTGGCAGCC (SEQ ID NO: 80) |
| HTTCR#F-32 | AACCCCGGTCCCATGCTACTCATCACATCAATGTTGGTCTTATG (SEQ ID NO: 81) |
| HTTCR#F-33 | AACCCCGGTCCCATGAGGCTGGTGGCAAGAGTAA (SEQ ID NO: 82) |
| HTTCR#F-34 | AACCCCGGTCCCATGAGGTTGGTGACAAGCATTACTGTAC (SEQ ID NO: 83) |
| HTTCR#F-35 | AACCCCGGTCCCATGAAGTTGGTGACAAGCATTACTGTACTC (SEQ ID NO: 84) |
| HTTCR#F-36 | AACCCCGGTCCCATGGTCCTGAAATTCTCCGTGTCC (SEQ ID NO: 85) |
| HTTCR#F-37 | AACCCCGGTCCCATGGCCATGCTCCTGGG (SEQ ID NO: 86) |
| HTTCR#F-38 | AACCCCGGTCCCATGGAGACTCTCCTGAAAGTGCTTTC (SEQ ID NO: 87) |
| HTTCR#F-39 | AACCCCGGTCCCATGGAGACTCTCCTGAAAGTGCC (SEQ ID NO: 88) |
| HTTCR#F-40 | AACCCCGGTCCCATGGAGACTGTTCTGCAAGTACTCC (SEQ ID NO: 89) |
| HTTCR#F-41 | AACCCCGGTCCCATGCTCCTTGAACATTTATTAATAATCTTGTGGATGC (SEQ ID NO: 90) |
| HTTCR#F-42 | AACCCCGGTCCCATGATGAAGTGTCCGCAGGCT (SEQ ID NO: 91) |
| HTTCR#F-43 | AACCCCGGTCCCATGATGAAGTGTCCACAGGCTTTACT (SEQ ID NO: 92) |
| HTTCR#F-44 | AACCCCGGTCCCATGACACGAGTTAGCTTGCTGTG (SEQ ID NO: 93) |
| HTTCR#F-45 | AACCCCGGTCCCATGACACCAGTTAGCTTGCTGTG (SEQ ID NO: 94) |
| HTTCR#F-46 | AACCCCGGTCCCATGGCATGCCCTGGCTT (SEQ ID NO: 95) |
| HTTCR#F-47 | AACCCCGGTCCCATGAAGAAGCTACTAGCAATGATTCTGTGG (SEQ ID NO: 96) |
| HTTCR#F-48 | AACCCCGGTCCCATGAACTCCTCTCTGGACTTTCTAATTCTGA (SEQ ID NO: 97) |
| HTTCR#F-49 | AACCCCGGTCCCATGGTGAAGATCCGGCAATTTTTGTTG (SEQ ID NO: 98) | and HTTCR#D GGAGACGTG-GAAGAAAACCCCGGTCCCATG (SEQ ID NO:48) and HT-TCR#E-AGGCAGACAGACTTGTCACTG-GATTTAGAG (SEQ ID NO:49).

16. The kit of claim 15, further comprising a destination vector comprising a NotI and/or a PspOMI restriction endonuclease recognition sequence, and a segment encoding a cysteine-modified Cα fragment.

17. The kit of claim 16, further comprising a NotI and/or a PspOMI restriction endonuclease.

18. The kit of claim 15, further comprising one or more buffers for performing a first strand cDNA synthesis, and/or a polymerase chain reaction (PCR) for performing a second strand cDNA synthesis.

19. The kit of claim 15, further comprising a reverse transcriptase and/or a DNA polymerase.

20. The kit of claim 15, further comprising a destination vector comprising a NotI and/or a PspOMI restriction endonuclease recognition sequence, and a segment encoding a cysteine-modified Cα fragment, and one or more buffers for performing a first strand cDNA synthesis and a second strand cDNA synthesis, a reverse transcriptase and a DNA polymerase, and a NotI and/or a PspOMI restriction endonuclease.

* * * * *

```
                        SEQUENCE LISTING

<160> NUMBER OF SEQ ID NOS: 131

<210> SEQ ID NO 1
<211> LENGTH: 43
<212> TYPE: DNA
<213> ORGANISM: artificial sequence
<220> FEATURE:
<223> OTHER INFORMATION: primer

<400> SEQUENCE: 1
acttaagctt ggtaccgagc tcggatctgc ggccgccacc atg              43

<210> SEQ ID NO 2
<211> LENGTH: 30
<212> TYPE: DNA
<213> ORGANISM: artificial sequence
<220> FEATURE:
<223> OTHER INFORMATION: Primer

<400> SEQUENCE: 2
ctcaaacaca gcgacctcgg gtgggaacac                             30

<210> SEQ ID NO 3
<211> LENGTH: 34
<212> TYPE: DNA
<213> ORGANISM: artificial sequence
<220> FEATURE:
<223> OTHER INFORMATION: Primer

<400> SEQUENCE: 3
cggccgccac catggatacc tggctcgtat gctg                        34

<210> SEQ ID NO 4
<211> LENGTH: 34
<212> TYPE: DNA
<213> ORGANISM: artificial sequence
<220> FEATURE:
<223> OTHER INFORMATION: Primer

<400> SEQUENCE: 4
cggccgccac catggatacc tggctgtatg ctgg                        34

<210> SEQ ID NO 5
<211> LENGTH: 28
<212> TYPE: DNA
<213> ORGANISM: artificial sequence
<220> FEATURE:
<223> OTHER INFORMATION: primer
```

-continued

```
<400> SEQUENCE: 5
cggccgccac catgggctgc aggctcct                                  28

<210> SEQ ID NO 6
<211> LENGTH: 30
<212> TYPE: DNA
<213> ORGANISM: artificial sequence
<220> FEATURE:
<223> OTHER INFORMATION: primer

<400> SEQUENCE: 6
cggccgccac catgggcttc aggctcctct                                30

<210> SEQ ID NO 7
<211> LENGTH: 27
<212> TYPE: DNA
<213> ORGANISM: artificial sequence
<220> FEATURE:
<223> OTHER INFORMATION: Primer

<400> SEQUENCE: 7
cggccgccac catgggctgc aggctgc                                   27

<210> SEQ ID NO 8
<211> LENGTH: 28
<212> TYPE: DNA
<213> ORGANISM: artificial sequence
<220> FEATURE:
<223> OTHER INFORMATION: Primer

<400> SEQUENCE: 8
cggccgccac catgggctcc aggctgct                                  28

<210> SEQ ID NO 9
<211> LENGTH: 26
<212> TYPE: DNA
<213> ORGANISM: artificial sequence
<220> FEATURE:
<223> OTHER INFORMATION: Primer

<400> SEQUENCE: 9
cggccgccac catgggccct gggctc                                    26

<210> SEQ ID NO 10
<211> LENGTH: 24
<212> TYPE: DNA
<213> ORGANISM: artificial sequence
<220> FEATURE:
<223> OTHER INFORMATION: Primer

<400> SEQUENCE: 10
cggccgccac catgggcccc gggc                                      24

<210> SEQ ID NO 11
<211> LENGTH: 28
<212> TYPE: DNA
<213> ORGANISM: artificial sequence
<220> FEATURE:
<223> OTHER INFORMATION: Primer

<400> SEQUENCE: 11
cggccgccac catgggaccc aggctcct                                  28

<210> SEQ ID NO 12
<211> LENGTH: 30
```

-continued

```
<212> TYPE: DNA
<213> ORGANISM: artificial sequence
<220> FEATURE:
<223> OTHER INFORMATION: Primer

<400> SEQUENCE: 12
cggccgccac catgagcatc gggctcctgt                                30

<210> SEQ ID NO 13
<211> LENGTH: 28
<212> TYPE: DNA
<213> ORGANISM: artificial sequence
<220> FEATURE:
<223> OTHER INFORMATION: Primer

<400> SEQUENCE: 13
cggccgccac catgagcctc gggctcct                                  28

<210> SEQ ID NO 14
<211> LENGTH: 34
<212> TYPE: DNA
<213> ORGANISM: artificial sequence
<220> FEATURE:
<223> OTHER INFORMATION: Primer

<400> SEQUENCE: 14
cggccgccac catgagaatc aggctcctgt gctg                           34

<210> SEQ ID NO 15
<211> LENGTH: 32
<212> TYPE: DNA
<213> ORGANISM: artificial sequence
<220> FEATURE:
<223> OTHER INFORMATION: Primer

<400> SEQUENCE: 15
cggccgccac catgagcatc aggctcctgt gc                             32

<210> SEQ ID NO 16
<211> LENGTH: 30
<212> TYPE: DNA
<213> ORGANISM: artificial sequence
<220> FEATURE:
<223> OTHER INFORMATION: Primer

<400> SEQUENCE: 16
cggccgccac catgagcatc ggcctcctgt                                30

<210> SEQ ID NO 17
<211> LENGTH: 32
<212> TYPE: DNA
<213> ORGANISM: artificial sequence
<220> FEATURE:
<223> OTHER INFORMATION: Primer

<400> SEQUENCE: 17
cggccgccac catgagcatc agcctcctgt gc                             32

<210> SEQ ID NO 18
<211> LENGTH: 28
<212> TYPE: DNA
<213> ORGANISM: artificial sequence
<220> FEATURE:
<223> OTHER INFORMATION: Primer

<400> SEQUENCE: 18
```
cggccgccac catgggcacc aggctcct                    28

<210> SEQ ID NO 19
<211> LENGTH: 32
<212> TYPE: DNA
<213> ORGANISM: artificial sequence
<220> FEATURE:
<223> OTHER INFORMATION: Primer

<400> SEQUENCE: 19
cggccgccac catgggcacc agtgtcctat gt                    32

<210> SEQ ID NO 20
<211> LENGTH: 32
<212> TYPE: DNA
<213> ORGANISM: artificial sequence
<220> FEATURE:
<223> OTHER INFORMATION: Primer

<400> SEQUENCE: 20
cggccgccac catgggcacc agtctcctat gc                    32

<210> SEQ ID NO 21
<211> LENGTH: 35
<212> TYPE: DNA
<213> ORGANISM: artificial sequence
<220> FEATURE:
<223> OTHER INFORMATION: Primer

<400> SEQUENCE: 21
cggccgccac catgggtacc agtctcctat gctgg                    35

<210> SEQ ID NO 22
<211> LENGTH: 28
<212> TYPE: DNA
<213> ORGANISM: artificial sequence
<220> FEATURE:
<223> OTHER INFORMATION: Primer

<400> SEQUENCE: 22
cggccgccac catgggcacc agcctcct                    28

<210> SEQ ID NO 23
<211> LENGTH: 28
<212> TYPE: DNA
<213> ORGANISM: artificial sequence
<220> FEATURE:
<223> OTHER INFORMATION: Primer

<400> SEQUENCE: 23
cggccgccac catggggacc agcctcct                    28

<210> SEQ ID NO 24
<211> LENGTH: 30
<212> TYPE: DNA
<213> ORGANISM: artificial sequence
<220> FEATURE:
<223> OTHER INFORMATION: Primer

<400> SEQUENCE: 24
cggccgccac catggccctg tgtctcctgg                    30

<210> SEQ ID NO 25
<211> LENGTH: 30
<212> TYPE: DNA
<213> ORGANISM: artificial sequence

```
<220> FEATURE:
<223> OTHER INFORMATION: Primer

<400> SEQUENCE: 25
cggccgccac catgggcacg aggctcttct                                    30

<210> SEQ ID NO 26
<211> LENGTH: 30
<212> TYPE: DNA
<213> ORGANISM: artificial sequence
<220> FEATURE:
<223> OTHER INFORMATION: Primer

<400> SEQUENCE: 26
cggccgccac catgggcacc aggctcttct                                    30

<210> SEQ ID NO 27
<211> LENGTH: 32
<212> TYPE: DNA
<213> ORGANISM: artificial sequence
<220> FEATURE:
<223> OTHER INFORMATION: Primer

<400> SEQUENCE: 27
cggccgccac catgtggccc tttgtctgct gt                                 32

<210> SEQ ID NO 28
<211> LENGTH: 37
<212> TYPE: DNA
<213> ORGANISM: artificial sequence
<220> FEATURE:
<223> OTHER INFORMATION: Primer

<400> SEQUENCE: 28
cggccgccac catgggcaca aggttgttct tctatgt                            37

<210> SEQ ID NO 29
<211> LENGTH: 32
<212> TYPE: DNA
<213> ORGANISM: artificial sequence
<220> FEATURE:
<223> OTHER INFORMATION: Primer

<400> SEQUENCE: 29
cggccgccac catgagcacc aggcttctct gc                                 32

<210> SEQ ID NO 30
<211> LENGTH: 31
<212> TYPE: DNA
<213> ORGANISM: artificial sequence
<220> FEATURE:
<223> OTHER INFORMATION: Primer

<400> SEQUENCE: 30
cggccgccac catgggtacc aggctcctct g                                  31

<210> SEQ ID NO 31
<211> LENGTH: 32
<212> TYPE: DNA
<213> ORGANISM: artificial sequence
<220> FEATURE:
<223> OTHER INFORMATION: Primer

<400> SEQUENCE: 31
cggccgccac catggactcc tggaccttct gc                                 32
```

```
<210> SEQ ID NO 32
<211> LENGTH: 31
<212> TYPE: DNA
<213> ORGANISM: artificial sequence
<220> FEATURE:
<223> OTHER INFORMATION: Primer

<400> SEQUENCE: 32
cggccgccac catggactcc tggaccctct g                                    31

<210> SEQ ID NO 33
<211> LENGTH: 29
<212> TYPE: DNA
<213> ORGANISM: artificial sequence
<220> FEATURE:
<223> OTHER INFORMATION: Primer

<400> SEQUENCE: 33
cggccgccac catgggctcc tggaccctc                                       29

<210> SEQ ID NO 34
<211> LENGTH: 28
<212> TYPE: DNA
<213> ORGANISM: artificial sequence
<220> FEATURE:
<223> OTHER INFORMATION: Primer

<400> SEQUENCE: 34
cggccgccac catggccacc aggctcct                                        28

<210> SEQ ID NO 35
<211> LENGTH: 33
<212> TYPE: DNA
<213> ORGANISM: artificial sequence
<220> FEATURE:
<223> OTHER INFORMATION: Primer

<400> SEQUENCE: 35
cggccgccac catgcttagt cctgacctgc ctg                                  33

<210> SEQ ID NO 36
<211> LENGTH: 38
<212> TYPE: DNA
<213> ORGANISM: artificial sequence
<220> FEATURE:
<223> OTHER INFORMATION: Primer

<400> SEQUENCE: 36
cggccgccac catggtttcc aggcttctca gtttagtg                             38

<210> SEQ ID NO 37
<211> LENGTH: 30
<212> TYPE: DNA
<213> ORGANISM: artificial sequence
<220> FEATURE:
<223> OTHER INFORMATION: Primer

<400> SEQUENCE: 37
cggccgccac catgggtcct gggcttctcc                                      30

<210> SEQ ID NO 38
<211> LENGTH: 36
<212> TYPE: DNA
<213> ORGANISM: artificial sequence
<220> FEATURE:
<223> OTHER INFORMATION: Primer
```

```
<400> SEQUENCE: 38
cggccgccac catgagccca atattcacct gcatca                              36

<210> SEQ ID NO 39
<211> LENGTH: 34
<212> TYPE: DNA
<213> ORGANISM: artificial sequence
<220> FEATURE:
<223> OTHER INFORMATION: Primer

<400> SEQUENCE: 39
cggccgccac catggacacc agagtactct gctg                                34

<210> SEQ ID NO 40
<211> LENGTH: 31
<212> TYPE: DNA
<213> ORGANISM: artificial sequence
<220> FEATURE:
<223> OTHER INFORMATION: Primer

<400> SEQUENCE: 40
cggccgccac catgagcaac caggtgctct g                                   31

<210> SEQ ID NO 41
<211> LENGTH: 30
<212> TYPE: DNA
<213> ORGANISM: artificial sequence
<220> FEATURE:
<223> OTHER INFORMATION: Primer

<400> SEQUENCE: 41
cggccgccac catgctgctg cttctgctgc                                     30

<210> SEQ ID NO 42
<211> LENGTH: 30
<212> TYPE: DNA
<213> ORGANISM: artificial sequence
<220> FEATURE:
<223> OTHER INFORMATION: Primer

<400> SEQUENCE: 42
cggccgccac catggcctcc ctgctcttct                                     30

<210> SEQ ID NO 43
<211> LENGTH: 36
<212> TYPE: DNA
<213> ORGANISM: artificial sequence
<220> FEATURE:
<223> OTHER INFORMATION: Primer

<400> SEQUENCE: 43
cggccgccac catgactatc aggctcctct gctaca                              36

<210> SEQ ID NO 44
<211> LENGTH: 26
<212> TYPE: DNA
<213> ORGANISM: artificial sequence
<220> FEATURE:
<223> OTHER INFORMATION: Primer

<400> SEQUENCE: 44
cggccgccac catgggcccc cagctc                                         26

<210> SEQ ID NO 45
```

-continued

```
<211> LENGTH: 33
<212> TYPE: DNA
<213> ORGANISM: artificial sequence
<220> FEATURE:
<223> OTHER INFORMATION: Primer

<400> SEQUENCE: 45
cggccgccac catgggaatc aggctcctct gtc                          33

<210> SEQ ID NO 46
<211> LENGTH: 35
<212> TYPE: DNA
<213> ORGANISM: artificial sequence
<220> FEATURE:
<223> OTHER INFORMATION: Primer

<400> SEQUENCE: 46
cggccgccac catgctgagt cttctgctcc ttctc                        35

<210> SEQ ID NO 47
<211> LENGTH: 34
<212> TYPE: DNA
<213> ORGANISM: artificial sequence
<220> FEATURE:
<223> OTHER INFORMATION: Primer

<400> SEQUENCE: 47
cggccgccac catgatgctc tgctctctcc ttgc                         34

<210> SEQ ID NO 48
<211> LENGTH: 30
<212> TYPE: DNA
<213> ORGANISM: artificial sequence
<220> FEATURE:
<223> OTHER INFORMATION: Primer

<400> SEQUENCE: 48
ggagacgtgg aagaaaaccc cggtcccatg                              30

<210> SEQ ID NO 49
<211> LENGTH: 30
<212> TYPE: DNA
<213> ORGANISM: artificial sequence
<220> FEATURE:
<223> OTHER INFORMATION: Primer

<400> SEQUENCE: 49
aggcagacag acttgtcact ggatttagag                              30

<210> SEQ ID NO 50
<211> LENGTH: 37
<212> TYPE: DNA
<213> ORGANISM: artificial sequence
<220> FEATURE:
<223> OTHER INFORMATION: Primer

<400> SEQUENCE: 50
aaccccggtc ccatgtgggg agctttcctt ctctatg                      37

<210> SEQ ID NO 51
<211> LENGTH: 42
<212> TYPE: DNA
<213> ORGANISM: artificial sequence
<220> FEATURE:
<223> OTHER INFORMATION: Primer

<400> SEQUENCE: 51
``` aacccggtc ccatgtgggg agttttcctt ctttatgttt cc        42

<210> SEQ ID NO 52
<211> LENGTH: 33
<212> TYPE: DNA
<213> ORGANISM: artificial sequence
<220> FEATURE:
<223> OTHER INFORMATION: Primer

<400> SEQUENCE: 52
aaccccggtc ccatggcttt gcagagcact ctg        33

<210> SEQ ID NO 53
<211> LENGTH: 31
<212> TYPE: DNA
<213> ORGANISM: artificial sequence
<220> FEATURE:
<223> OTHER INFORMATION: Primer

<400> SEQUENCE: 53
aaccccggtc ccatggcctc tgcacccatc t        31

<210> SEQ ID NO 54
<211> LENGTH: 32
<212> TYPE: DNA
<213> ORGANISM: artificial sequence
<220> FEATURE:
<223> OTHER INFORMATION: Primer

<400> SEQUENCE: 54
aaccccggtc ccatgaggca agtggcgaga gt        32

<210> SEQ ID NO 55
<211> LENGTH: 41
<212> TYPE: DNA
<213> ORGANISM: artificial sequence
<220> FEATURE:
<223> OTHER INFORMATION: Primer

<400> SEQUENCE: 55
aaccccggtc ccatgaagac atttgctgga ttttcgttcc t        41

<210> SEQ ID NO 56
<211> LENGTH: 34
<212> TYPE: DNA
<213> ORGANISM: artificial sequence
<220> FEATURE:
<223> OTHER INFORMATION: Primer

<400> SEQUENCE: 56
aaccccggtc ccatggagtc attcctggga ggtg        34

<210> SEQ ID NO 57
<211> LENGTH: 32
<212> TYPE: DNA
<213> ORGANISM: artificial sequence
<220> FEATURE:
<223> OTHER INFORMATION: Primer

<400> SEQUENCE: 57
aaccccggtc ccatggagtc atccctggga gg        32

<210> SEQ ID NO 58
<211> LENGTH: 34
<212> TYPE: DNA

```
<213> ORGANISM: artificial sequence
<220> FEATURE:
<223> OTHER INFORMATION: Primer

<400> SEQUENCE: 58
aaccccggtc ccatggagaa gatgcggaga cctg                                    34

<210> SEQ ID NO 59
<211> LENGTH: 35
<212> TYPE: DNA
<213> ORGANISM: artificial sequence
<220> FEATURE:
<223> OTHER INFORMATION: Primer

<400> SEQUENCE: 59
aaccccggtc ccatgctcct gttgctcata ccagt                                   35

<210> SEQ ID NO 60
<211> LENGTH: 31
<212> TYPE: DNA
<213> ORGANISM: artificial sequence
<220> FEATURE:
<223> OTHER INFORMATION: Primer

<400> SEQUENCE: 60
aaccccggtc ccatgctcct gctgctcgtc c                                       31

<210> SEQ ID NO 61
<211> LENGTH: 34
<212> TYPE: DNA
<213> ORGANISM: artificial sequence
<220> FEATURE:
<223> OTHER INFORMATION: Primer

<400> SEQUENCE: 61
aaccccggtc ccatgctcct ggagcttatc ccac                                    34

<210> SEQ ID NO 62
<211> LENGTH: 39
<212> TYPE: DNA
<213> ORGANISM: artificial sequence
<220> FEATURE:
<223> OTHER INFORMATION: Primer

<400> SEQUENCE: 62
aaccccggtc ccatgaattc ttctctagga ccagcgatt                               39

<210> SEQ ID NO 63
<211> LENGTH: 47
<212> TYPE: DNA
<213> ORGANISM: artificial sequence
<220> FEATURE:
<223> OTHER INFORMATION: Primer

<400> SEQUENCE: 63
aaccccggtc ccatgaacta ttctccaggc ttagtatctc tgatact                      47

<210> SEQ ID NO 64
<211> LENGTH: 40
<212> TYPE: DNA
<213> ORGANISM: artificial sequence
<220> FEATURE:
<223> OTHER INFORMATION: Primer

<400> SEQUENCE: 64
aaccccggtc ccatgaaaaa gcatctgacg accttcttgg                              40
```

<210> SEQ ID NO 65
<211> LENGTH: 46
<212> TYPE: DNA
<213> ORGANISM: artificial sequence
<220> FEATURE:
<223> OTHER INFORMATION: Primer

<400> SEQUENCE: 65
aaccccggtc ccatgatgat atccttgaga gttttactgg tgatcc        46

<210> SEQ ID NO 66
<211> LENGTH: 47
<212> TYPE: DNA
<213> ORGANISM: artificial sequence
<220> FEATURE:
<223> OTHER INFORMATION: Primer

<400> SEQUENCE: 66
aaccccggtc ccatgatgaa atccttgaga gttttactag tgatcct       47

<210> SEQ ID NO 67
<211> LENGTH: 46
<212> TYPE: DNA
<213> ORGANISM: artificial sequence
<220> FEATURE:
<223> OTHER INFORMATION: Primer

<400> SEQUENCE: 67
aaccccggtc ccatgatgaa atccttgaga gttttactgg tgatcc        46

<210> SEQ ID NO 68
<211> LENGTH: 46
<212> TYPE: DNA
<213> ORGANISM: artificial sequence
<220> FEATURE:
<223> OTHER INFORMATION: Primer

<400> SEQUENCE: 68
aaccccggtc ccatgatgaa atccttgaga gttttactgg tcatcc        46

<210> SEQ ID NO 69
<211> LENGTH: 46
<212> TYPE: DNA
<213> ORGANISM: artificial sequence
<220> FEATURE:
<223> OTHER INFORMATION: Primer

<400> SEQUENCE: 69
aaccccggtc ccatgacatc cattcgagct gtatttatat tcctgt        46

<210> SEQ ID NO 70
<211> LENGTH: 45
<212> TYPE: DNA
<213> ORGANISM: artificial sequence
<220> FEATURE:
<223> OTHER INFORMATION: Primer

<400> SEQUENCE: 70
aaccccggtc ccatgatggc aggcattcga gttttattta tgtac         45

<210> SEQ ID NO 71
<211> LENGTH: 37
<212> TYPE: DNA
<213> ORGANISM: artificial sequence
<220> FEATURE:

```
<223> OTHER INFORMATION: Primer

<400> SEQUENCE: 71
aaccccggtc ccatgtcact ttctagcctg ctgaagg                                   37

<210> SEQ ID NO 72
<211> LENGTH: 34
<212> TYPE: DNA
<213> ORGANISM: artificial sequence
<220> FEATURE:
<223> OTHER INFORMATION: Primer

<400> SEQUENCE: 72
aaccccggtc ccatgaagcc caccctcatc tcag                                      34

<210> SEQ ID NO 73
<211> LENGTH: 35
<212> TYPE: DNA
<213> ORGANISM: artificial sequence
<220> FEATURE:
<223> OTHER INFORMATION: Primer

<400> SEQUENCE: 73
aaccccggtc ccatggaaac tctcctggga gtgtc                                     35

<210> SEQ ID NO 74
<211> LENGTH: 33
<212> TYPE: DNA
<213> ORGANISM: artificial sequence
<220> FEATURE:
<223> OTHER INFORMATION: Primer

<400> SEQUENCE: 74
aaccccggtc ccatgctgtc tgcttcctgc tca                                       33

<210> SEQ ID NO 75
<211> LENGTH: 33
<212> TYPE: DNA
<213> ORGANISM: artificial sequence
<220> FEATURE:
<223> OTHER INFORMATION: Primer

<400> SEQUENCE: 75
aaccccggtc ccatgaacat gctgactgcc agc                                       33

<210> SEQ ID NO 76
<211> LENGTH: 40
<212> TYPE: DNA
<213> ORGANISM: artificial sequence
<220> FEATURE:
<223> OTHER INFORMATION: Primer

<400> SEQUENCE: 76
aaccccggtc ccatggagaa aatgttggag tgtgcattca                                40

<210> SEQ ID NO 77
<211> LENGTH: 31
<212> TYPE: DNA
<213> ORGANISM: artificial sequence
<220> FEATURE:
<223> OTHER INFORMATION: Primer

<400> SEQUENCE: 77
aaccccggtc ccatggagac cctcttgggc c                                         31
```

```
<210> SEQ ID NO 78
<211> LENGTH: 37
<212> TYPE: DNA
<213> ORGANISM: artificial sequence
<220> FEATURE:
<223> OTHER INFORMATION: Primer

<400> SEQUENCE: 78
aaccccggtc ccatgaagag gatattggga gctctgc                              37

<210> SEQ ID NO 79
<211> LENGTH: 47
<212> TYPE: DNA
<213> ORGANISM: artificial sequence
<220> FEATURE:
<223> OTHER INFORMATION: Primer

<400> SEQUENCE: 79
aaccccggtc ccatggacaa gatcttagga gcatcatttt tagttct                   47

<210> SEQ ID NO 80
<211> LENGTH: 36
<212> TYPE: DNA
<213> ORGANISM: artificial sequence
<220> FEATURE:
<223> OTHER INFORMATION: Primer

<400> SEQUENCE: 80
aaccccggtc ccatggagaa gaatcctttg gcagcc                               36

<210> SEQ ID NO 81
<211> LENGTH: 44
<212> TYPE: DNA
<213> ORGANISM: artificial sequence
<220> FEATURE:
<223> OTHER INFORMATION: Primer

<400> SEQUENCE: 81
aaccccggtc ccatgctact catcacatca atgttggtct tatg                      44

<210> SEQ ID NO 82
<211> LENGTH: 34
<212> TYPE: DNA
<213> ORGANISM: artificial sequence
<220> FEATURE:
<223> OTHER INFORMATION: Primer

<400> SEQUENCE: 82
aaccccggtc ccatgaggct ggtggcaaga gtaa                                 34

<210> SEQ ID NO 83
<211> LENGTH: 40
<212> TYPE: DNA
<213> ORGANISM: artificial sequence
<220> FEATURE:
<223> OTHER INFORMATION: Primer

<400> SEQUENCE: 83
aaccccggtc ccatgaggtt ggtgacaagc attactgtac                           40

<210> SEQ ID NO 84
<211> LENGTH: 42
<212> TYPE: DNA
<213> ORGANISM: artificial sequence
<220> FEATURE:
<223> OTHER INFORMATION: Primer
```

<400> SEQUENCE: 84
aaccccggtc ccatgaagtt ggtgacaagc attactgtac tc                          42

<210> SEQ ID NO 85
<211> LENGTH: 36
<212> TYPE: DNA
<213> ORGANISM: artificial sequence
<220> FEATURE:
<223> OTHER INFORMATION: Primer

<400> SEQUENCE: 85
aaccccggtc ccatggtcct gaaattctcc gtgtcc                                 36

<210> SEQ ID NO 86
<211> LENGTH: 29
<212> TYPE: DNA
<213> ORGANISM: artificial sequence
<220> FEATURE:
<223> OTHER INFORMATION: Primer

<400> SEQUENCE: 86
aaccccggtc ccatggccat gctcctggg                                         29

<210> SEQ ID NO 87
<211> LENGTH: 38
<212> TYPE: DNA
<213> ORGANISM: artificial sequence
<220> FEATURE:
<223> OTHER INFORMATION: Primer

<400> SEQUENCE: 87
aaccccggtc ccatggagac tctcctgaaa gtgctttc                               38

<210> SEQ ID NO 88
<211> LENGTH: 35
<212> TYPE: DNA
<213> ORGANISM: artificial sequence
<220> FEATURE:
<223> OTHER INFORMATION: Primer

<400> SEQUENCE: 88
aaccccggtc ccatggagac tctcctgaaa gtgcc                                  35

<210> SEQ ID NO 89
<211> LENGTH: 37
<212> TYPE: DNA
<213> ORGANISM: artificial sequence
<220> FEATURE:
<223> OTHER INFORMATION: Primer

<400> SEQUENCE: 89
aaccccggtc ccatggagac tgttctgcaa gtactcc                                37

<210> SEQ ID NO 90
<211> LENGTH: 49
<212> TYPE: DNA
<213> ORGANISM: artificial sequence
<220> FEATURE:
<223> OTHER INFORMATION: Primer

<400> SEQUENCE: 90
aaccccggtc ccatgctcct tgaacattta ttaataatct tgtggatgc                   49

<210> SEQ ID NO 91
<211> LENGTH: 33

```
<212> TYPE: DNA
<213> ORGANISM: artificial sequence
<220> FEATURE:
<223> OTHER INFORMATION: Primer

<400> SEQUENCE: 91 aacccoggtc ccatgatgaa gtgtccgcag gct                              33

<210> SEQ ID NO 92
<211> LENGTH: 38
<212> TYPE: DNA
<213> ORGANISM: artificial sequence
<220> FEATURE:
<223> OTHER INFORMATION: Primer

<400> SEQUENCE: 92 aacccoggtc ccatgatgaa gtgtccacag gctttact                         38

<210> SEQ ID NO 93
<211> LENGTH: 35
<212> TYPE: DNA
<213> ORGANISM: artificial sequence
<220> FEATURE:
<223> OTHER INFORMATION: Primer

<400> SEQUENCE: 93 aacccoggtc ccatgacacg agttagcttg ctgtg                            35

<210> SEQ ID NO 94
<211> LENGTH: 35
<212> TYPE: DNA
<213> ORGANISM: artificial sequence
<220> FEATURE:
<223> OTHER INFORMATION: Primer

<400> SEQUENCE: 94 aacccoggtc ccatgacacc agttagcttg ctgtg                            35

<210> SEQ ID NO 95
<211> LENGTH: 29
<212> TYPE: DNA
<213> ORGANISM: artificial sequence
<220> FEATURE:
<223> OTHER INFORMATION: Primer

<400> SEQUENCE: 95 aacccoggtc ccatggcatg ccctggctt                                   29

<210> SEQ ID NO 96
<211> LENGTH: 42
<212> TYPE: DNA
<213> ORGANISM: artificial sequence
<220> FEATURE:
<223> OTHER INFORMATION: Primer

<400> SEQUENCE: 96 aacccoggtc ccatgaagaa gctactagca atgattctgt gg                    42

<210> SEQ ID NO 97
<211> LENGTH: 43
<212> TYPE: DNA
<213> ORGANISM: artificial sequence
<220> FEATURE:
<223> OTHER INFORMATION: Primer

<400> SEQUENCE: 97
```

-continued aaccccggtc ccatgaactc ctctctggac tttctaattc tga    43

<210> SEQ ID NO 98
<211> LENGTH: 39
<212> TYPE: DNA
<213> ORGANISM: artificial sequence
<220> FEATURE:
<223> OTHER INFORMATION: Primer

<400> SEQUENCE: 98
aaccccggtc ccatggtgaa gatccggcaa tttttgttg    39

<210> SEQ ID NO 99
<211> LENGTH: 42
<212> TYPE: DNA
<213> ORGANISM: artificial sequence
<220> FEATURE:
<223> OTHER INFORMATION: Constant region

<400> SEQUENCE: 99
accagctggg gccctctaaa tccagtgaca agtctgtctg cc    42

<210> SEQ ID NO 100
<211> LENGTH: 24
<212> TYPE: DNA
<213> ORGANISM: artificial sequence
<220> FEATURE:
<223> OTHER INFORMATION: Primer

<400> SEQUENCE: 100
aattgatccg cggccgccac catg    24

<210> SEQ ID NO 101
<211> LENGTH: 27
<212> TYPE: DNA
<213> ORGANISM: artificial sequence
<220> FEATURE:
<223> OTHER INFORMATION: Primer

<400> SEQUENCE: 101
gagggcccca gctggtacac ggcaggg    27

<210> SEQ ID NO 102
<211> LENGTH: 43
<212> TYPE: DNA
<213> ORGANISM: artificial sequence
<220> FEATURE:
<223> OTHER INFORMATION: Primer

<400> SEQUENCE: 102
ttcaccgatc gcgattctca aacaaatgtg tcacaaagta agg    43

<210> SEQ ID NO 103
<211> LENGTH: 34
<212> TYPE: DNA
<213> ORGANISM: artificial sequence
<220> FEATURE:
<223> OTHER INFORMATION: Primer

<400> SEQUENCE: 103
gagaatcgcg atcggtgaat aggcagacag actt    34

<210> SEQ ID NO 104
<211> LENGTH: 35
<212> TYPE: DNA
<213> ORGANISM: artificial sequence

```
<220> FEATURE:
<223> OTHER INFORMATION: Primer
<220> FEATURE:
<221> NAME/KEY: misc_feature
<222> LOCATION: (1)..(3)
<223> OTHER INFORMATION: n is a, c, g, or t

<400> SEQUENCE: 104
nnnatttaaa tcggtgaata ggcagacaga cttgt                              35

<210> SEQ ID NO 105
<211> LENGTH: 21
<212> TYPE: DNA
<213> ORGANISM: artificial sequence
<220> FEATURE:
<223> OTHER INFORMATION: Excluded sequence

<400> SEQUENCE: 105
aaggatccga attcctgcag g                                             21

<210> SEQ ID NO 106
<211> LENGTH: 20
<212> TYPE: DNA
<213> ORGANISM: artificial sequence
<220> FEATURE:
<223> OTHER INFORMATION: Primer

<400> SEQUENCE: 106
tggaggagaa ccctggacct                                               20

<210> SEQ ID NO 107
<211> LENGTH: 11
<212> TYPE: DNA
<213> ORGANISM: artificial sequence
<220> FEATURE:
<223> OTHER INFORMATION: Primer

<400> SEQUENCE: 107
cggccgccac c                                                        11

<210> SEQ ID NO 108
<211> LENGTH: 12
<212> TYPE: DNA
<213> ORGANISM: artificial sequence
<220> FEATURE:
<223> OTHER INFORMATION: Primer

<400> SEQUENCE: 108
aaccccggtc cc                                                       12

<210> SEQ ID NO 109
<211> LENGTH: 14
<212> TYPE: DNA
<213> ORGANISM: artificial sequence
<220> FEATURE:
<223> OTHER INFORMATION: Primer

<400> SEQUENCE: 109
cggccgccac catg                                                     14

<210> SEQ ID NO 110
<211> LENGTH: 12
<212> TYPE: DNA
<213> ORGANISM: artificial sequence
<220> FEATURE:
<223> OTHER INFORMATION: Primer
```

<400> SEQUENCE: 110
aaccccggtc cc                                                            12

<210> SEQ ID NO 111
<211> LENGTH: 17
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (1)..(2)
<223> OTHER INFORMATION: n is a, c, g, or t

<400> SEQUENCE: 111
nngcggccgc caccatg                                                       17

<210> SEQ ID NO 112
<211> LENGTH: 30
<212> TYPE: DNA
<213> ORGANISM: artificial sequence
<220> FEATURE:
<223> OTHER INFORMATION: Primer

<400> SEQUENCE: 112
ctctaaatcc agtgacaagt ctgtctgcct                                         30

<210> SEQ ID NO 113
<211> LENGTH: 29
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: n is a, c, g, or t

<400> SEQUENCE: 113
nnnttaatta atcagctgga ccacagccg                                          29

<210> SEQ ID NO 114
<211> LENGTH: 28
<212> TYPE: DNA
<213> ORGANISM: artificial sequence
<220> FEATURE:
<223> OTHER INFORMATION: Primer

<400> SEQUENCE: 114
cgaattccca aacttaagct tggtaccg                                           28

<210> SEQ ID NO 115
<211> LENGTH: 26
<212> TYPE: DNA
<213> ORGANISM: artificial sequence
<220> FEATURE:
<223> OTHER INFORMATION: Primer

<400> SEQUENCE: 115
gcagcgtatc cacatagcgt aaaagg                                             26

<210> SEQ ID NO 116
<211> LENGTH: 33
<212> TYPE: DNA
<213> ORGANISM: artificial sequence
<220> FEATURE:
<223> OTHER INFORMATION: Primer -continued

<400> SEQUENCE: 116
tggcgccggt gatgtgaaag accccacctg tag                                33

<210> SEQ ID NO 117
<211> LENGTH: 38
<212> TYPE: DNA
<213> ORGANISM: artificial sequence
<220> FEATURE:
<223> OTHER INFORMATION: Primer

<400> SEQUENCE: 117
aatgtcgact atgcggccgc agatccgagc tcggtacc                           38

<210> SEQ ID NO 118
<211> LENGTH: 4
<212> TYPE: PRT
<213> ORGANISM: artificial sequence
<220> FEATURE:
<223> OTHER INFORMATION: Linker sequence

<400> SEQUENCE: 118

Ser Gly Ser Gly
1

<210> SEQ ID NO 119
<211> LENGTH: 4
<212> TYPE: PRT
<213> ORGANISM: artificial sequence
<220> FEATURE:
<223> OTHER INFORMATION: Linker sequence

<400> SEQUENCE: 119

Arg Ala Lys Arg
1

<210> SEQ ID NO 120
<211> LENGTH: 10
<212> TYPE: DNA
<213> ORGANISM: artificial sequence
<220> FEATURE:
<223> OTHER INFORMATION: Primer

<400> SEQUENCE: 120
tttttttttt                                                          10

<210> SEQ ID NO 121
<211> LENGTH: 64
<212> TYPE: DNA
<213> ORGANISM: homo sapiens

<400> SEQUENCE: 121
tgaccctgcc gtgtaccagc tgagagactc taaatccagt gacaagtctg tctgcctatt   60
cacc                                                                64

<210> SEQ ID NO 122
<211> LENGTH: 64
<212> TYPE: DNA
<213> ORGANISM: artificial sequence
<220> FEATURE:
<223> OTHER INFORMATION: Modified T cell receptor chain

<400> SEQUENCE: 122
tgaccctgcc gtgtaccagc tggggccctc taaatccagt gacaagtctg tctgcctatt   60
cacc                                                                        64

<210> SEQ ID NO 123
<211> LENGTH: 57
<212> TYPE: DNA
<213> ORGANISM: artificial sequence
<220> FEATURE:
<223> OTHER INFORMATION: Modified T cell receptor sequence

<400> SEQUENCE: 123
tgaccctgcc gtgtaccagc tgagagactc taaatccagt gacaagtctg tctgcct       57

<210> SEQ ID NO 124
<211> LENGTH: 57
<212> TYPE: DNA
<213> ORGANISM: artificial sequence
<220> FEATURE:
<223> OTHER INFORMATION: Modified T cell receptor sequence

<400> SEQUENCE: 124
aggcagacag acttgtcact ggatttagag tctctcagct ggtacacggc agggtca       57

<210> SEQ ID NO 125
<211> LENGTH: 41
<212> TYPE: DNA
<213> ORGANISM: artificial sequence
<220> FEATURE:
<223> OTHER INFORMATION: Modified vector sequence

<400> SEQUENCE: 125
ggccctctaa atccagtgac aagtctgtct gcctattcac c                        41

<210> SEQ ID NO 126
<211> LENGTH: 37
<212> TYPE: DNA
<213> ORGANISM: artificial sequence
<220> FEATURE:
<223> OTHER INFORMATION: Modified vector sequence

<400> SEQUENCE: 126
ggtgaatagg cagacagact tgtcactgga tttagag                             37

<210> SEQ ID NO 127
<211> LENGTH: 57
<212> TYPE: DNA
<213> ORGANISM: artificial sequence
<220> FEATURE:
<223> OTHER INFORMATION: DNA fragment

<400> SEQUENCE: 127
tgaccctgcc gtgtaccagc tgagagactc taaatccagt gacaagtctg tctgcct       57

<210> SEQ ID NO 128
<211> LENGTH: 27
<212> TYPE: DNA
<213> ORGANISM: artificial sequence
<220> FEATURE:
<223> OTHER INFORMATION: DNA fragment

<400> SEQUENCE: 128
tctctcagct ggtacacggc agggtca                                        27

<210> SEQ ID NO 129
<211> LENGTH: 37
<212> TYPE: DNA
<213> ORGANISM: artificial sequence

```
<220> FEATURE:
<223> OTHER INFORMATION: DNA fragment

<400> SEQUENCE: 129
ggtgaatagg cagacagact tgtcactgga tttagag                              37

<210> SEQ ID NO 130
<211> LENGTH: 64
<212> TYPE: DNA
<213> ORGANISM: artificial sequence
<220> FEATURE:
<223> OTHER INFORMATION: Vector sequence

<400> SEQUENCE: 130
ggtgaatagg cagacagact tgtcactgga tttagagtct ctcagctggt acacggcagg     60
gtca                                                                 64

<210> SEQ ID NO 131
<211> LENGTH: 24
<212> TYPE: DNA
<213> ORGANISM: artificial sequence
<220> FEATURE:
<223> OTHER INFORMATION: Primer

<400> SEQUENCE: 131
aattgatccg cggccgccac catg                                           24
```